(12) United States Patent
Hashimoto et al.

(10) Patent No.: US 8,431,325 B2
(45) Date of Patent: Apr. 30, 2013

(54) COMPOUND, RESIN, RESIST COMPOSITION AND METHOD FOR PRODUCING RESIST PATTERN

(75) Inventors: Kazuhiko Hashimoto, Toyonaka (JP); Koji Ichikawa, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 227 days.

(21) Appl. No.: 12/873,919

(22) Filed: Sep. 1, 2010

(65) Prior Publication Data
US 2011/0053086 A1 Mar. 3, 2011

(30) Foreign Application Priority Data
Sep. 2, 2009 (JP) .................................. 2009-202725

(51) Int. Cl.
| G03F 7/039 | (2006.01) |
| G03F 7/40  | (2006.01) |
| C07C 69/54 | (2006.01) |
| C07C 69/74 | (2006.01) |
| C08F 216/38| (2006.01) |
| C08F 22/14 | (2006.01) |

(52) U.S. Cl.
USPC ........ 430/270.1; 560/221; 560/220; 526/280; 526/282; 526/309; 430/330; 430/325; 430/326

(58) Field of Classification Search .................... None
See application file for complete search history.

(56) References Cited

U.S. PATENT DOCUMENTS

| 3,779,778 | A |   | 12/1973 | Smith et al. |
| 3,849,137 | A |   | 11/1974 | Barzynski et al. |
| 4,576,902 | A |   | 3/1986  | Saenger et al. |
| 4,670,581 | A | * | 6/1987  | Tanigaki .................... 560/108 |
| 4,822,716 | A |   | 4/1989  | Onishi et al. |
| 4,857,437 | A |   | 8/1989  | Banks et al. |
| 5,017,453 | A |   | 5/1991  | Onishi et al. |
| 5,059,698 | A | * | 10/1991 | Schulthess et al. ........... 549/375 |
| 5,073,476 | A |   | 12/1991 | Meier et al. |
| 5,198,520 | A |   | 3/1993  | Onishi et al. |
| 5,260,410 | A |   | 11/1993 | Schwalm |
| 5,453,341 | A |   | 9/1995  | Schwalm |
| 7,202,010 | B2 |  | 4/2007  | Yamada et al. |
| 7,575,850 | B2 |  | 8/2009  | Takata et al. |
| 2003/0099900 | A1 | | 5/2003 | Yamada et al. |
| 2008/0193874 | A1 | | 8/2008 | Takata et al. |
| 2008/0286691 | A1 | * | 11/2008 | Akita et al. ................ 430/286.1 |

FOREIGN PATENT DOCUMENTS

| DE | 39 14 407 A1 | 10/1990 |
| EP | 0 126 712 A1 | 11/1984 |
| EP | 2062882 A1 * | 5/2009 |
| JP | 55-164824 A | 12/1980 |
| JP | 60-63208 A * | 4/1985 |
| JP | 62-69263 A | 3/1987 |
| JP | 62-153853 A | 7/1987 |
| JP | 63-26653 A | 2/1988 |

(Continued)

OTHER PUBLICATIONS

Gadzhiev, CAN 139:164580 abstract from CAPLUS obtained with structures from SciFInder database from article published year 2003, in Neftekhimiya, vol. 43, Issue: 2, pp. 133-136, this abstract having only 3 pages.*

*Primary Examiner* — Cynthia Hamilton
(74) *Attorney, Agent, or Firm* — Birch, Stewart, Kolasch & Birch, LLP

(57) ABSTRACT

A compound of the present invention is represented by the formula (A);

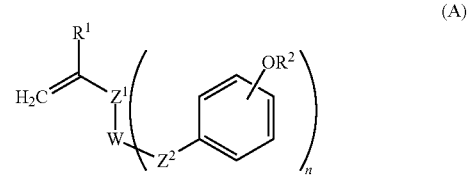

(A)

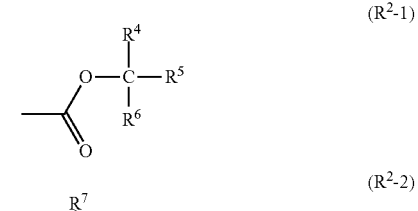

(R²-1)

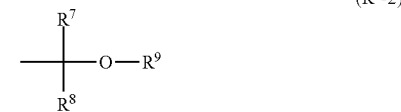

(R²-2)

wherein $R^1$ represents a hydrogen atom or a $C_1$ to $C_6$ alkyl group; $Z^1$ represents a single bond, —CO—O—* or —CO—O—$(CH_2)_k$—CO—O—*; $Z^2$ represents a single bond, *—O—CO—, *—CO—O—, *—O—$(CH_2)_k$—CO—, *—CO—$(CH_2)_k$—O—, *—O—$(CH_2)_k$—CO—O—, *—O—CO—$(CH_2)_k$—O— or *—O—CO—$(CH_2)_k$—O—CO—; k represents an integer of 1 to 6; * represents a binding position to W; W represents a $C_4$ to $C_{36}$ (n+1) valent alicyclic hydrocarbon group or a $C_6$ to $C_{18}$ (n+1) valent aromatic hydrocarbon group, one or more hydrogen atoms contained in the alicyclic hydrocarbon group and the aromatic hydrocarbon group may be replaced by a halogen atom, a $C_1$ to $C_{12}$ alkyl group, a $C_1$ to $C_{12}$ alkoxy group, a $C_2$ to $C_4$ acyl group or —$OR^{10}$; $R^{10}$ represents a hydrogen atom or a group represented by the formula (R²-2); $R^2$ represents a hydrogen atom, a group represented by the formula (R²-1) or (R²-2); n represents an integer of 1 to 3; $R^4$, $R^5$ and $R^6$ independently represent a $C_1$ to $C_{12}$ hydrocarbon group; $R^7$ and $R^8$ independently represent a hydrogen atom or a $C_1$ to $C_{12}$ hydrocarbon group; $R^9$ represents a $C_1$ to $C_{14}$ hydrocarbon group.

10 Claims, No Drawings

FOREIGN PATENT DOCUMENTS

| | | |
|---|---|---|
| JP | 63-146029 A | 6/1988 |
| JP | 63-146038 A | 6/1988 |
| JP | 63-163452 A | 7/1988 |
| JP | 11-52575 A | 2/1999 |
| JP | 2003-107708 A | 4/2003 |
| JP | 2008-209917 A | 9/2008 |

* cited by examiner

COMPOUND, RESIN, RESIST COMPOSITION AND METHOD FOR PRODUCING RESIST PATTERN

BACKGROUND OF THE INVENTION

1. Field of the Invention

The present invention relates to a compound, a resin, a resist composition and a method for producing a resist pattern.

2. Background Information

Compounds, 2-ethyl-2-adamanthyl methacrylate and p-hydroxystyrene, resins having structural units derived therefrom and resist compositions contain these resin are described in Patent document, JP2003-107708-A.

SUMMARY OF THE INVENTION

The present invention provides following inventions of <1> to <10>.

<1> A compound represented by the formula (A);

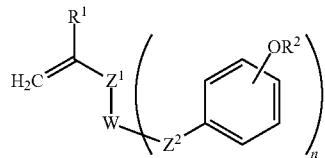

(A)

wherein $R^1$ represents a hydrogen atom or a $C_1$ to $C_6$ alkyl group;

$Z^1$ represents a single bond, —CO—O—* or —CO—O—$(CH_2)_k$—CO—O—*;

$Z^2$ represents a single bond, *—O—CO—, *—CO—O—, *—O—$(CH_2)_k$—CO—, *—CO—$(CH_2)_k$—O—, *—O—$(CH_2)_k$—CO—O—, *—O—CO—$(CH_2)_k$—O— or *—O—CO—$(CH_2)_k$—O—CO—;

k represents an integer of 1 to 6;

* represents a binding position to W;

W represents a $C_4$ to $C_{36}$ (n+1) valent alicyclic hydrocarbon group or a $C_6$ to $C_{18}$ (n+1) valent aromatic hydrocarbon group, one or more hydrogen atoms contained in the alicyclic hydrocarbon group and the aromatic hydrocarbon group may be replaced by a halogen atom, a $C_1$ to $C_{12}$ alkyl group, a $C_1$ to $C_{12}$ alkoxy group, a $C_2$ to $C_4$ acyl group or —$OR^{10}$;

$R^{10}$ represents a hydrogen atom or a group represented by the formula ($R^2$-2);

$R^2$ represents a hydrogen atom, a group represented by the formula ($R^2$-1) or a group represented by the formula ($R^2$-2);

n represents an integer of 1 to 3;

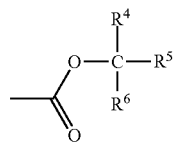

($R^2$-1)

wherein $R^4$, $R^5$ and $R^6$ independently represent a $C_1$ to $C_{12}$ hydrocarbon group;

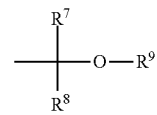

($R^2$-2)

wherein $R^7$ and $R^8$ independently represent a hydrogen atom or a $C_1$ to $C_{12}$ hydrocarbon group;

$R^9$ represents a $C_1$ to $C_{14}$ hydrocarbon group.

<2> The compound according to <1>, wherein the compound represented by the formula (A) is a compound represented by the formula (A1);

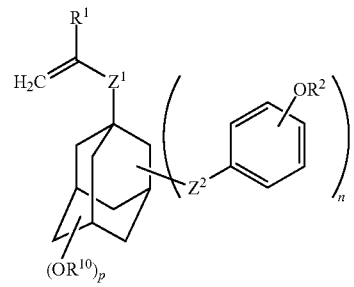

(A1)

wherein $R^1$, $R^2$, $R^{10}$, $Z^1$, $Z^2$ and n represent the same meaning as defined above.

p represents an integer of 0 to 3, provided that n+p is an integer of 1 to 3.

<3> The compound according to <1> or <2>, wherein the $Z^1$ is —CO—O—*.

<4> The compound according to any one of <1> to <3>, wherein the $Z^2$ is *—O—$(CH_2)_k$—CO— or *—O—CO—$(CH_2)_k$—O—CO—, wherein k represents the same meaning as defined above.

<5> The compound according to any one of <1> to <4>, wherein the n represents 1.

<6> A resin comprising a structural unit derived from the compound any one of <1> to <5>.

<7> The resin according to <6>, which further comprising an acid-labile group, and being insoluble or poorly soluble in aqueous alkali solution but becoming soluble in aqueous alkali solution by the action of acid.

<8> A resist composition comprising a resin according to <6> or <7>, and an acid generator.

<9> The resist composition according to <8>, which further comprises a basic compound.

<10> A method for producing a resist pattern comprising steps of;

(1) applying the resist composition of the present invention onto a substrate;

(2) drying the applied composition to form a composition layer;

(3) exposing to the composition layer using a exposure device;

(4) baking the exposed composition layer and, (5) developing the baked composition layer using a developing apparatus.

According to the resin and the resist composition of the present invention, it is possible to achieve satisfactory pattern line edge roughness in the pattern formed.

DETAILED DESCRIPTION OF THE PREFERRED EMBODIMENTS

"(meth)acrylic monomer" means at least one monomer having a structure of "$CH_2=CH-CO-$" or "$CH_2=C(CH_3)-CO-$", as well as "(meth)acrylate" and "(meth)acrylic acid" mean "at least one acrylate or methacrylate" and "at least one acrylic acid or methacrylic acid," respectively.

A compound of the present invention is a compound represented by the formula (A);

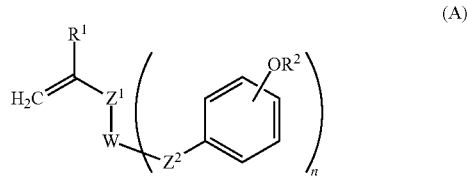

(A)

wherein $R^1$ represents a hydrogen atom or a $C_1$ to $C_6$ alkyl group;

$Z^1$ represents a single bond, $-CO-O-$* or $-CO-O-(CH_2)_k-CO-O-$*;

$Z^2$ represents a single bond, *$-O-CO-$, *$-CO-O-$, *$-O-(CH_2)_k-CO-$, *$-CO-(CH_2)_k-O-$, *$-O-(CH_2)_k-CO-O-$, *$-O-CO-(CH_2)_k-O-$ or *$-O-CO-(CH_2)_k-O-CO-$;

k represents an integer of 1 to 6;

* represents a binding position to W;

W represents a $C_4$ to $C_{36}$ (n+1) valent alicyclic hydrocarbon group or a $C_6$ to $C_{18}$ (n+1) valent aromatic hydrocarbon group, one or more hydrogen atoms contained in the alicyclic hydrocarbon group and the aromatic hydrocarbon group may be replaced by a halogen atom, a $C_1$ to $C_{12}$ alkyl group, a $C_1$ to $C_{12}$ alkoxy group, a $C_2$ to $C_4$ acyl group or $-OR^{10}$;

$R^{10}$ represents a hydrogen atom or a group represented by the formula ($R^2$-2);

$R^2$ represents a hydrogen atom, a group represented by the formula ($R^2$-1) or a group represented by the formula ($R^2$-2);

n represents an integer of 1 to 3;

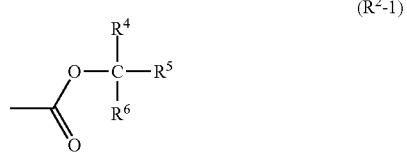

($R^2$-1)

wherein $R^4$, $R^5$ and $R^6$ independently represent a $C_1$ to $C_{12}$ hydrocarbon group;

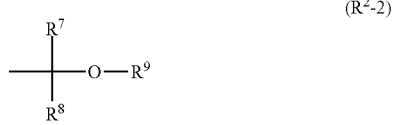

($R^2$-2)

wherein $R^7$ and $R^8$ independently represent a hydrogen atom or a $C_1$ to $C_{12}$ hydrocarbon group;

$R^9$ represents a $C_1$ to $C_{14}$ hydrocarbon group.

Examples of the alkyl group include methyl, ethyl, n-propyl, iso-propyl, n-butyl, sec-butyl, tert-butyl, n-pentyl, n-hexyl, heptyl, 2-ethylhexyl, octyl, nonyl, decyl, undecyl, and dodecyl groups.

Examples of the alicyclic hydrocarbon group include a monovalent alicyclic hydrocarbon group such as cycloalkyl group such as cyclopropyl, cyclobutyl, cyclopentyl, cyclohexyl, cycloheptyl, cyclooctyl, cyclononyl, and cyclodecyl groups, norbornyl group, 1-adamantyl group, 2-adamantly) group, isobornyl group, and a divalent clicyclic hydrocarbon group such as a cycloalkylene group such as cyclopropylene, cyclobutylene, cyclopentylene, cyclohexylene, cycloheptylene, cyclooctylene, cyclononylene, and cyclodecylene groups, norbornylene group, adamantylene group, isobornylene group.

Examples of the aromatic hydrocarbon groups include a monovalent aromatic hydrocarbon group such as an aryl group such as phenyl, naphthyl and anthryl groups, and a divalent aromatic hydrocarbon group such as phenylene, naphthylene and anthrylene groups.

Examples of the halogen atom include fluorine, chlorine, bromine and iodine atoms.

Examples of the alkoxy group include methoxy, ethoxy, n-propoxy, iso-propoxy, n-butoxy, sec-butoxy, tert-butoxy, n-pentoxy, n-hextoxy, heptoxy, octoxy, 2-ethylhexyloxy, nonyloxy, decyloxy, undecyloxy and dodecyloxy groups.

Examples of the acyl group include acetyl, propionyl and butyryl groups.

The hydrocarbon group may be any of a saturated and unsaturated hydrocarbon groups, and any of an alkyl, monovalent alicyclic and monovalent aromatic hydrocarbon groups. Also, the hydrocarbon group may include a group formed by combining any of the above-mentioned groups such as aralkyl and alkyl-aryl groups.

The unsaturated hydrocarbon group may include an alkenyl (such as vinyl and allyl groups), and alkynyl (such as ethynyl group) groups.

Examples of the aralkyl group include, for example, benzyl and naphthylmethyl groups.

In the compound represented by the formula (A), particularly $R^1$ is preferably a hydrogen atom or methyl group.

$Z^1$ is preferably a single bond or $-CO-O-$*, wherein * represents a binding position to W.

$Z^2$ is preferably *$-O-CO-$, *$-CO-O-$, *$-O-(CH_2)_k-CO-$, *$-O-(CH_2)_k-CO-O-$ or *$-O-CO-(CH_2)_k-O-CO-$, and more preferably *$-O-(CH_2)_k-CO-$ or *$-O-CO-(CH_2)_k-O-CO-$, among these, more preferred are those in which k is 1.

W is preferably a group represented by the formula (W-1);

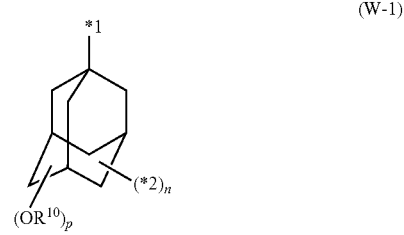

(W-1)

wherein $R^{10}$ represents a hydrogen atom, a group represented by the formula ($R^2$-1) or a group represented by the formula ($R^2$-2);

n represents the same meaning as defined above;

p represents an integer of 0 to 3, provided that n+p is an integer of 1 to 3;

*1 represents a binding position to $Z^1$;

*2 represents a binding position to $Z^2$.

Examples of the groups represented by the formula ($R^2$-1) and the groups represented by the formula ($R^2$-2) includes groups below. Here, * represents a binding position to W.

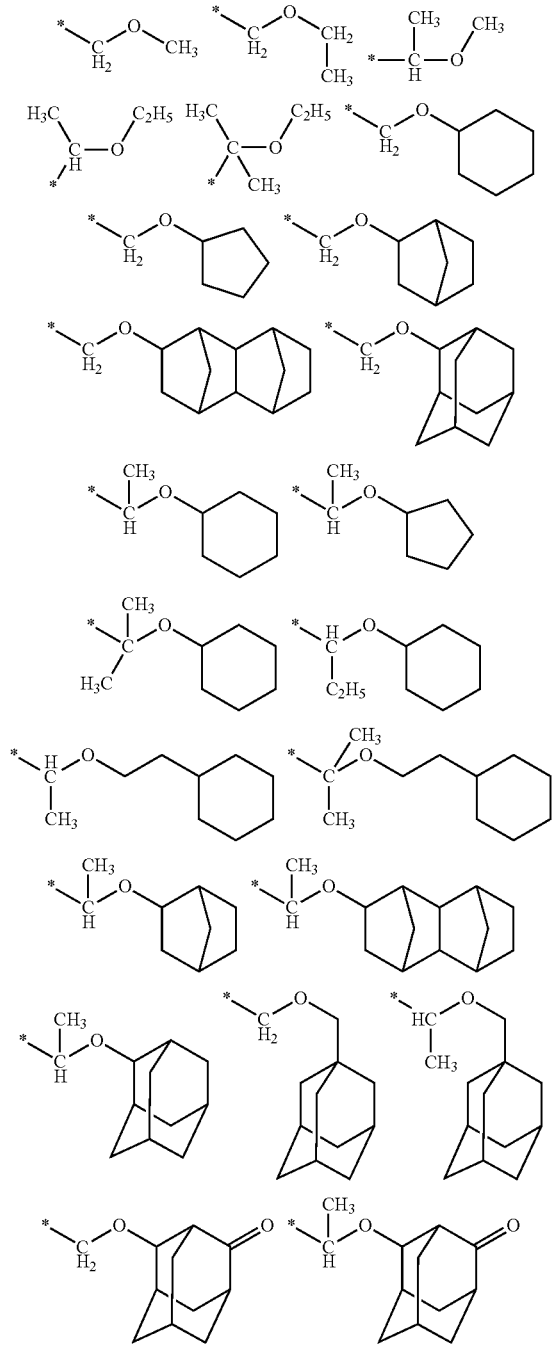

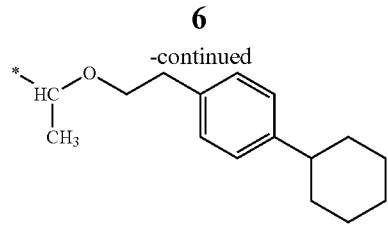

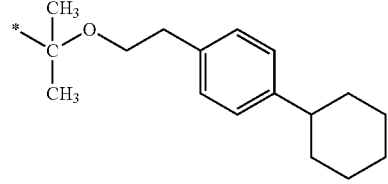

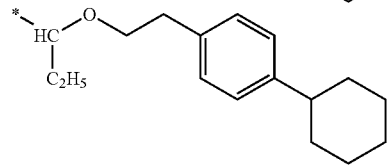

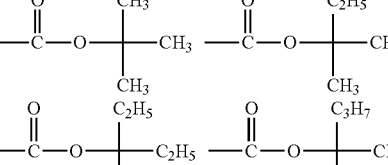

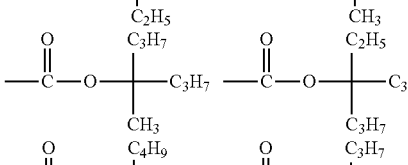

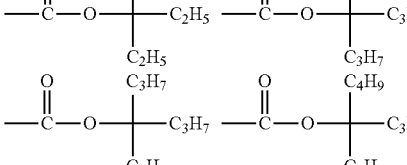

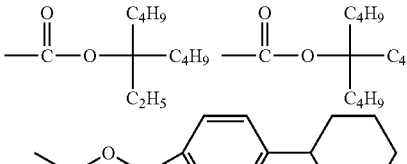

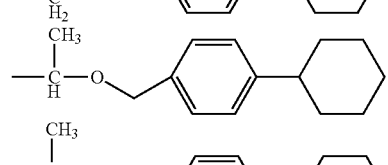

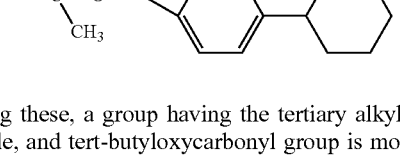

Among these, a group having the tertiary alkyl group is preferable, and tert-butyloxycarbonyl group is more preferable.

For $R^2$, a group represented by the formula ($R^2$-1) in which $R^4$, $R^5$ and $R^6$ independently represent a $C_1$ to $C_4$ alkyl group is preferable, and a group represented by the formula ($R^2$-2) in which $R^7$ and $R^8$ independently represent a hydrogen atom or a $C_1$ to $C_4$ alkyl group is preferable, and also, a group represented by the formula ($R^2$-2) in which $R^9$ represents any one of a group represented by any one of the formula ($R^9$-1), the formula ($R^9$-2), the formula ($R^9$-3) and the formula ($R^9$-4) is more preferable. Among these, a hydrogen atom is preferable for $R^2$.

—$CH_3$ ($R^9$-1)

—$C_2H_5$ ($R^9$-2)

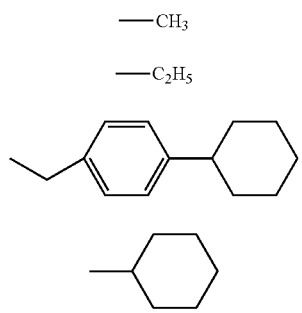
($R^9$-3)

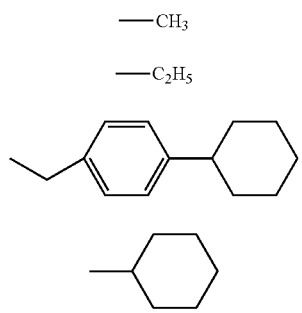
($R^9$-4)

Further, n is preferably 1, and p is preferably 0 or 1.

As the compound represented by the formula (A), compounds represented by the formula (A1) to the formula (A4) are preferable;

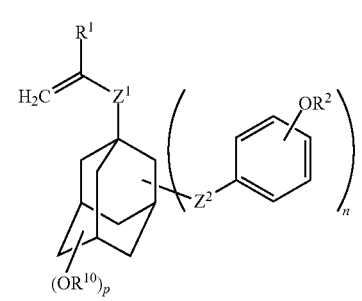
(A1)

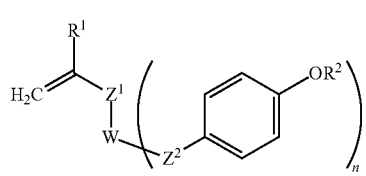
(A2)

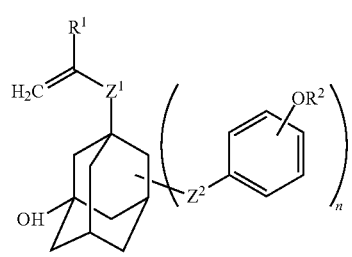
(A3)

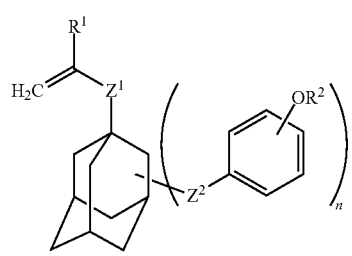
(A4)

wherein $R^1$, $R^2$, $R^{10}$, $Z^1$, $Z^2$, W, n and p represent the same meaning as defined above; provided that n+p represents an integer of 1 to 3.

As the compound represented by the formula (A1), compound represented by the formula (A1a) or the formula (A1b) below is preferable;

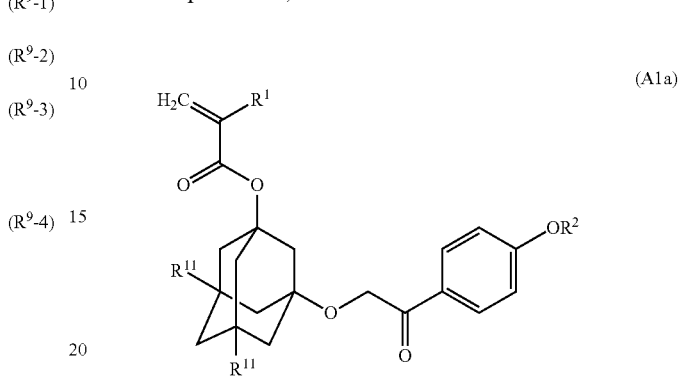
(A1a)

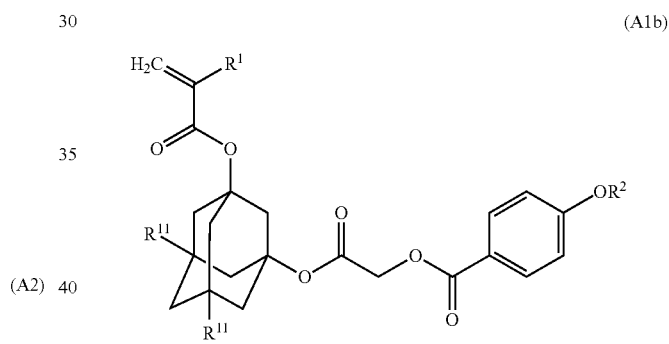
(A1b)

wherein $R^{11}$ represents a hydrogen atom, a hydroxy group or —$OR^{10}$;

$R^1$, $R^2$ and $R^{10}$ independently represent the same meaning as defined above.

As the compound represented by the formula (A1), a compound represented by the formula (A1a1), the formula (A1a2), the formula (A1b1) or the formula (A1b2) below is more preferable;

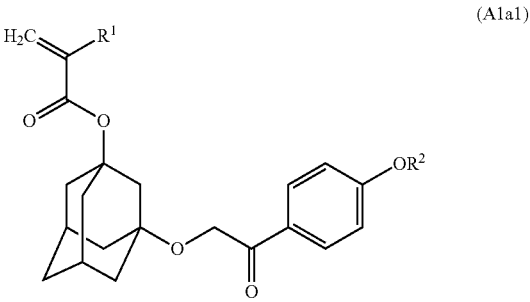
(A1a1)

-continued
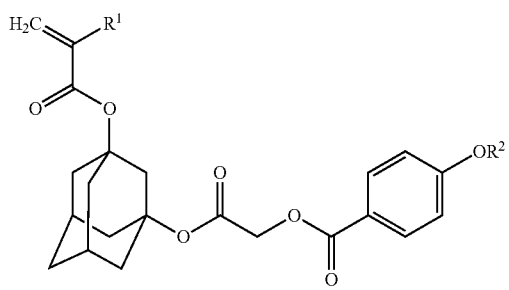
(A1b1)
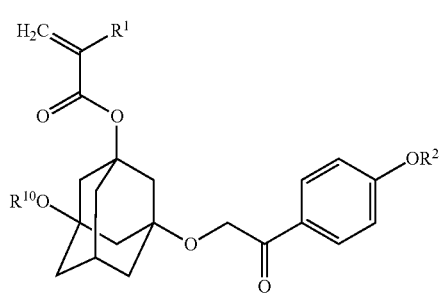
(A1a2)
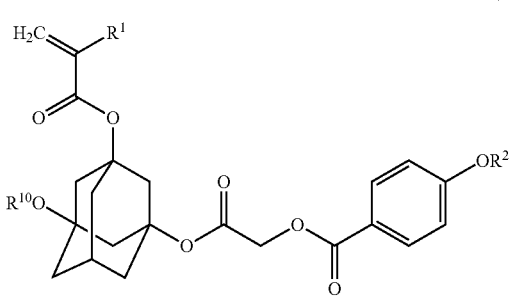
(A1b2)
wherein $R^1$, $R^2$ and $R^{10}$ represent the same meaning as defined above.
In the compound represented by the formula (A1a1), the formula (A1a2), the formula (A1b1) or the formula (A1b2), a compound in which $R^1$ is a hydrogen atom or methyl group, and $R^2$ is a hydrogen atom is preferable.
Examples of the compound represented by the formula (A) include compounds below.
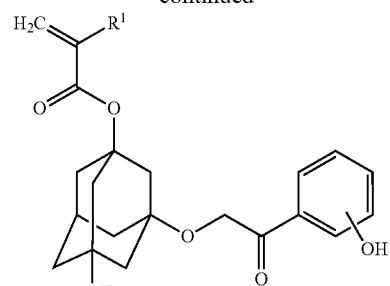
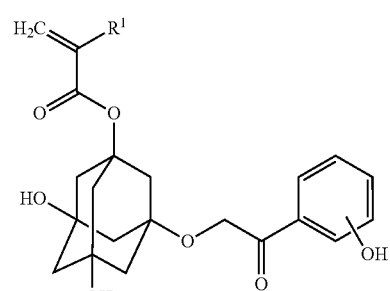
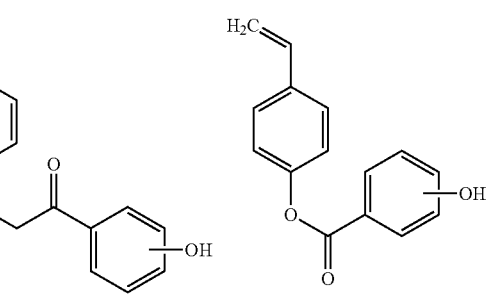
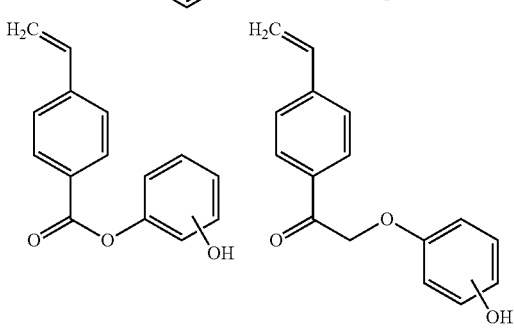

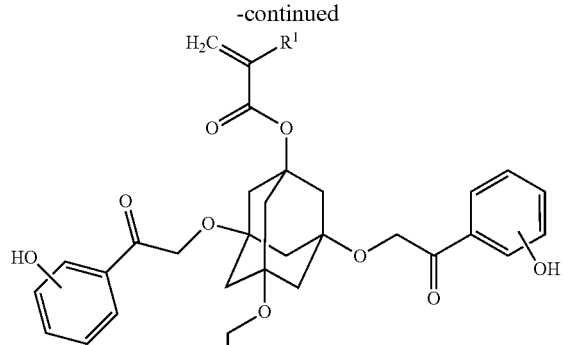
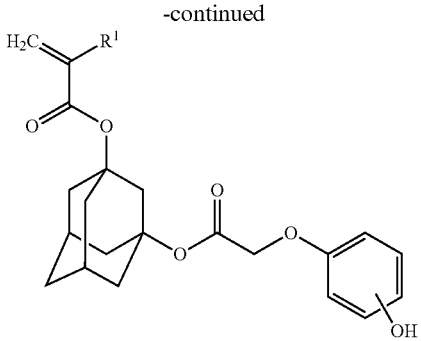
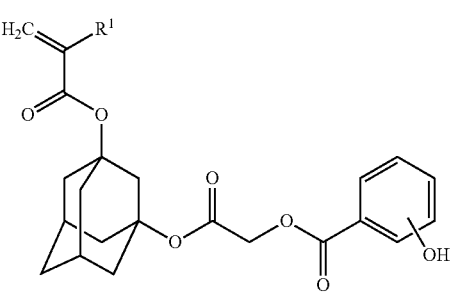
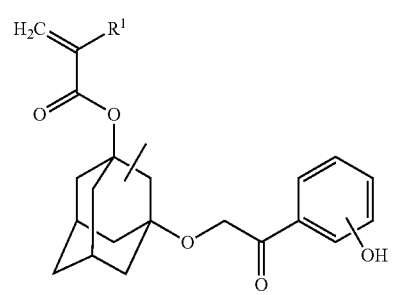
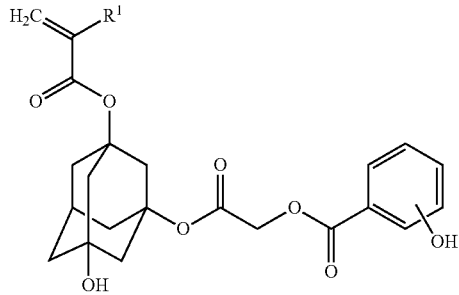
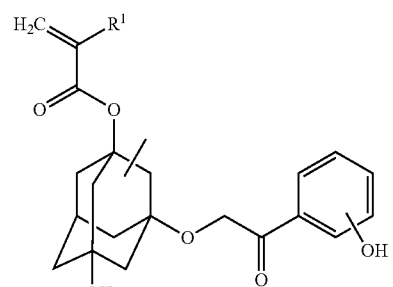
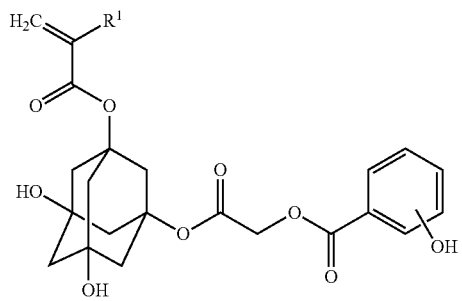
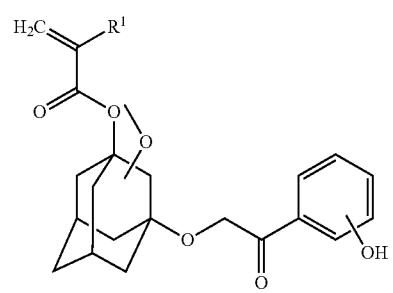
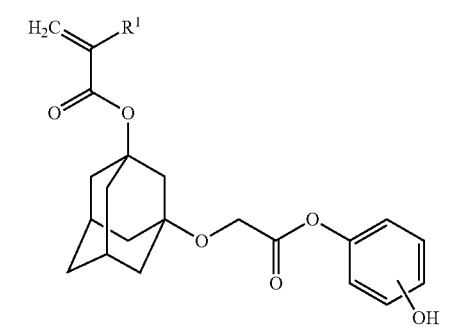
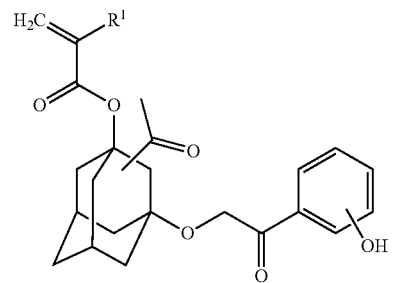

-continued
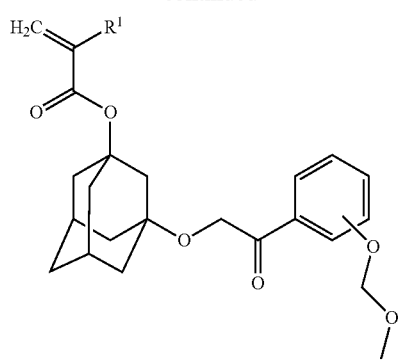
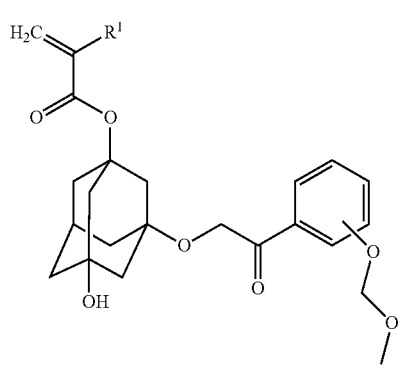
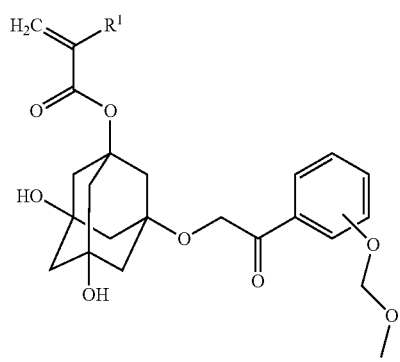
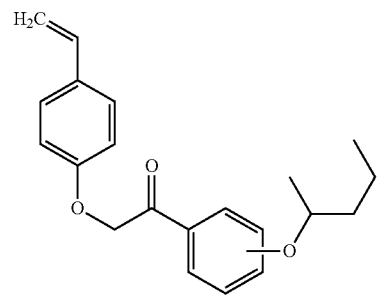
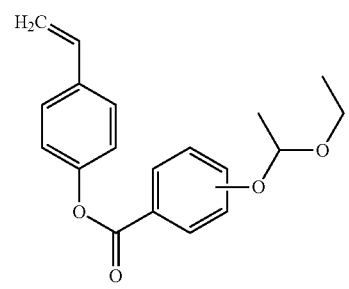
-continued
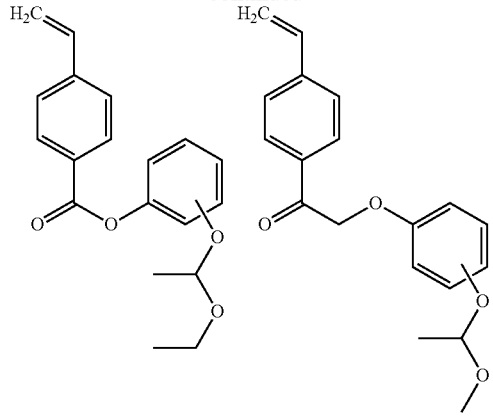
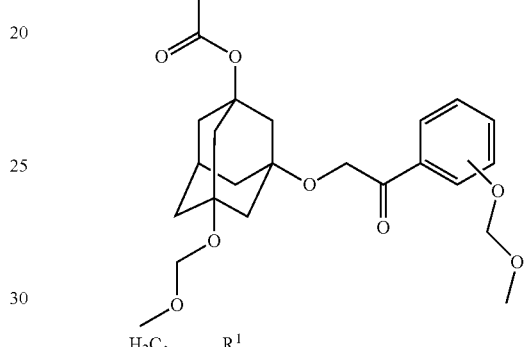
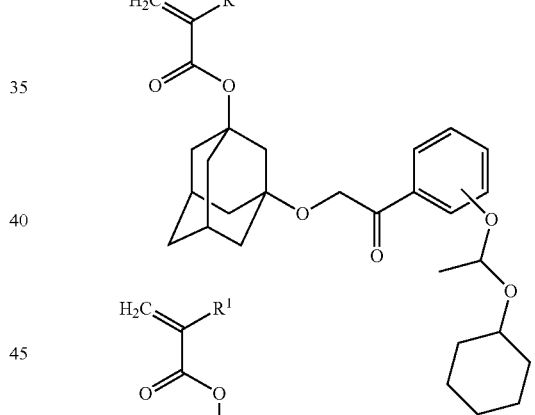
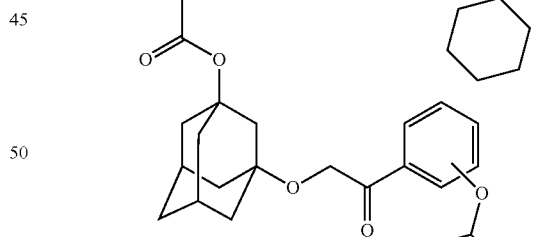
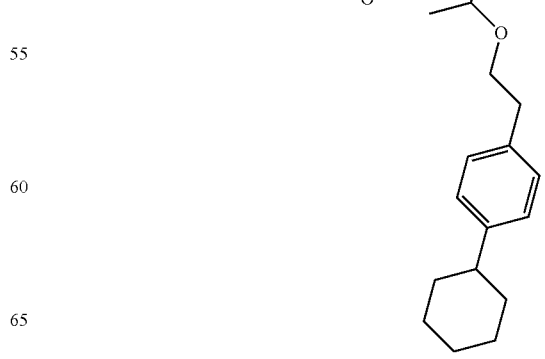

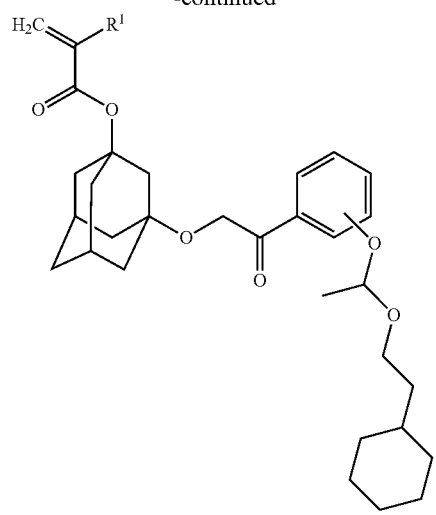
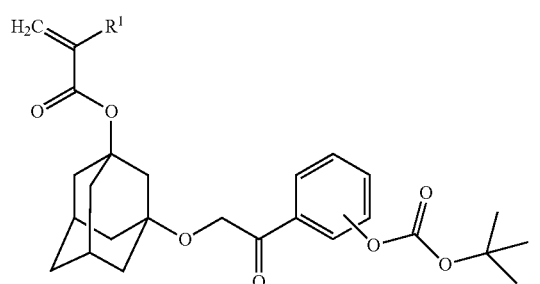
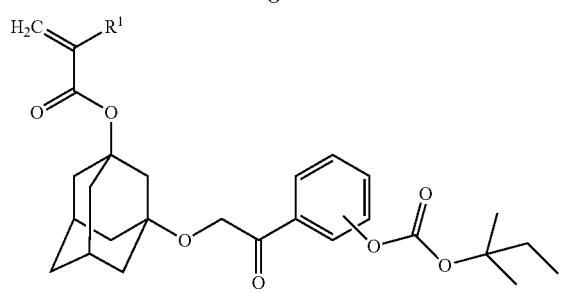
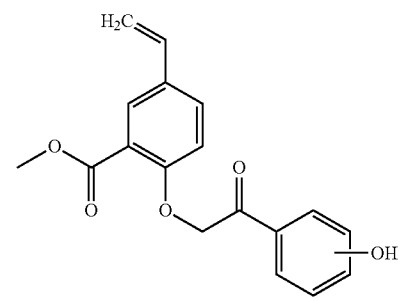
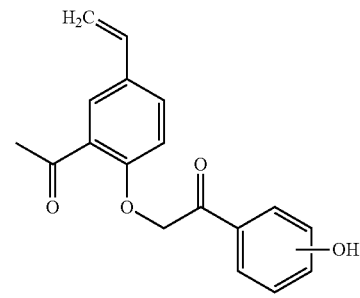
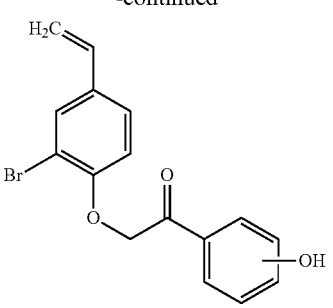
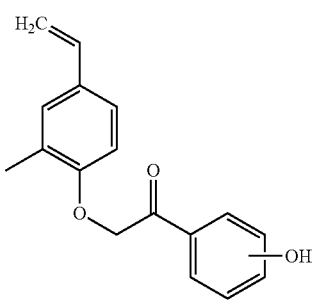
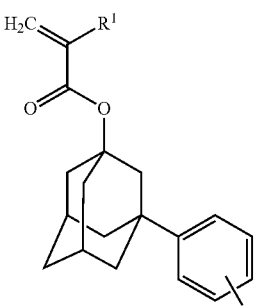
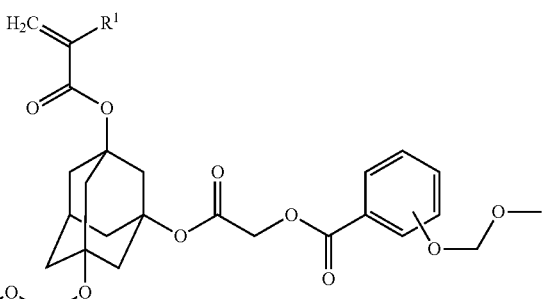
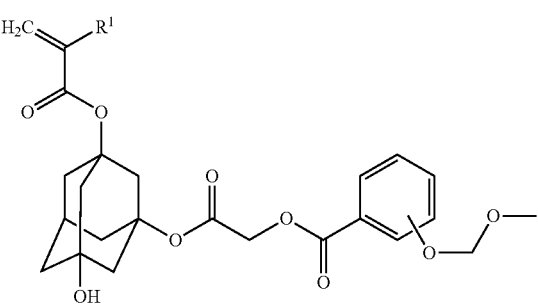

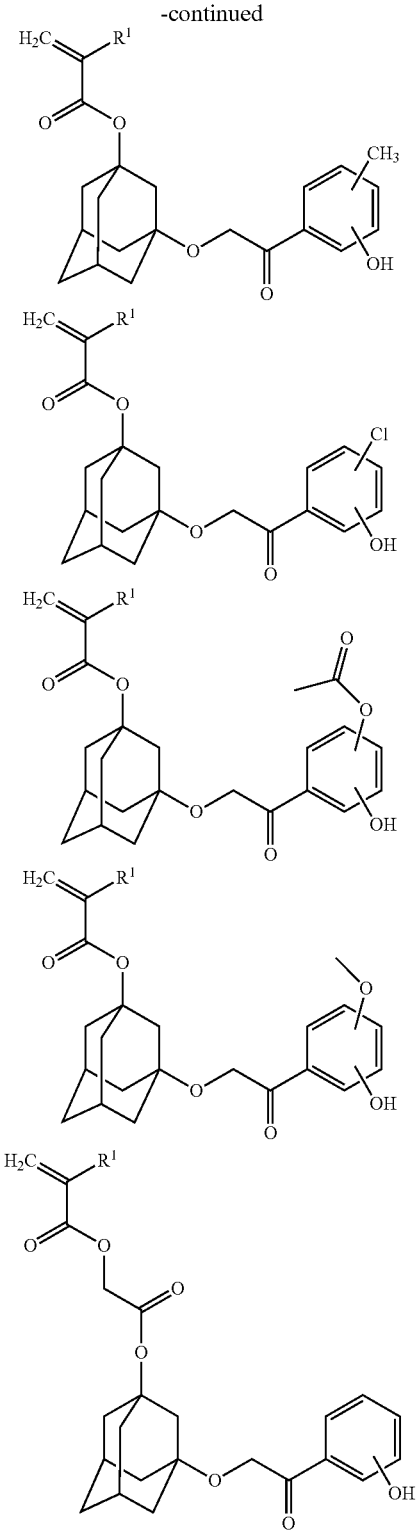

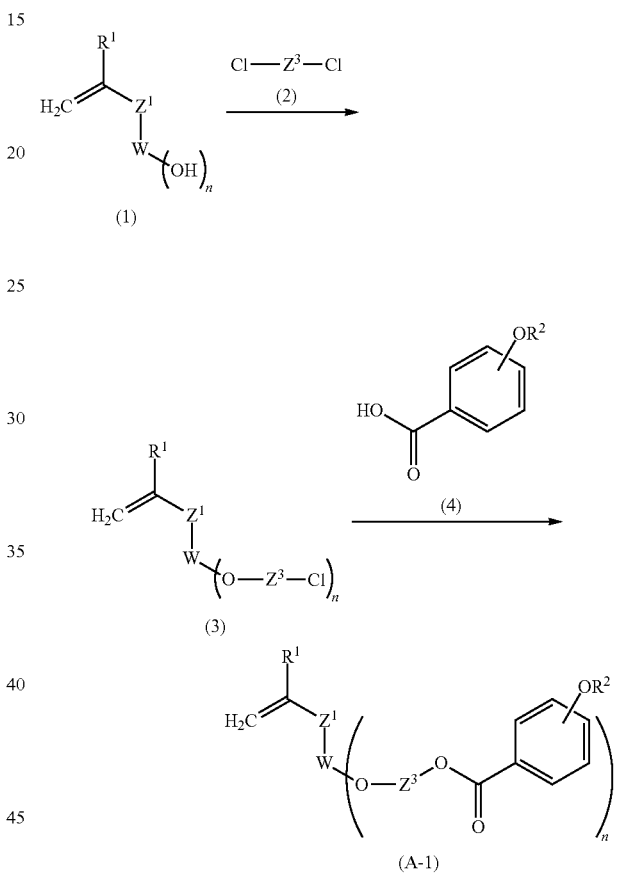

chloroacetyl chloride in presence of a basic catalyst in a solvent. Preferred examples of the basic catalyst include pyridine. Preferred examples of the solvent include tetrahydrofuran.

The compound represented by the formula (A-1) in which $Z^2$ is *—O—CO—$(CH_2)_k$—O—CO— can be obtained by reacting the obtained compound represented by the formula (3) with a compound represented by the formula (4) such as benzoic acid in presence of a catalyst in a solvent. Preferred examples of the catalyst include a mixture of calcium carbonate and potassium iodide. Preferred examples of the solvent include N,N-dimethylformamide.

wherein $R^1$, $R^2$, $Z^1$, W and n represent the same meaning as defined above;

$Z^3$ represents *—CO—$(CH_2)_k$—.

Also, the compound represented by the formula (A-2) in which $Z^2$ is *—O—$CH_2$—CO— can be obtained by replacing a hydrogen atom of methyl group in a compound represented by the formula (5) such as 4-acetylphenol to a halogen atom (preferably a bromine atom) in a solvent (preferably chloroform) to obtain a compound represented by the formula (6), and reacting the obtained compound represented by the formula (6) with a compound represented by the formula (7), for example, 3-hydroxy-1-adamantyl(meth)acrylate or 3,5-dihydroxy-1-adamantyl(meth)acrylate in presence of a catalyst in a solvent. Preferred examples of the catalyst include a mixture of calcium carbonate and potassium iodide. Preferred examples of the solvent include N,N-dimethylformamide.

The compound represented by the formula (A) can be produced, for example, by a method described in schemes below.

A compound represented by the formula (3) can be obtained by reacting a compound represented by the formula (1) as a starting material, for example, 3-hydroxy-1-adamantyl(meth)acrylate or 3,5-dihydroxy-1-adamantyl(meth)acrylate with a compound represented by the formula (2) such as

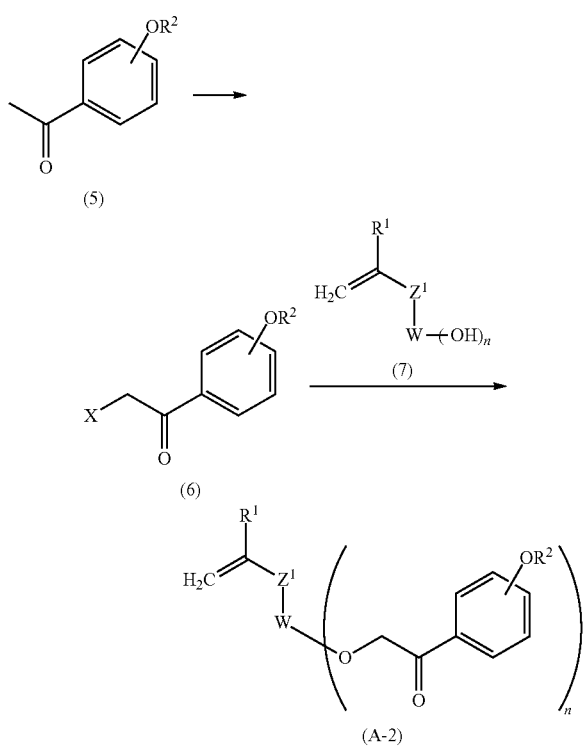

wherein $R^1$, $R^2$, $Z^1$, W and n represent the same meaning as defined above;

X represents a halogen atom.

A resin of the present invention contains a structural unit derived from the compound represented by the formula (A). The resin may contain the compound represented by the formula (A) singly or in combination with two or more. The resin of the present invention may be a resin having the structural unit derived from the compound represented by the formula (A) alone, and preferably a resin further contain a structural unit derived from a compound having an acid-labile group. Such resin is insoluble or poorly soluble in aqueous alkali solution, and can dissolve in aqueous alkali solution by the action of acid.

The acid-labile group include —COOR group, examples of R include tert-butyl group, methoxymethyl, ethoxymethyl, 1-ethoxyethyl, 1-isobutoxyethyl, 1-isopropoxyethyl, 1-ethoxypropyl, 1-(2-methoxyethoxy)ethyl, 1-(2-acetoxyethoxy)ethyl, 1-[2-(1-adamantyloxy)ethoxy]ethyl, 1-[2-(1-adamantanecarbonyloxy)ethoxy]ethyl, tetrahydro-2-furyl, tetrahydro-2-pyranyl, isobornyl, 1-alkylcycloalkyl, 2-alkyl-2-adamantyl and 1-(1-adamantyl)-1-alkylalkyl groups.

The resin of the present invention can be produced by conducting addition polymerization reaction of a monomer or monomers having the acid-labile group and a carbon-carbon double bond.

Among the monomers, as the acid-labile group, those having a bulky group such as an alicyclic structure (e.g. a 2-alkyl-2-adamantyl and a 1-(1-adamantyl)-1-alkylalkyl groups) are preferable, since excellent resolution tends to be obtained when the resin obtained is used.

Examples of such monomer containing the bulky group include a 2-alkyl-2-adamantyl(meth)acrylate, 1-(1-adamantyl)-1-alkylalkyl(meth)acrylate, a 2-alkyl-2-adamantyl 5-norbornene-2-carboxylate, a 1-(1-adamantyl)-1-alkylalkyl 5-norbornene-2-carboxylate, a 2-alkyl-2-adamantyl α-chloroacrylate and a 1-(1-adamantyl)-1-alkylalkyl α-chloroacrylate.

Particularly, the 2-alkyl-2-adamantyl(meth)acrylate or the 2-alkyl-2-adamantyl α-chloroacrylate is preferably used as the monomer since the resist composition having excellent resolution tend to be obtained.

Specific examples of the 2-alkyl-2-adamantyl(meth)acrylate include 2-methyl-2-adamantyl acrylate, 2-methyl-2-adamantyl methacrylate, 2-ethyl-2-adamantyl acrylate, 2-ethyl-2-adamantyl methacrylate, 2-n-butyl-2-adamantyl acrylate, 2-n-butyl-2-adamantyl methacrylate. Specific examples of the 2-alkyl-2-adamantyl α-chloro(meth)acrylate include 2-methyl-2-adamantyl α-chloroacrylate and 2-ethyl-2-adamantyl α-chloroacrylate.

Among these, 2-ethyl-2-adamantyl(meth)acrylate or 2-isopropyl-2-adamantyl(meth)acrylate is preferably because of the resist composition having excellent sensitivity and heat resistance tends to be obtained.

The 2-alkyl-2-adamantyl(meth)acrylate can be generally produced by reacting a 2-alkyl-2-adamantanol or a metal salt thereof with an acrylic halide or methacrylic halide.

In addition to structural units derived from compounds represented by the formula (A) and structural units derived from monomers that have acid-labile groups, the resin used in the present invention may includes structural units derived from acid-stable monomers. Here, the structure derived from the acid-stable monomer means a structure that is not cleaved by the acid generator mentioned below.

Specific examples include;

a structural unit derived from a monomer such as acrylic acid and methacrylic acid;

a structural unit derived from an aliphatic unsaturated dicarboxylic anhydride such as maleic anhydride and itaconic anhydride;

a structural unit derived from 2-norbornene;

a structural unit derived from (meth)acrylonitrile;

a structural unit derived from (meth)acrylic esters having —COO—CH(R')$_2$ or —COO—CH$_2$(R'), wherein R' represents alkyl or 1-adamantyl group;

a structural unit derived from a styrene monomer such as p- or m-hydroxystyrene;

a structural unit derived from (meth)acryloyloxy-γ-butyrolactone having a lactone ring which may be substituted with an alkyl group;

a structural unit derived from a monomer having 1-adamantyl group which may have a hydroxy group.

Specific examples of the acid-stable monomer include 3-hydroxy-1-adamantyl(meth)acrylate, 3,5-dihydroxy-1-adamantyl(meth)acrylate, α-(meth)acryloyloxy-γ-butyrolactone, β-(meth)acryloyloxy-γ-butyrolactone, a monomer giving a structural unit represented by the formula (a), a monomer giving a structural unit represented by the formula (b), p- or m-hydroxystyrene, 2-norbornene, maleic anhydride and itaconic anhydride.

Among these, the resist obtained from a resin having any of a structural unit derived from the styrene monomer, a structural unit derived from 3-hydroxy-1-adamantyl(meth)acrylate, a structural unit derived from 3,5-dihydroxy-1-adamantyl(meth)acrylate, a structural unit represented by the formula (a), a structural unit represented by the formula (b) and a structural unit represented by the formula (f) is preferable because the adhesiveness of resist composition to a substrate and resolution of resist composition tend to be improved.

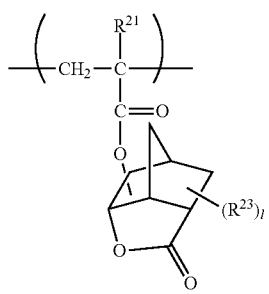
(a)

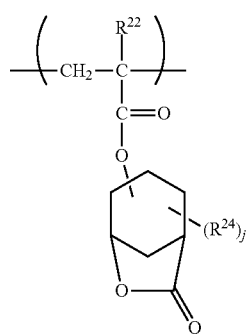
(b)

wherein $R^{21}$ and $R^{22}$ independently represent a hydrogen atom or methyl group;

$R^{23}$ and $R^{24}$ independently represent a hydrogen atom, methyl group, trifluoromethyl group or a halogen atom;

i and j represents an integer of 1 to 3.

Examples of the (meth)acryloyloxy-γ-butyrolactone include α-acryloyoxy-γ-butyrolactone, α-methacryloxy-γ-butyrolactone, α-acryloyloxy-β-γ-butyrolactone, β-dimethyl-γ-butyrolactone, α-methacryloyloxy-β-γ-butyrolactone, β-dimethyl-γ-butyrolactone, α-acryloyloxy-α-methyl-γ-butyrolactone, α-methacryloyloxy-α-methyl-γ-butyrolactone, β-acryloyloxy-γ-butyrolactone, β-methacryloyloxy-γ-butyrolactone and β-methacryloyloxy-α-meth-γ-butyrolactone.

When KrF excimer laser lithography and EUV or EB lithography are used, even in the case of using a structure unit derived from a styrene monomer as the structure unit of the resin, the resist composition having sufficient transparency can be obtained. Such resins can be obtained by radical-polymerizing the corresponding (meth)acrylic ester monomer with acetoxystyrene and styrene followed by de-acetylating them with an acid.

Specific examples of the monomer giving the structural unit derived from styrene monomers include monomers below.

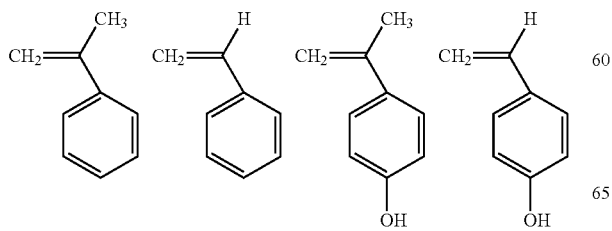

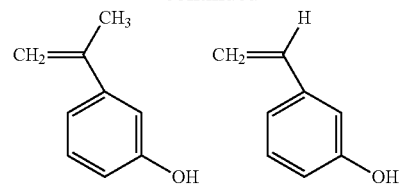

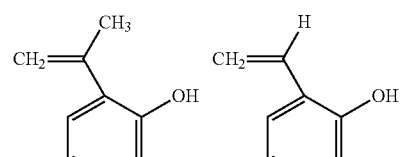

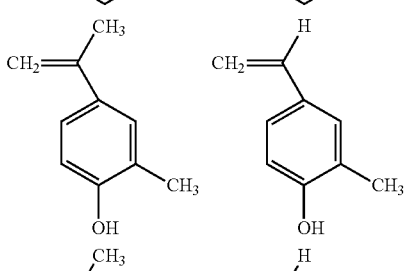

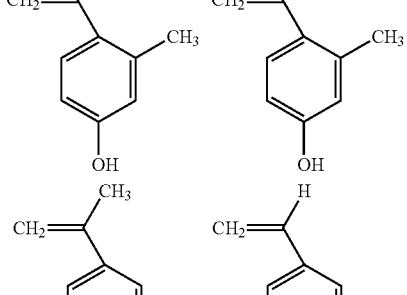

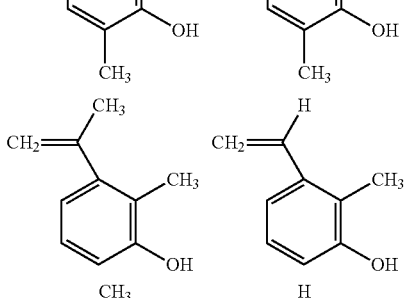

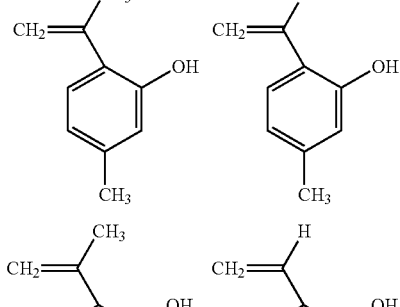

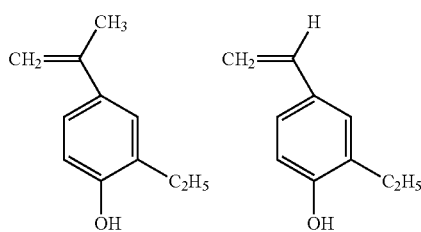

Among styrene monomers, 4-hydroxystyrene or 4-hydroxy-α-methylstyrene is particular preferable.

The resin containing a structural unit derived from 2-norbornene shows strong structure because the alicyclic group is directly present on its main chain and shows a property that dry etching resistance is excellent. The structural unit derived from 2-norbornene can be introduced into the main chain by radical polymerization using an aliphatic unsaturated dicarboxylic anhydride such as maleic anhydride and itaconic anhydride together in addition to corresponding 2-norbornene. Therefore, the structural unit formed by opening of double bond of norbornene can be represented by the formula (c), and the structural unit formed by opening of double bond of maleic anhydride and itaconic anhydride can be represented by the formula (d) and (e), respectively.

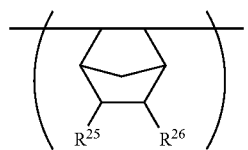

(c)

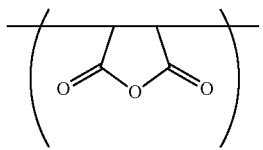

(d)

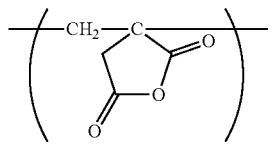

(e)

wherein $R^{25}$ and $R^{26}$ in the formula (c) independently represent a hydrogen atom, a $C_1$ to $C_3$ alkyl group, a carboxyl group, a cyano group or —COOU, or $R^{25}$ and $R^{26}$ are bonded together to form a group represented by —C(=O)OC(=O)—, one or more hydrogen atoms contained in the alkyl group may be replaced by a hydroxy group.

U represents an optionally substituted $C_1$ to $C_8$ alkyl group or 2-oxooxolan-3- or -4-yl group, the alkyl group may be substituted with a hydroxy group and an alicyclic hydrocarbon group.

Specific examples of the alkyl group include methyl, ethyl and propyl groups, and specific examples of the alkyl group having a hydroxy group include hydroxymethyl and 2-hydroxyethyl groups.

Specific examples of monomer giving the structural unit represented by the formula (c) include the following compounds;

2-norbornene, 2-hydroxy-5-norbornene, 5-norbornene-2-carboxylic acid, methyl 5-norbornene-2-carboxylate, 2-hydroxy-1-ethyl 5-norbornene-2-carboxylate, 5-norbornene-2-methanol, and 5-norbornene-2,3-dicarboxylic acid anhydride.

The resin can contain a structural unit represented by the formula (f) as an acid-stable group.

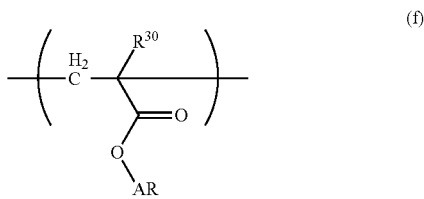

(f)

wherein $R^{30}$ represents a hydrogen atom, a methyl group or a trifluoromethyl group;

AR represents a $C_1$ to $C_{30}$ hydrocarbon group, and at least one or more hydrogen atoms contained in the hydrocarbon group is replaced with fluorine atom, one or more —CH$_2$— contained in the hydrocarbon group may be replaced by —O—, —S— or —N(R$^c$)—, and a hydrogen atom contained in the hydrocarbon group may be replaced by a hydroxy group or a $C_1$ to $C_6$ alkyl group;

$R^c$ represents a hydrogen atom or a $C_1$ to $C_6$ alkyl group.

Specific examples of the structural unit represented by the formula (f) include monomers below.

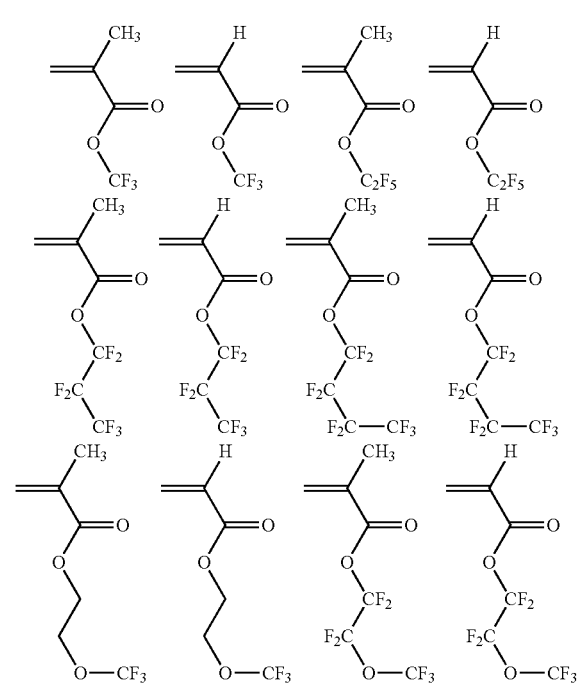

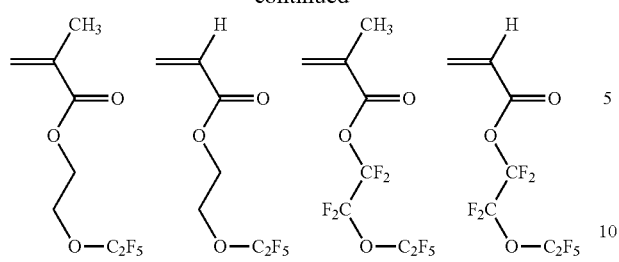
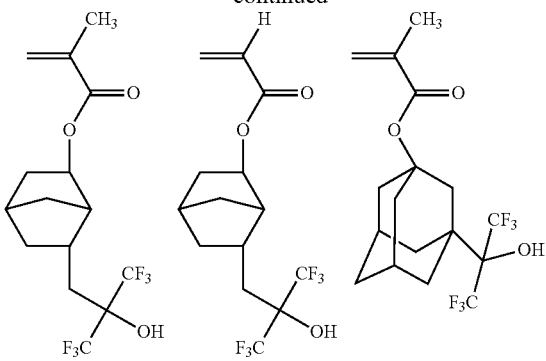
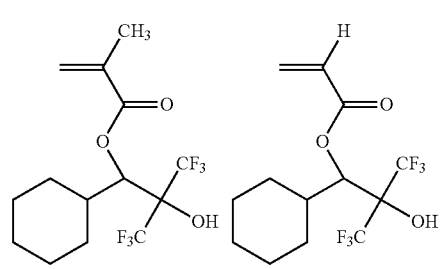
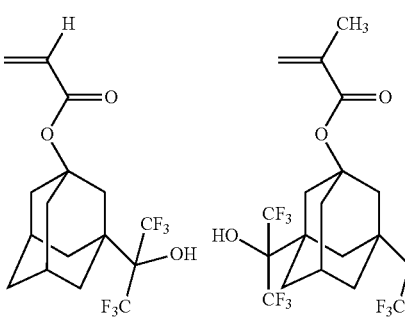
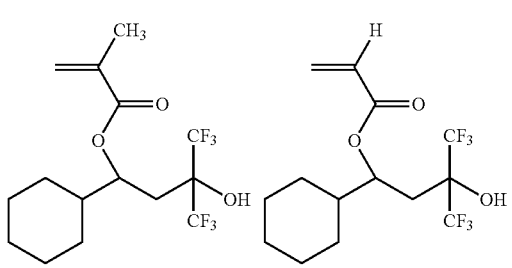
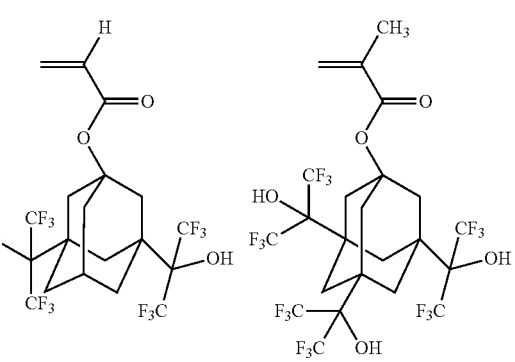
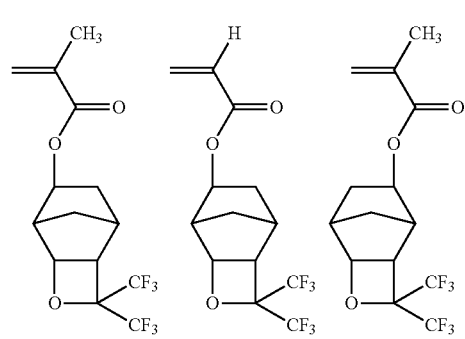
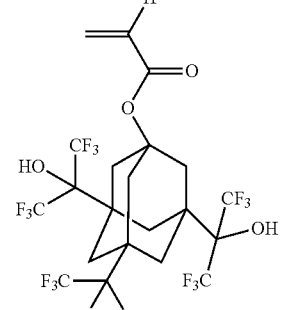
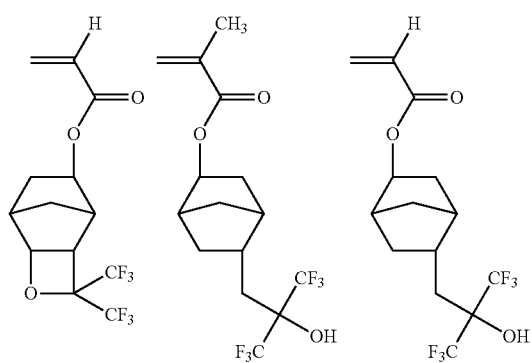
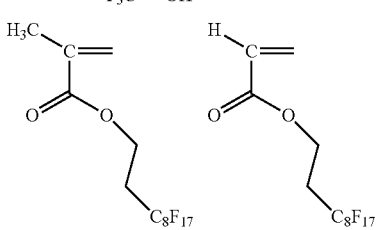

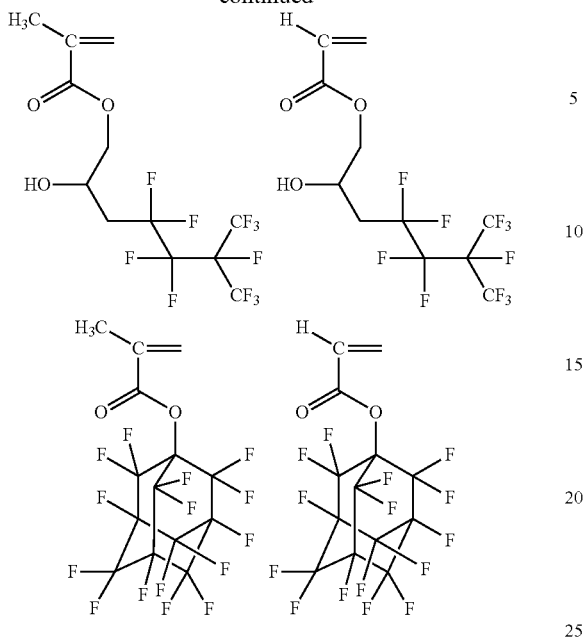

The content of the structural unit derived from the monomer having the acid-labile group in the resin may be generally adjusted to 10 to 80 mol % with respect to the total structural units constituting the resin.

When the structural unit derived from a 2-alkyl-2-adamantyl(meth)acrylate or a 1-(1-adamantyl)-1-alkylalkyl(meth)acrylate is included as the structural unit derived from the monomer with the acid-labile group, adjusting the content to about 15 mol % or more with respect to the total structural units, which is advantageous in terms of the dry etching resistance of the resulting resist.

The weight average molecular weight of the resin is preferably 2500 to 100,000, more preferably 2700 to 50000, and even more preferably 3000 to 40000. The weight average molecular weight is a value determined by gel permeation chromatography using polystyrene as the standard product. The detailed condition of this analysis is described in Examples.

The content of the structural unit derived from the compound represented by the formula (A) in the resin is preferably 5 to 95 weight %, and more preferably 10 to 90 weight % with respect to the total structural units constituting the resin.

Examples of the resin include a resin having structural unit of B1 to structural unit of B 24 below.

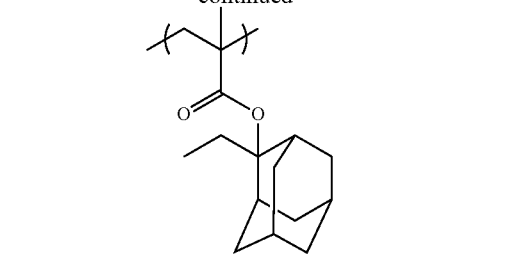

(B2)

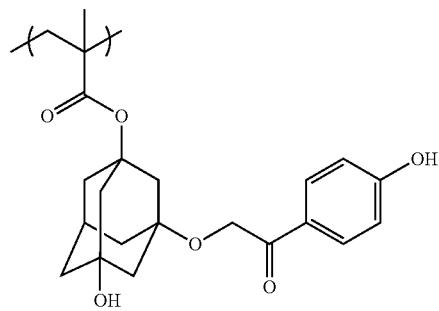

(B3)

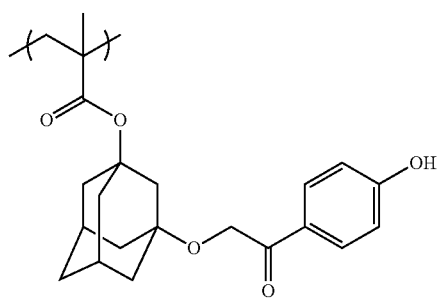

(B1)

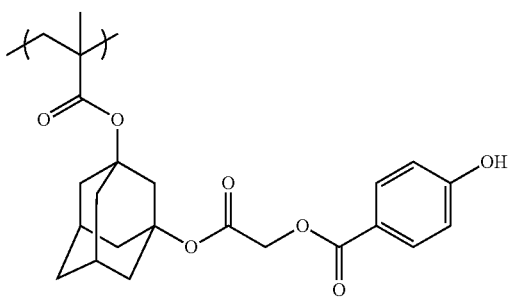

(B4)

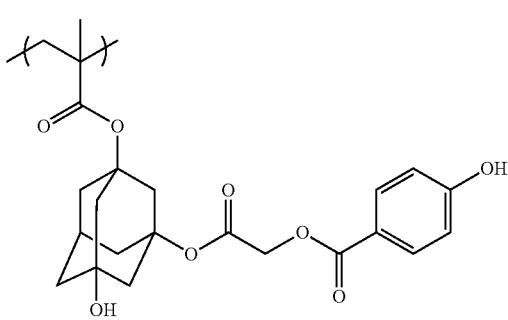

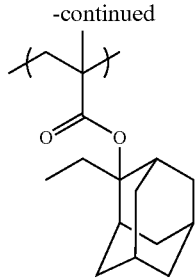
(B5)
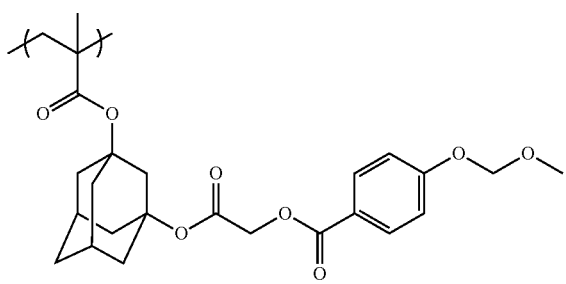
(B6)
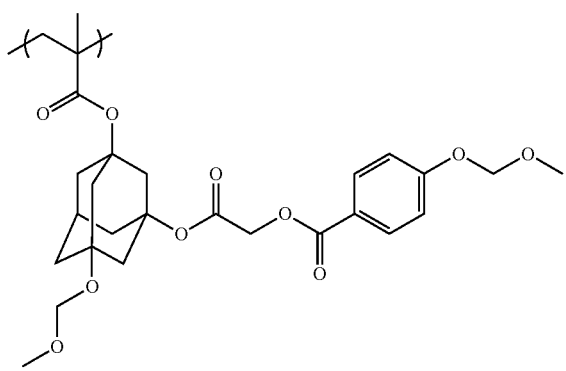
(B7)
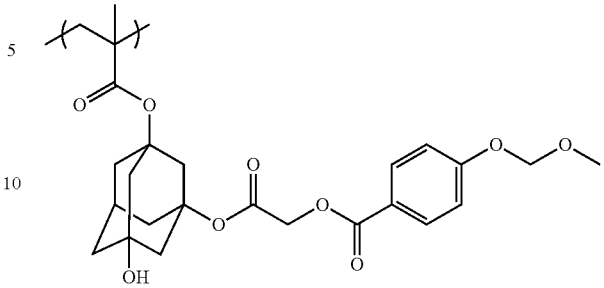
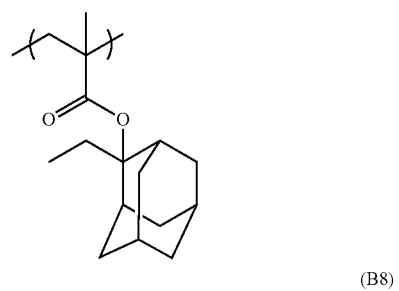
(B8)
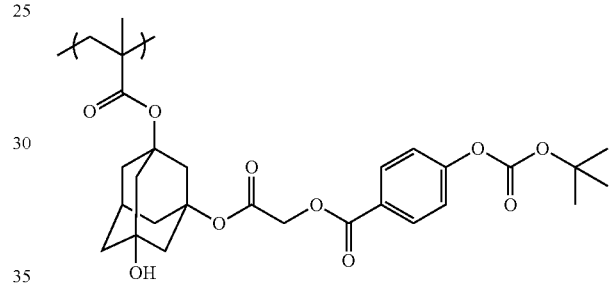
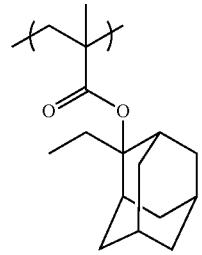
(B9)
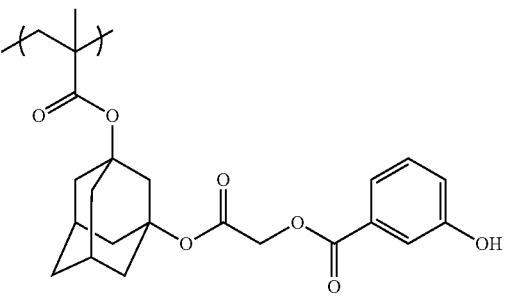
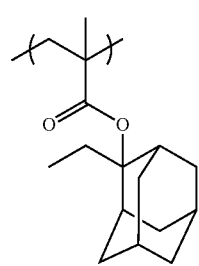
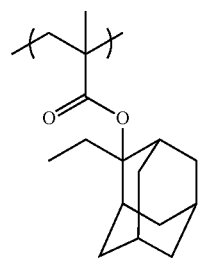
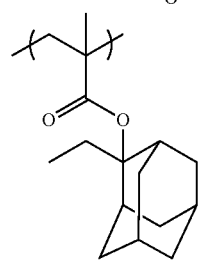

(B10)
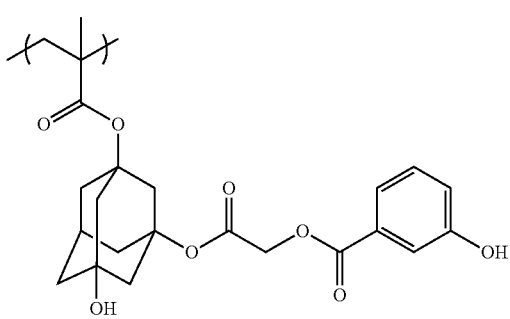
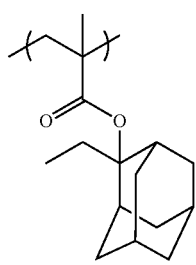
(B11)
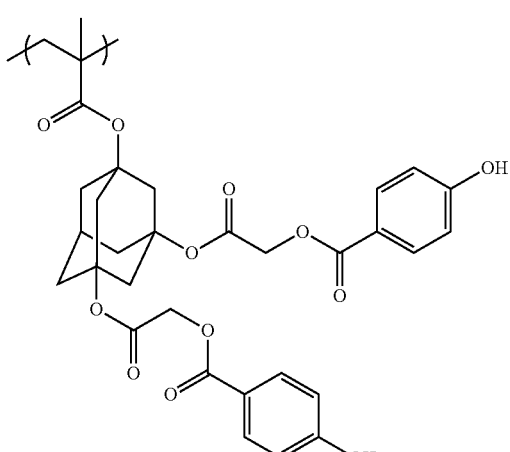
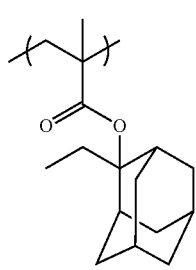
(B12)
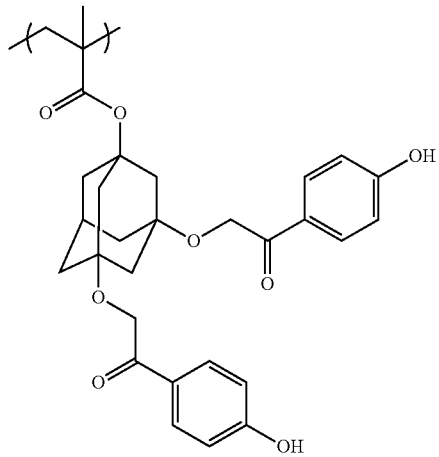
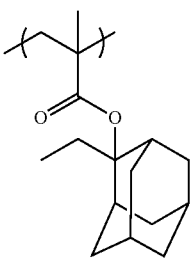
(B13)
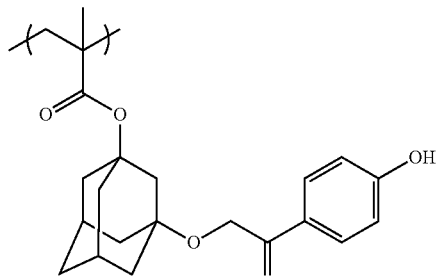
(B14)

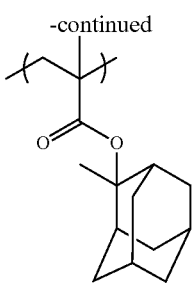
(B15)
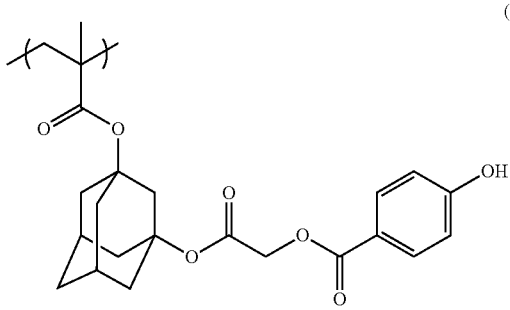
(B16)
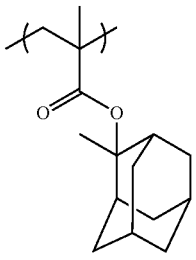
(B17)
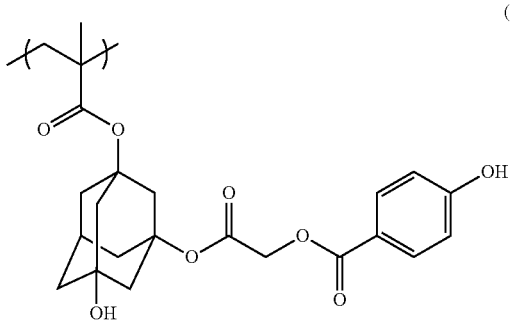
(B18)
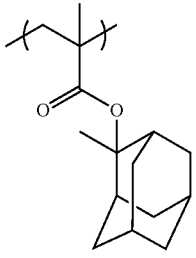
(B19)
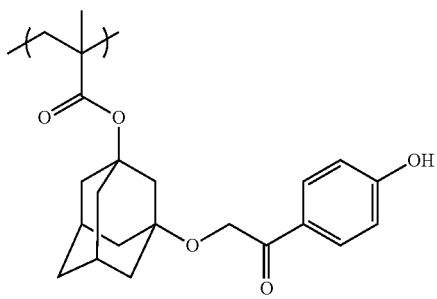
(B20)
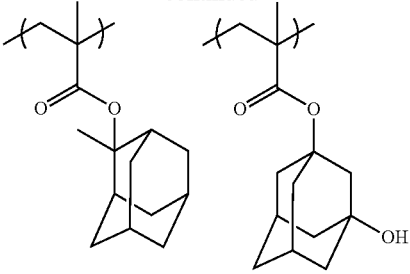
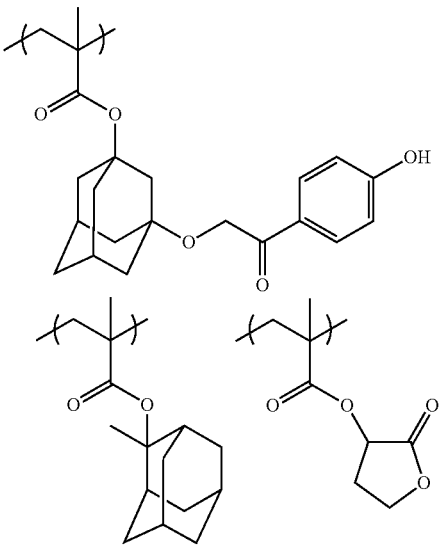
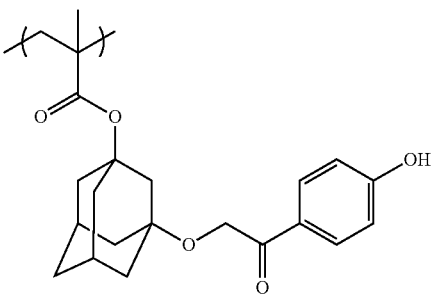
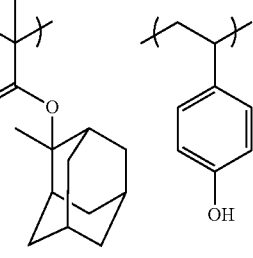
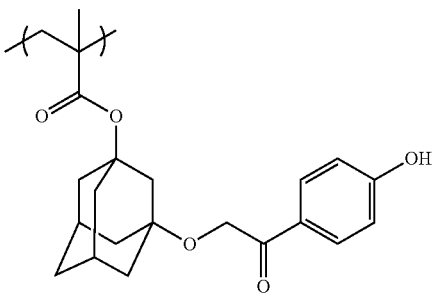

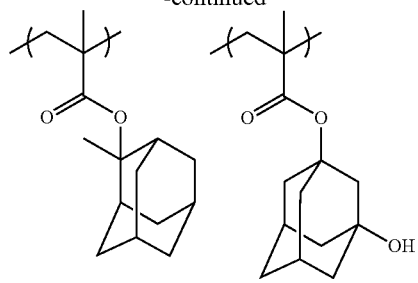
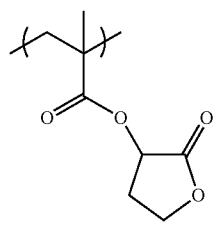
(B21)
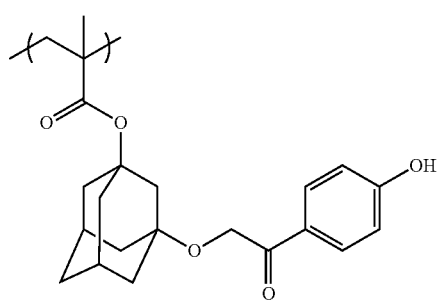
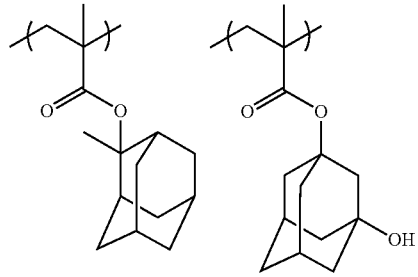
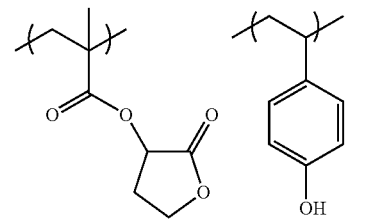
(B22)
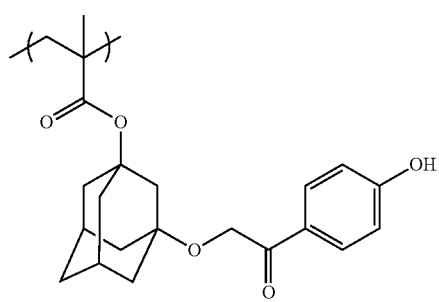
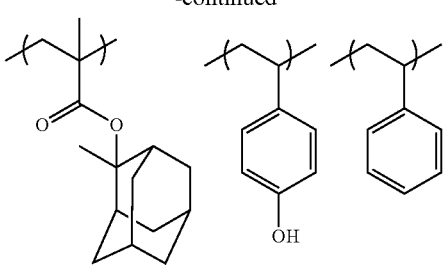
(B23)
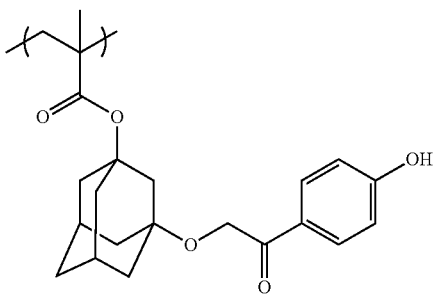
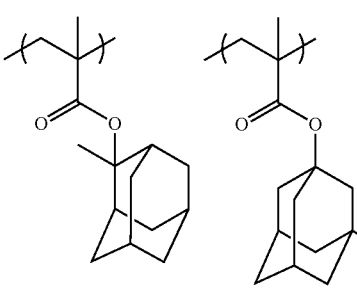
(B24)
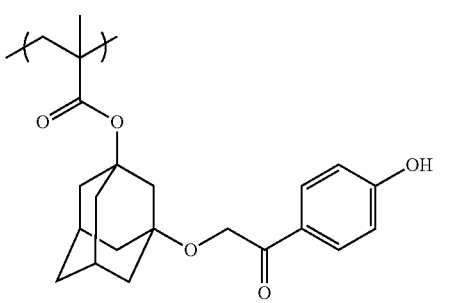
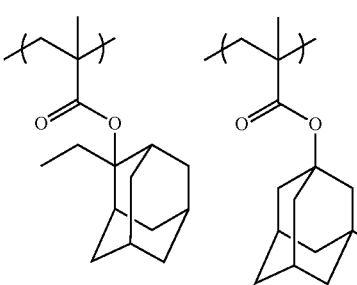

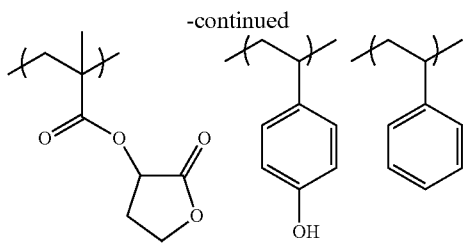

A resist composition of the present invention includes the resin described above and an acid generator.

Examples of the acid generator include a diazonium salt, a phosphonium salt, a sulfonium salt, an iodonium salt, an imidosulfonate, an oximesulfonate, a diazodisulfone, a disulfone, an o-nitrobenzenesulfonate.

Also, examples include compounds described in U.S. Pat. No. 3,849,137-B, DE 3,914,407-B, JP-S63-26653-A, JP-S55-164824-A, JP-S62-69263-A, JP-S63-146038-A, JP-S63-163452-A, JP-S62-153853-A, JP-S63-146029 A, U.S. Pat. No. 3,779,778-B and EP 126,712-B as the acid generator.

An salt represented by the formula (I) is preferable for the acid generator.

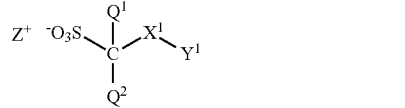

(I)

wherein $Q^1$ and $Q^2$ independently represent a fluorine atom or a $C_1$ to $C_6$ perfluoroalkyl group;

$X^2$ represents a single bond or a $C_1$ to $C_{21}$ divalent saturated hydrocarbon group, one or more —$CH_2$— contained in the saturated hydrocarbon group may be replaced by —O— or —CO— group;

$Y^1$ represents a $C_1$ to $C_{36}$ alkyl group or a $C_3$ to $C_{36}$ alicyclic hydrocarbon group, and a $C_3$ to $C_{36}$ aromatic hydrocarbon group, and the alkyl group, the alicyclic hydrocarbon group and the aromatic hydrocarbon group may be substituted, and one or more —$CH_2$-contained in the alicyclic hydrocarbon group may be replaced by —O— or —CO— group;

$Z^+$ represents an organic counter cation.

Examples of the fluoroalkyl group include perfluoromethyl, perfluoroethyl, perfluoro-n-propyl, perfluoro-isopropyl, perfluoro-n-butyl, perfluoro-sec-butyl, perfluoro-tert-butyl, perfluoro-n-pentyl and perfluoro-n-hexyl groups. Among these, perfluoromethyl group is preferable.

Examples of the divalent saturated hydrocarbon group include a group including an alkylene group or a cycloalkylene group.

Examples of the alkylene group include methylene, dimethylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, hexadecamethylene, heptadecamethylene, ethylene, propylene, isopuropylene, sec-buthylene and tert-buthylene groups.

Examples of the cycloalkylene group include cyclopropylene, cyclobuthylene, cyclopenthylene, cyclohexylene, methyl cyclohexylene, dimethyl cyclohexylene, cycloheptylene and cyclooctylene groups.

For an anion of the salt represented by the formula (I) (herein after preferred to as "salt (I)"), $Q^1$ and $Q^2$ independently are preferably perfluoromethyl or fluorine atom, and more preferably fluorine atom Examples of the $X^2$ are suitably —CO—O—$X^{10}$—, —CO—O—$X^{11}$—CO—O—, —$X^{11}$—O—CO— and —$X^{11}$—O—$X^{12}$—, and preferably —CO—O—$X^{10}$— and —CO—O—$X^{11}$—CO—O—.

$X^{10}$, $X^{11}$ and $X^{12}$ independently represent a single bond or a $C_1$ to $C_{15}$ alkylene group.

$Y^1$ is suitably a $C_4$ to $C_{36}$ alicyclic hydrocarbon group which may be substituted.

Examples of the substituent of the optionally substituted the alkyl group, the alicyclic hydrocarbon group and the aromatic hydrocarbon group of $Y^1$ include a halogen atom, a hydroxy group, a $C_1$ to $C_{12}$ alkyl group, a $C_6$ to $C_{20}$ aromatic hydrocarbon group, a $C_7$ to $C_{21}$ aralkyl group, a glycidyloxy group and a $C_2$ to $C_4$ acyl group.

Examples of the anion of the salt represented by the formula (I) include the following anions represented by the formulae (IA), (IB), (IC) and (ID). Among these, the anion represented by the formula (IA) and the formula (IB) are suitable.

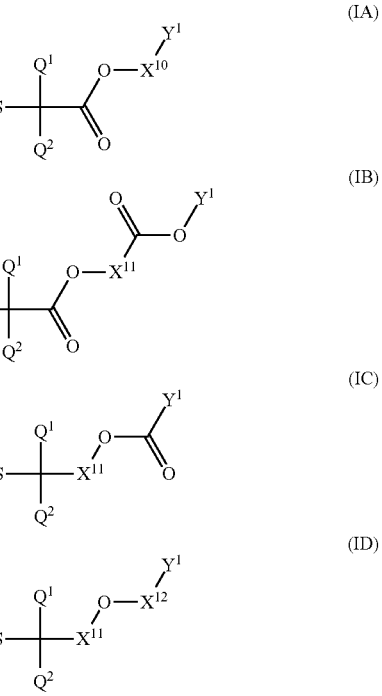

Wherein $Q^1$, $Q^2$, $Y^1$ $X^{10}$, $X^{11}$ and $X^{12}$ represent the same meaning as defined above.

Examples of $Y^1$ include a group represented by the formula (W1) to the formula (W26). Among these, groups represented by the formula (W1) to the formula (W19) are preferable, and groups represented by the formula (W12), (W15), (W16) and (W19) are more preferable.

(W1)

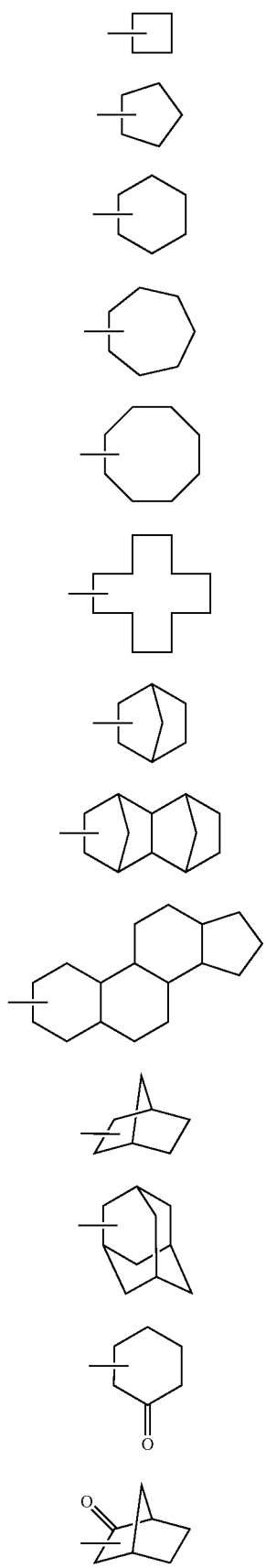
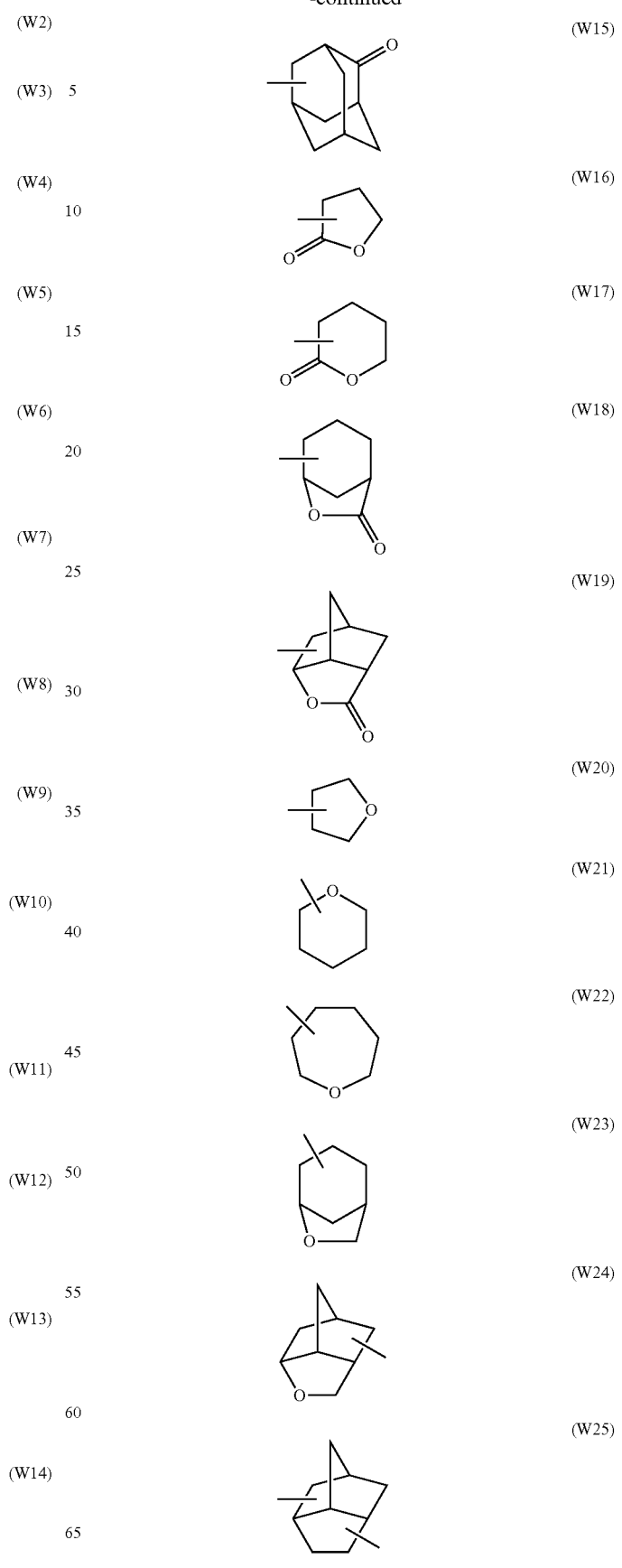

(W26)
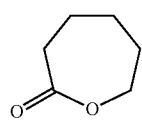
Specific examples of $Y^1$ include the groups below.
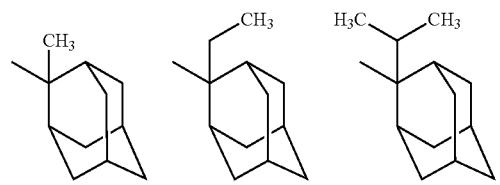
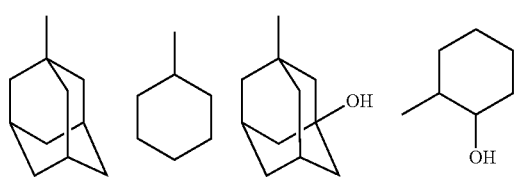
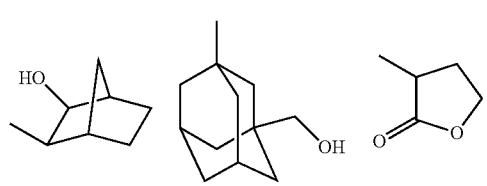
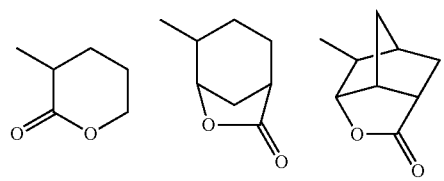
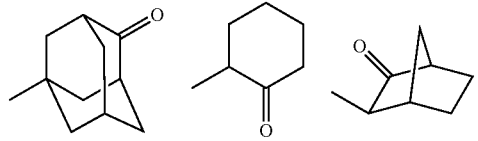
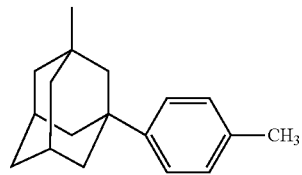
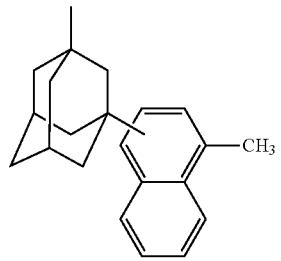
-continued
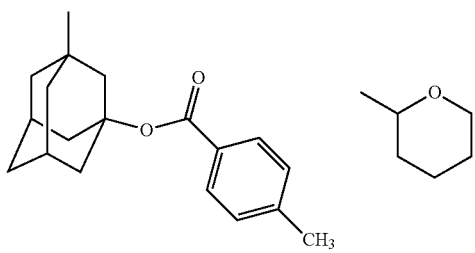
Examples of the anion include the anions below.
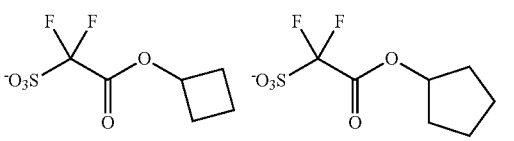
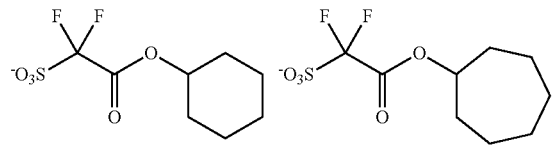
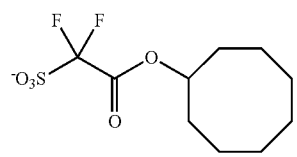
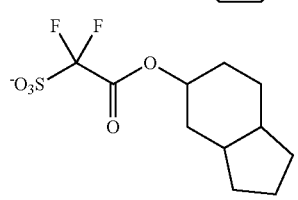
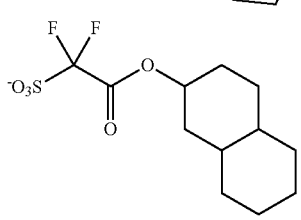
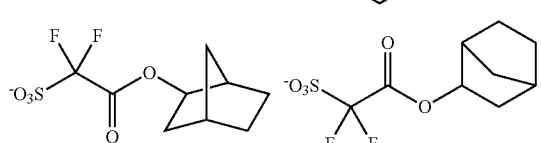
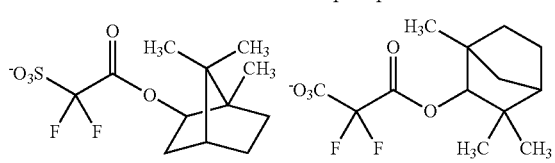
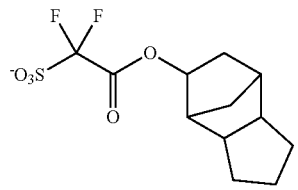

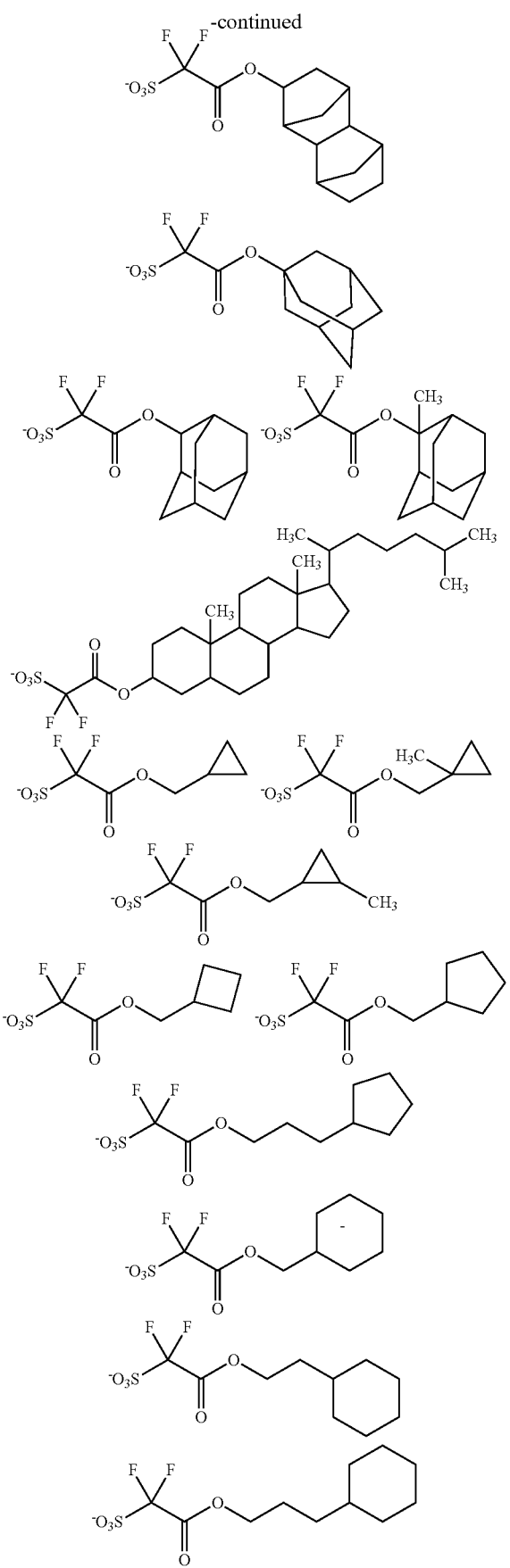
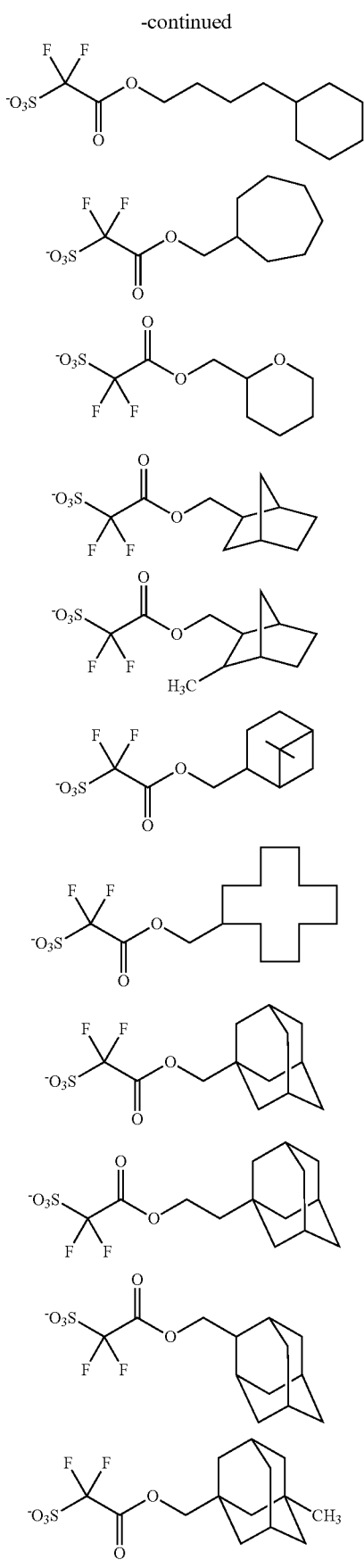

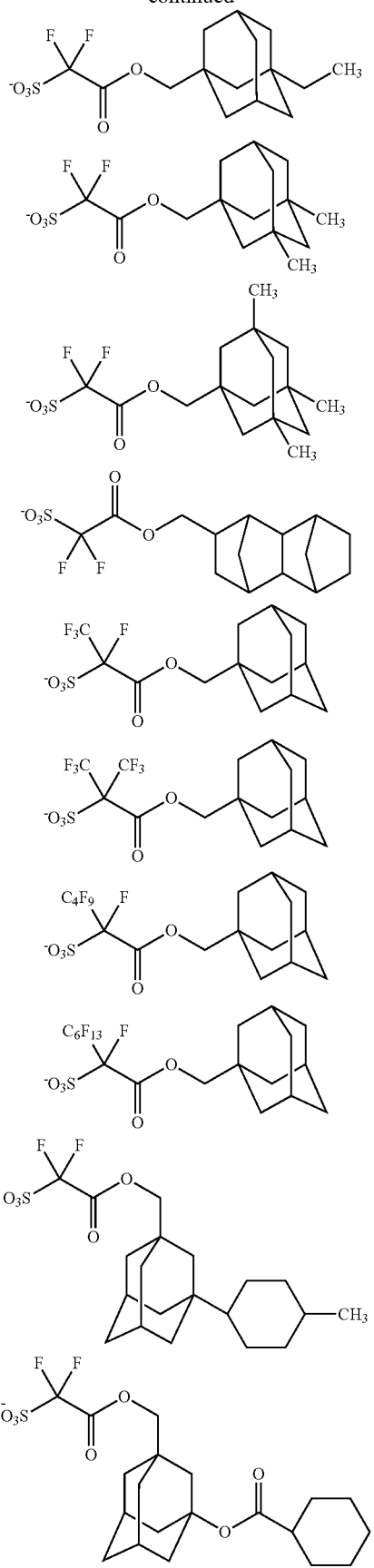
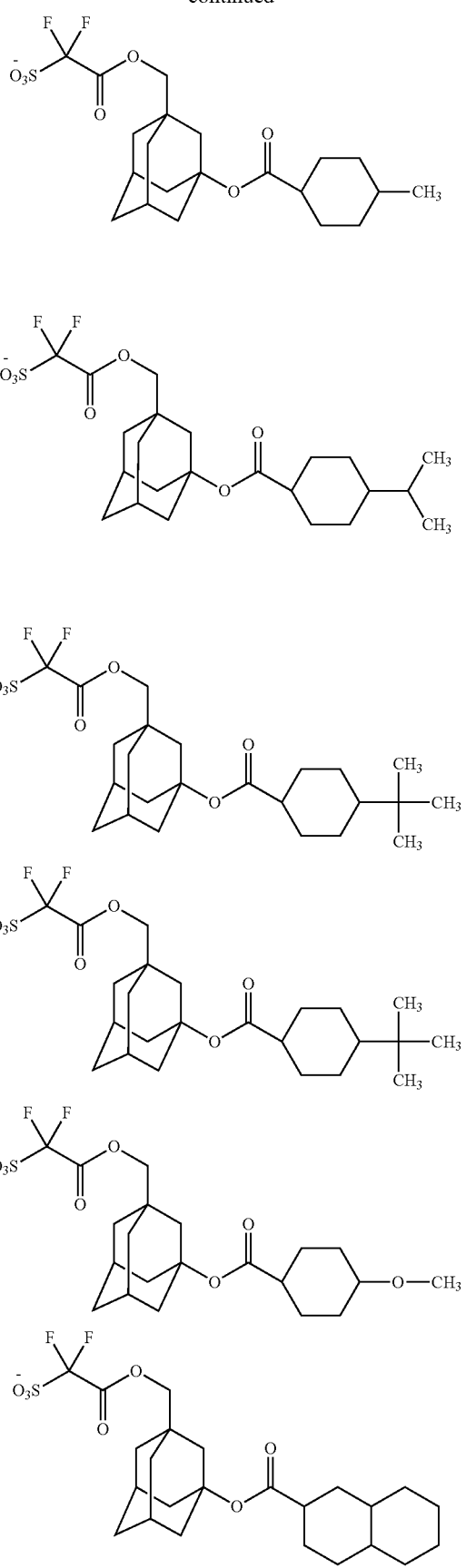

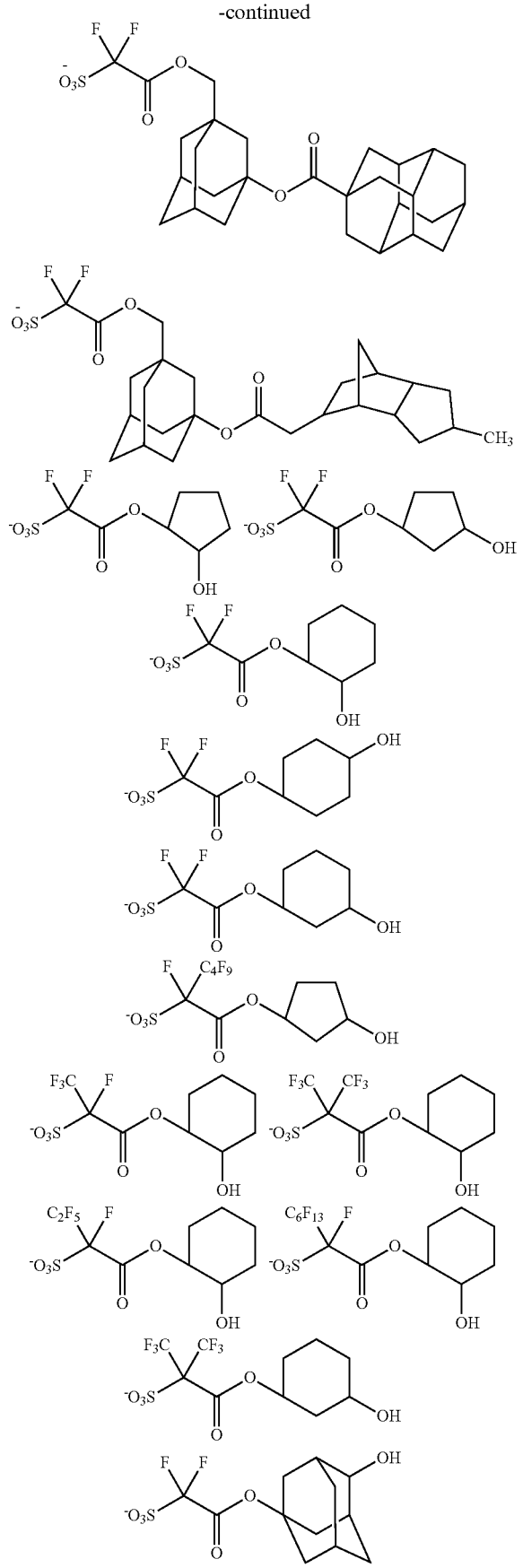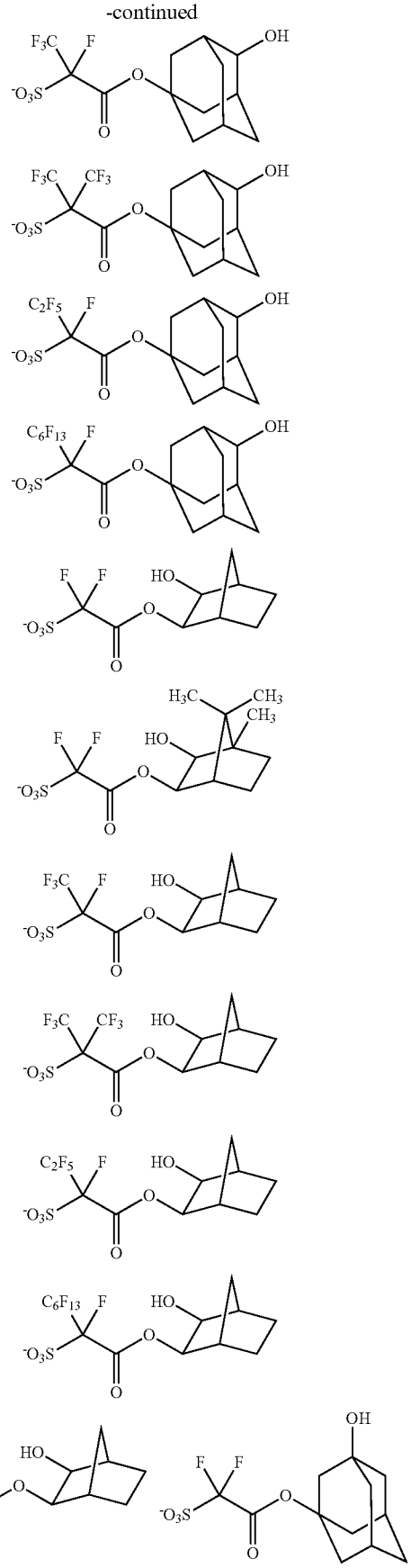

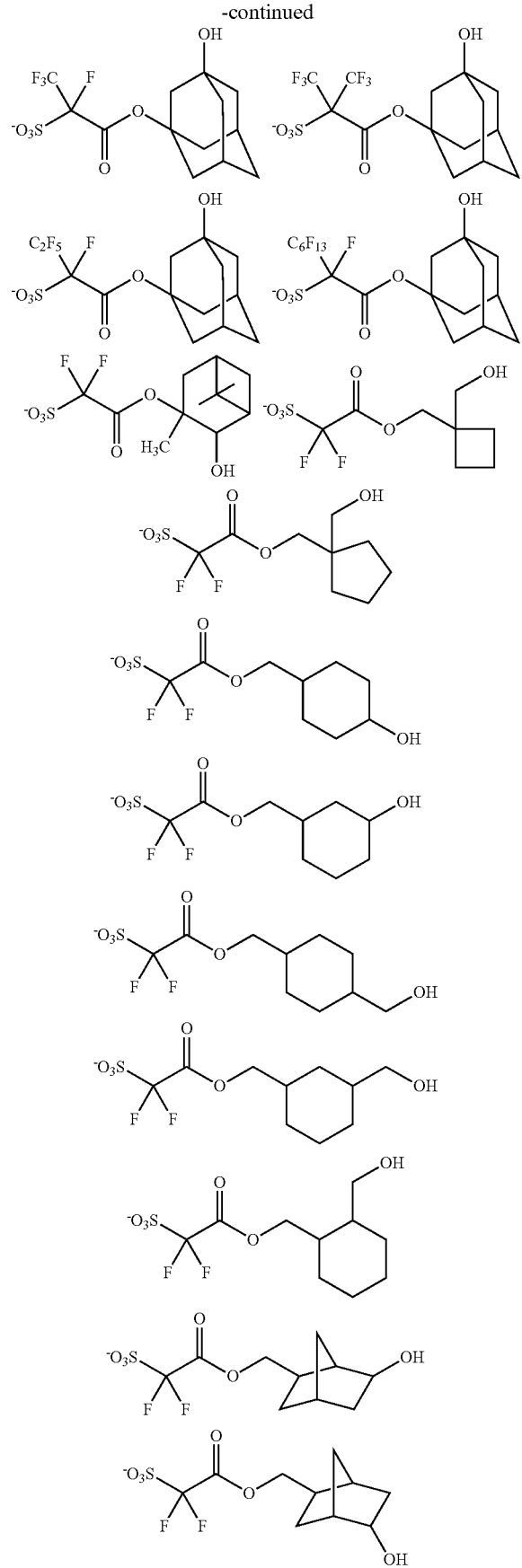
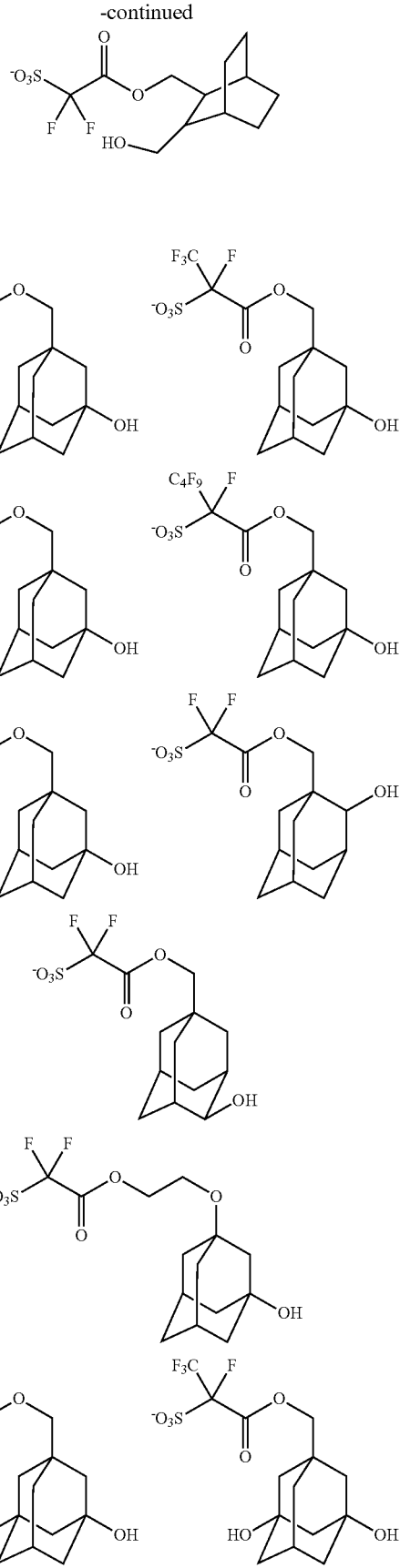

-continued
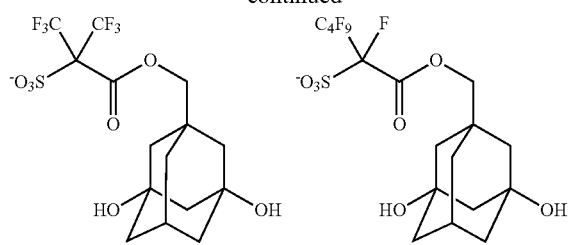
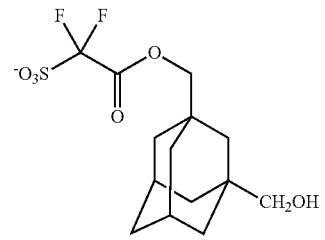
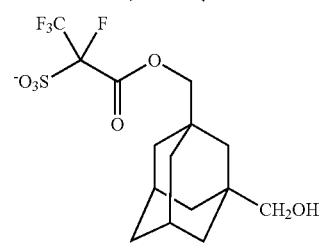
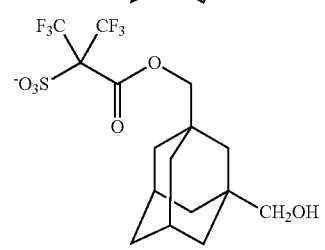
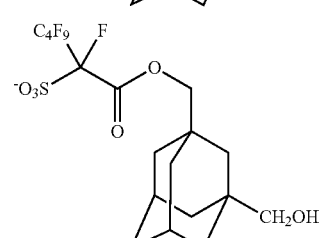
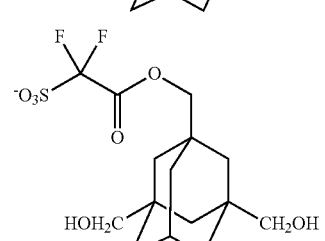
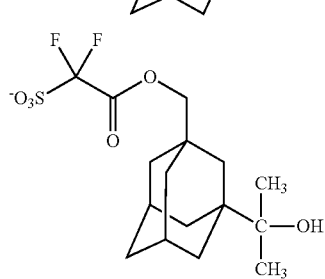
-continued
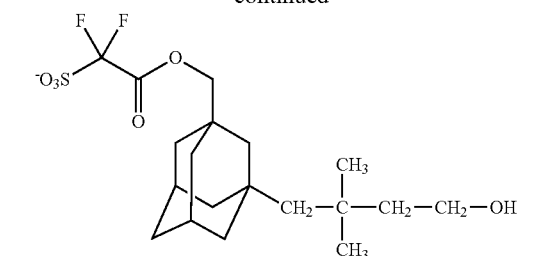
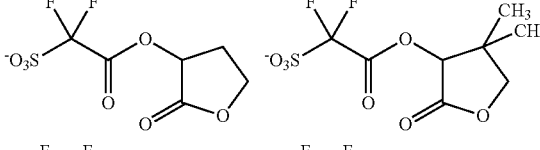
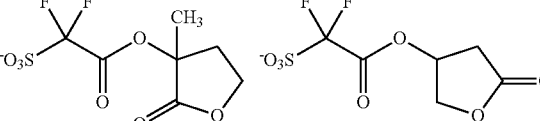
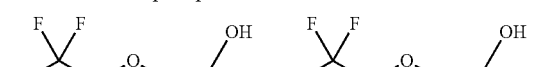
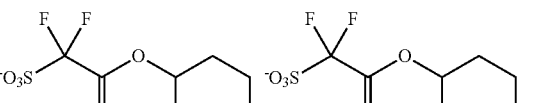
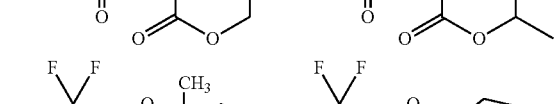
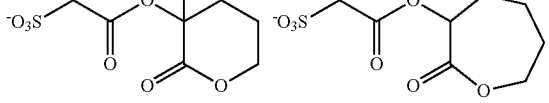
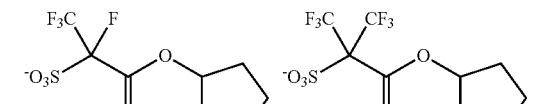
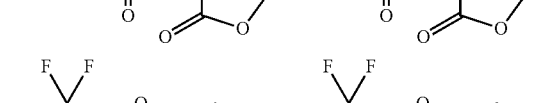
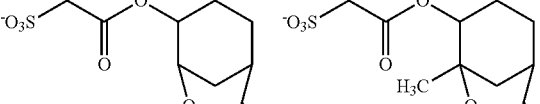
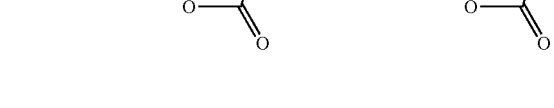

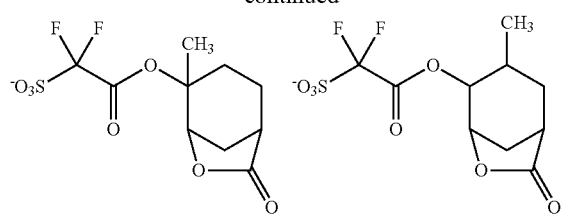
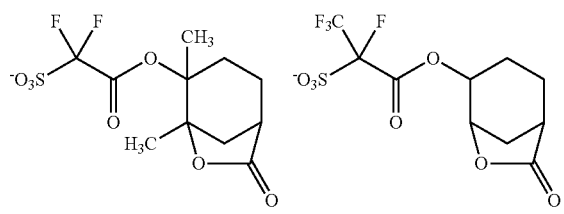
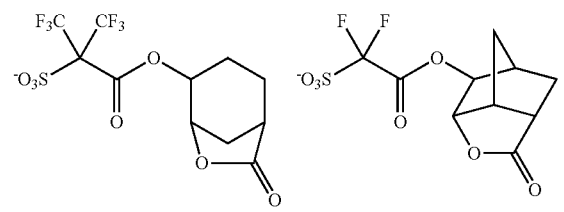
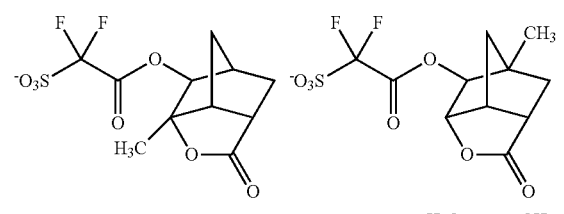
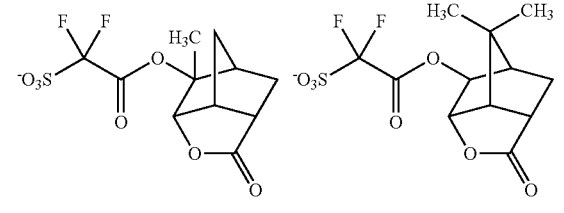
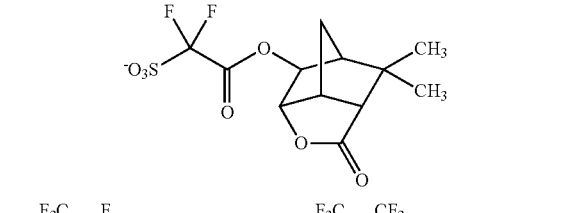
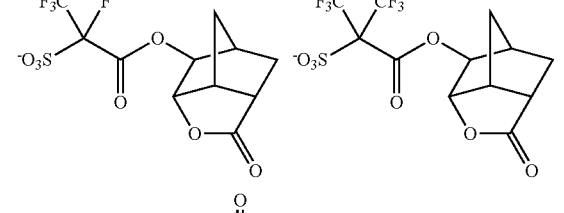
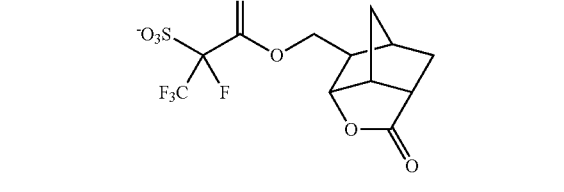
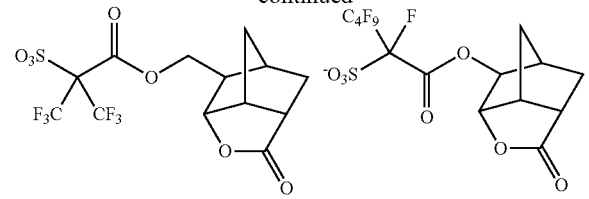
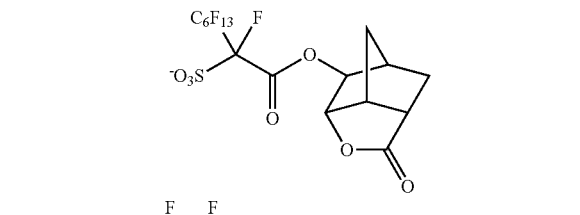
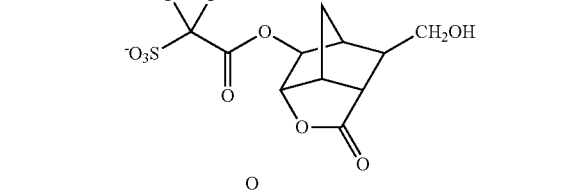
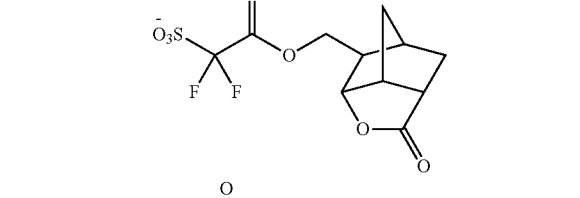
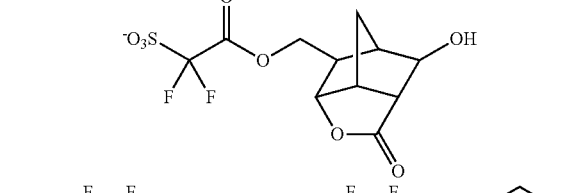
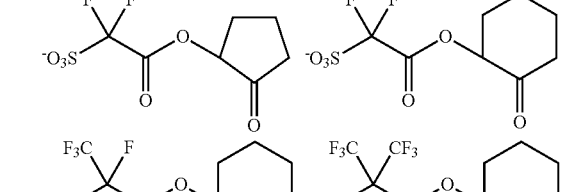
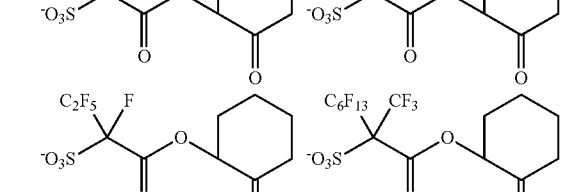
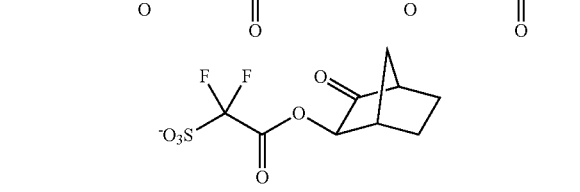
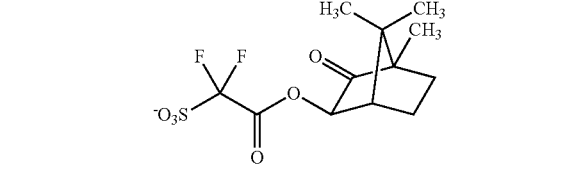

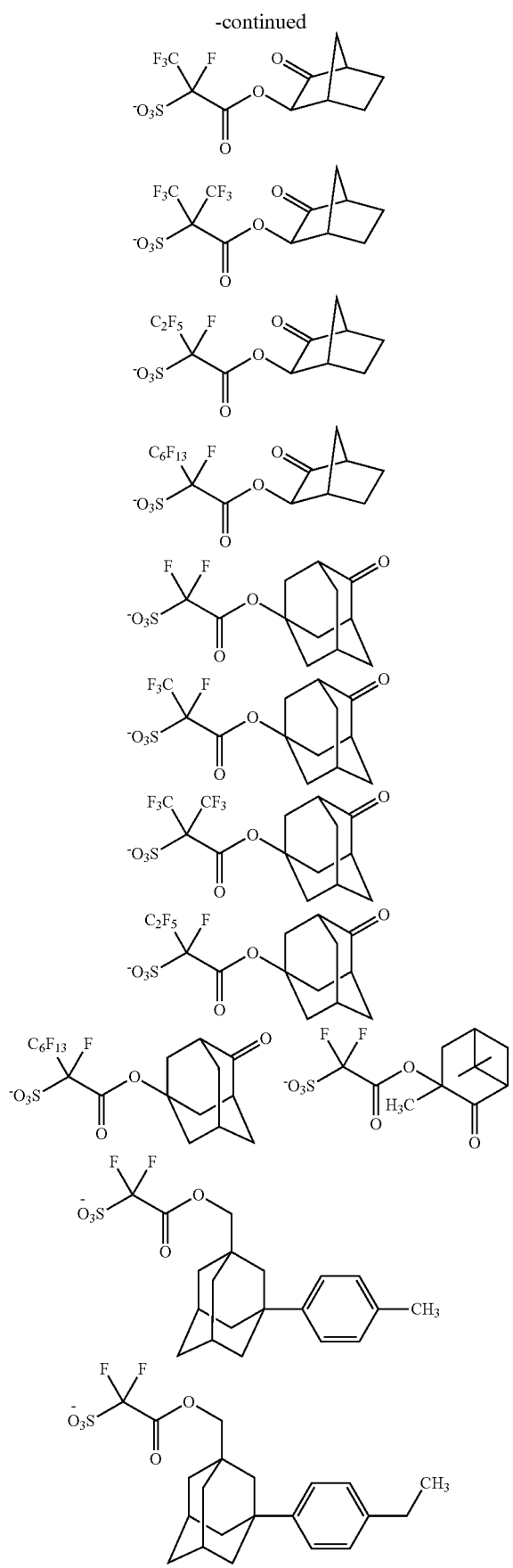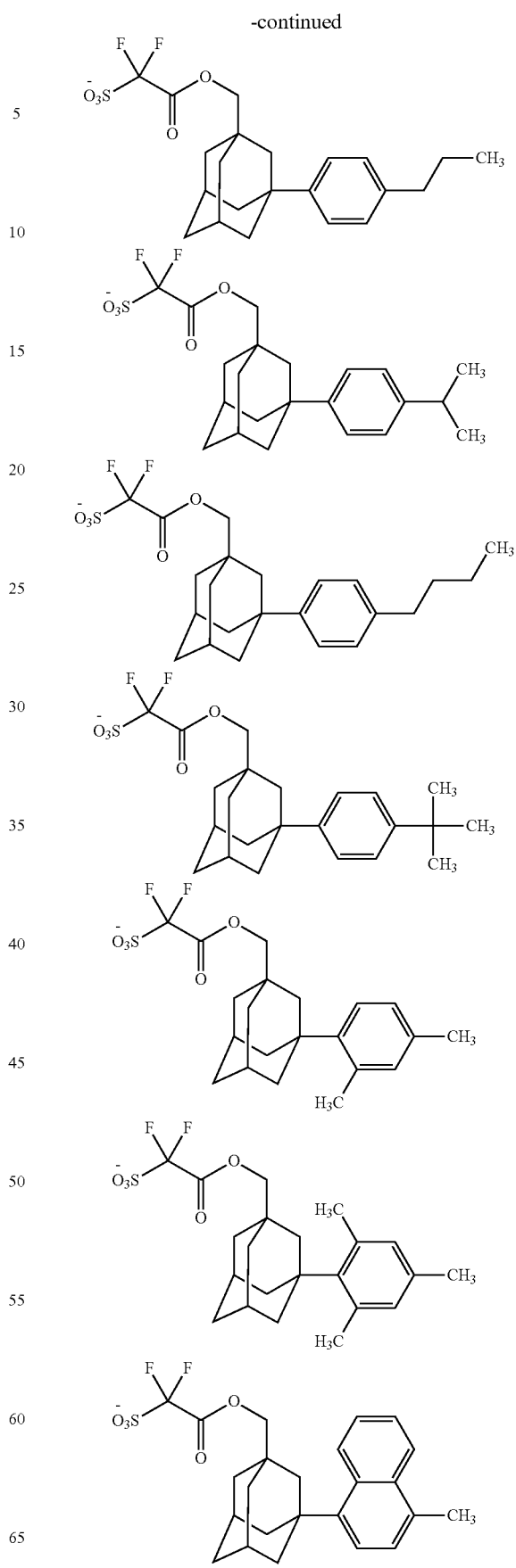

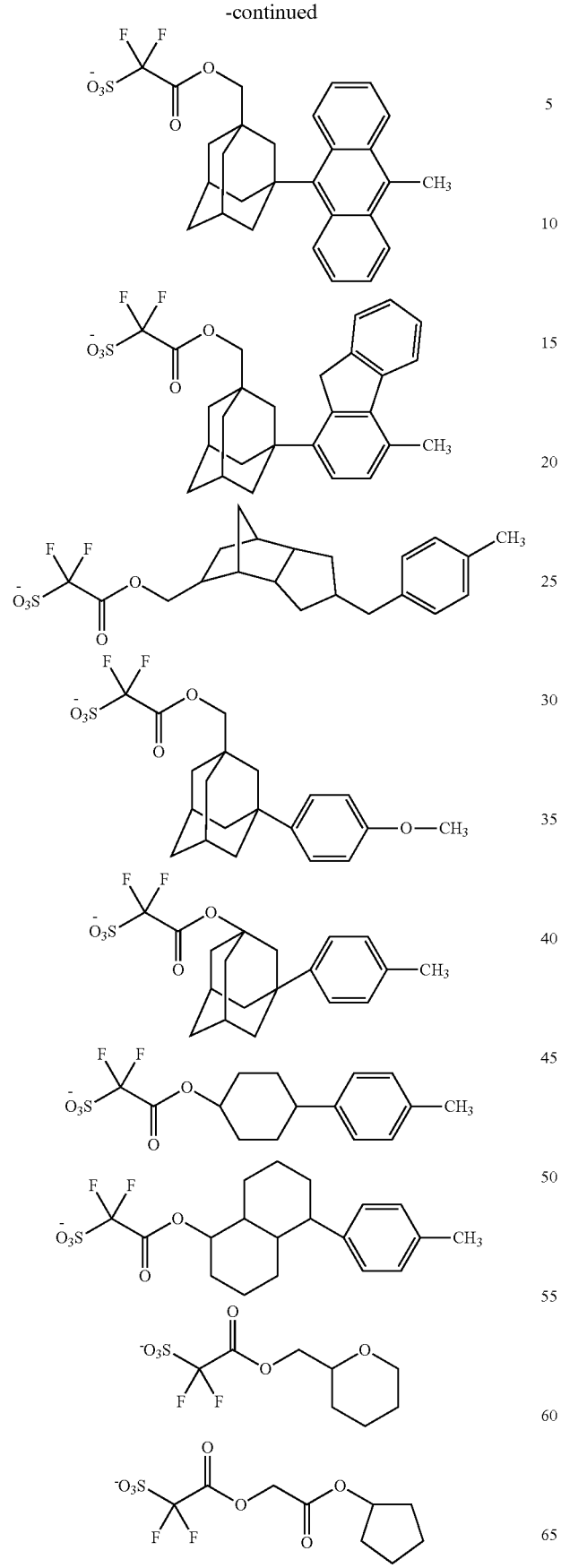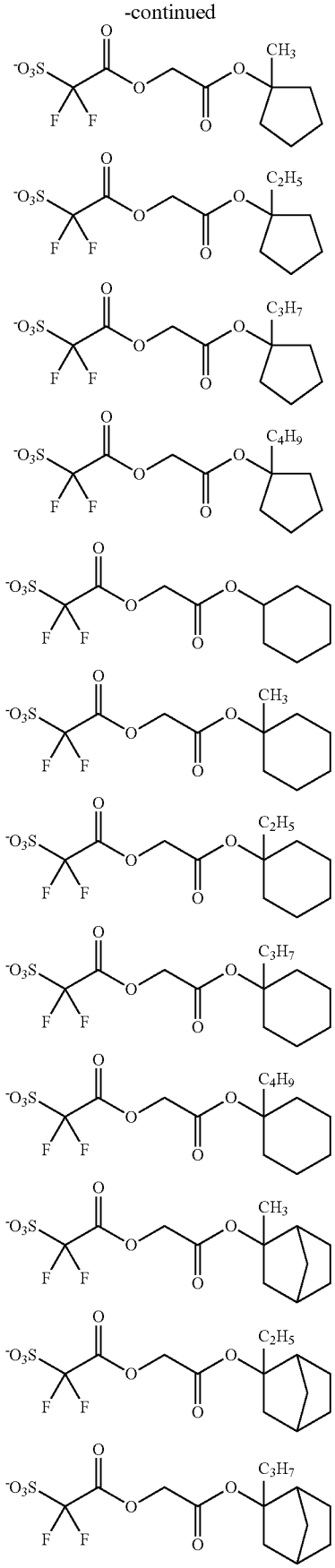

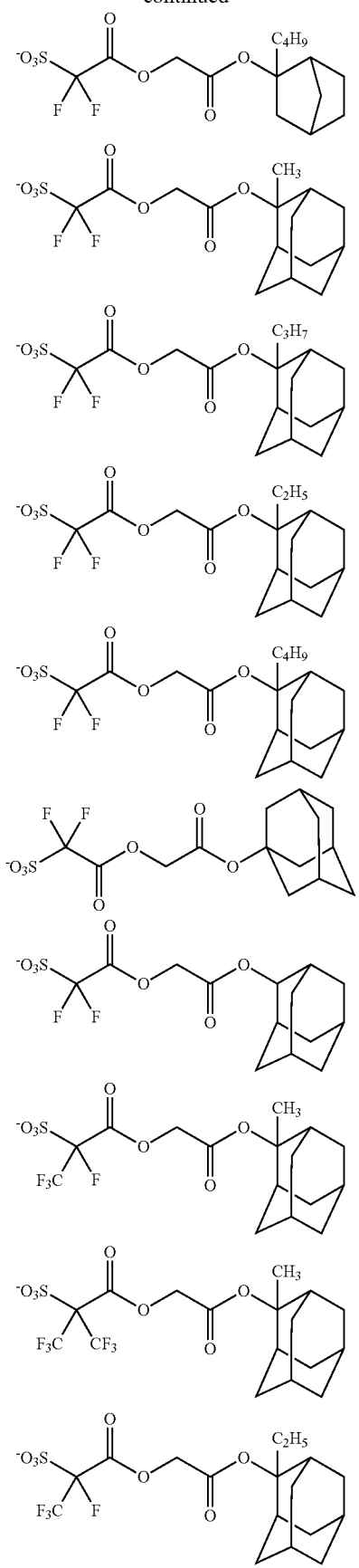
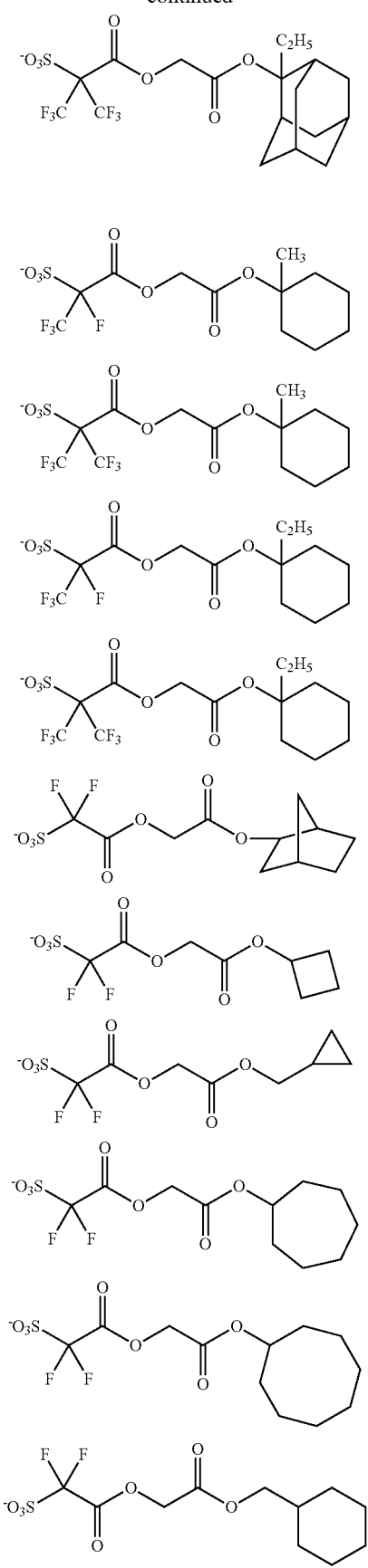

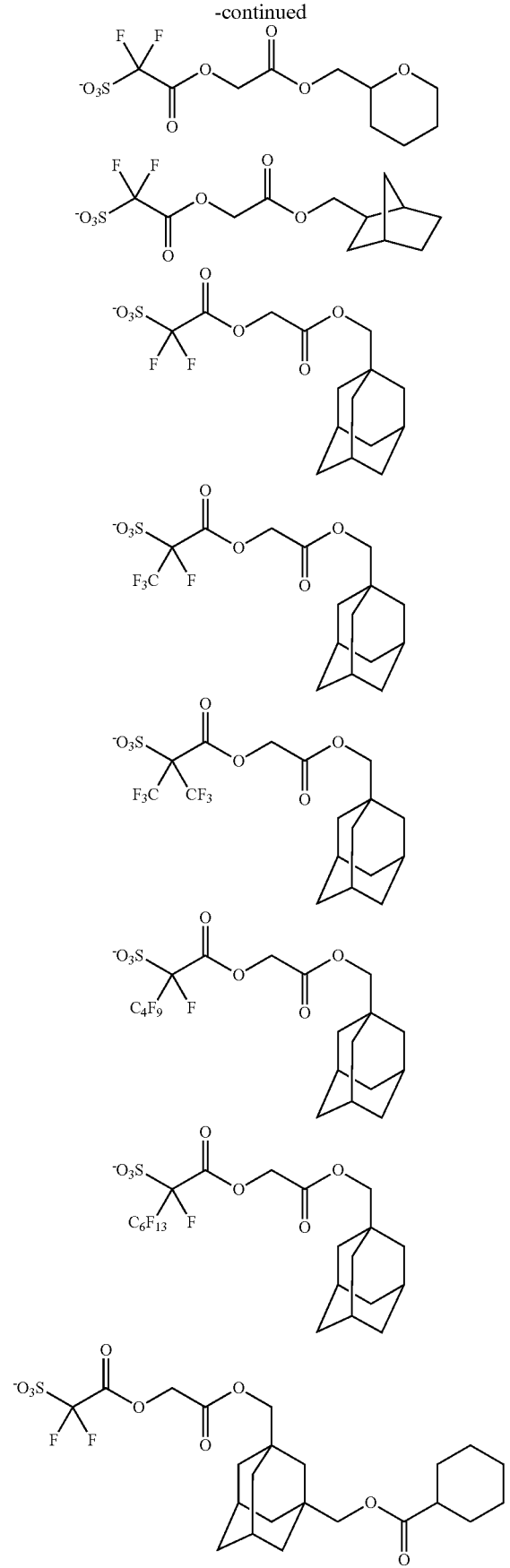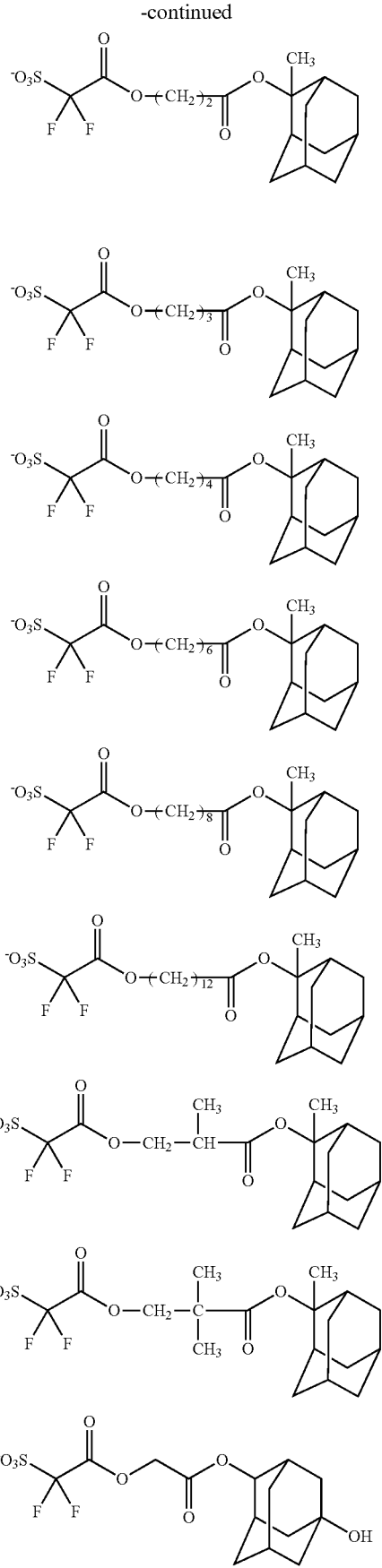

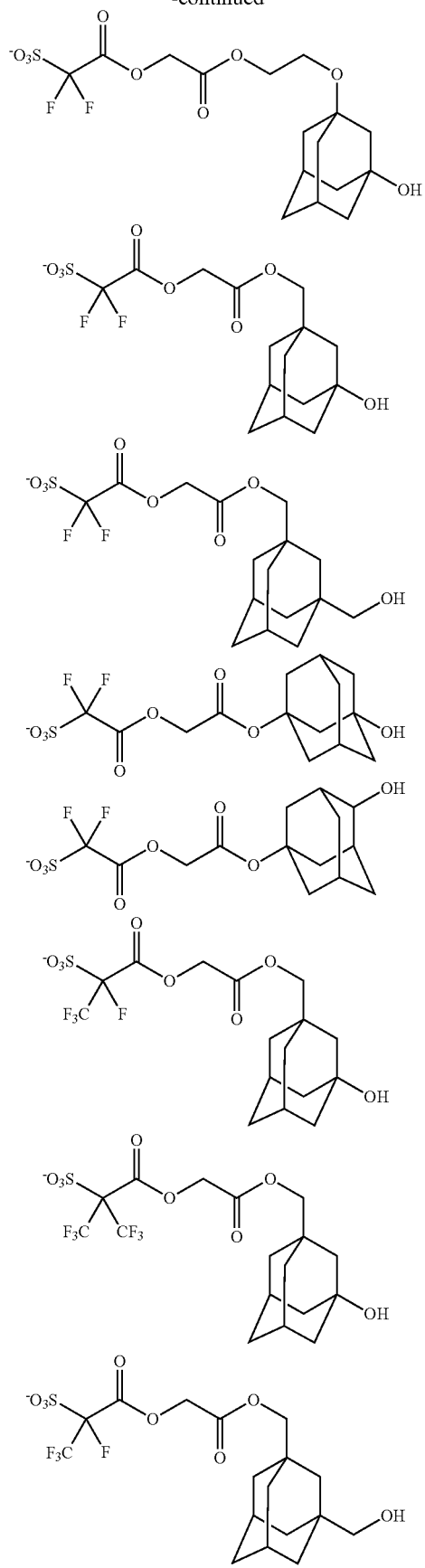
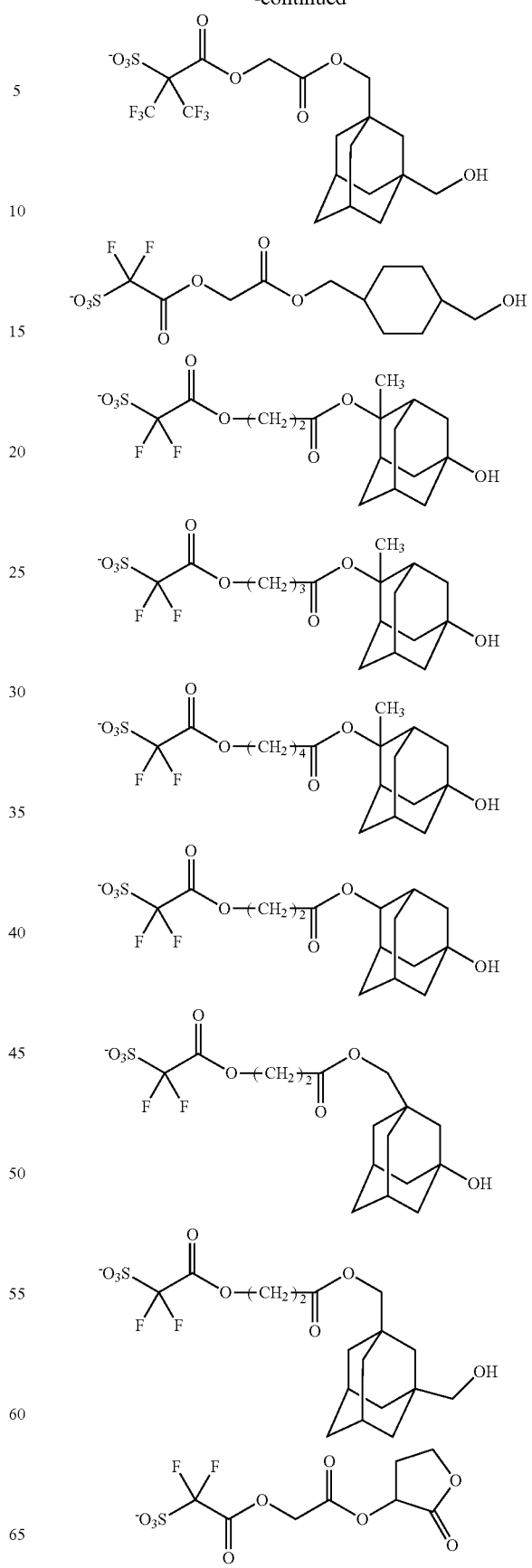

65
-continued
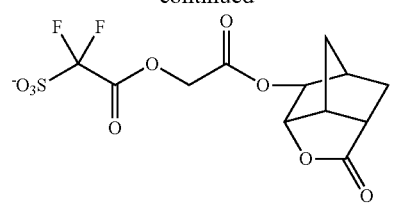
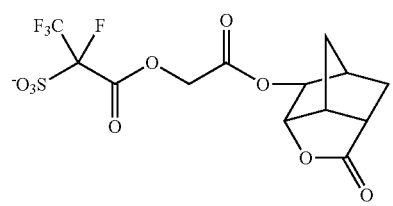
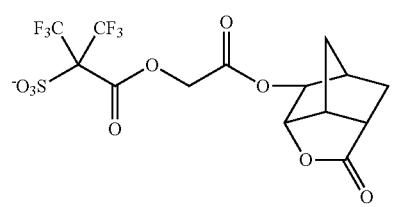
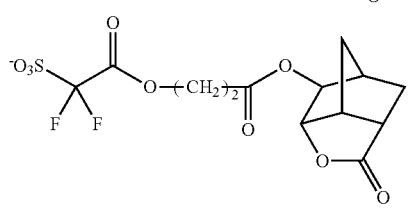
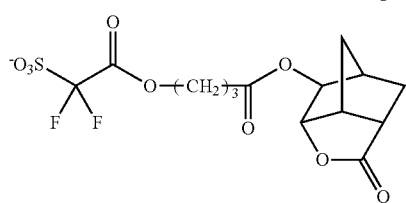
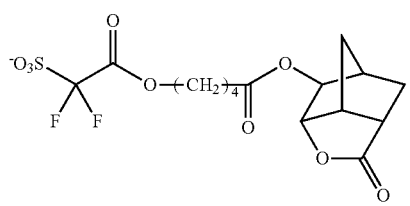
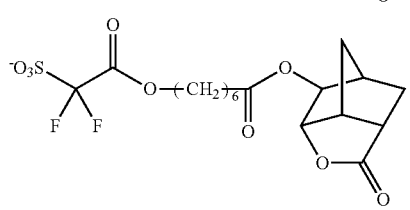
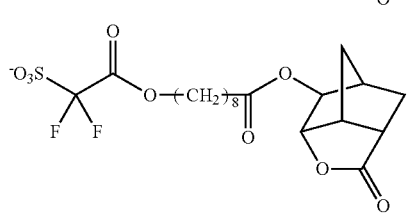
66
-continued
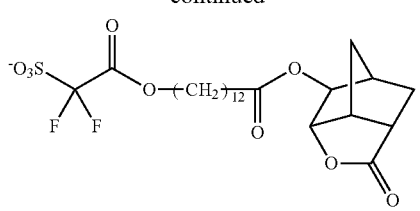
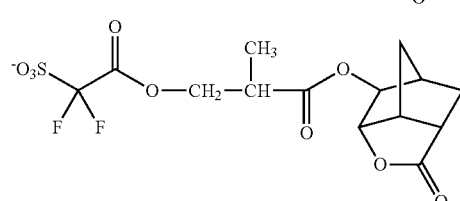
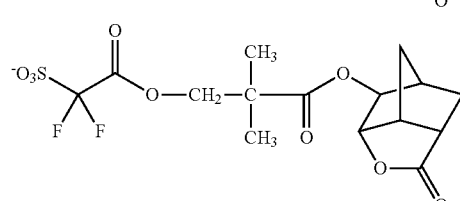
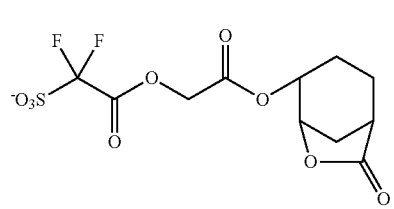
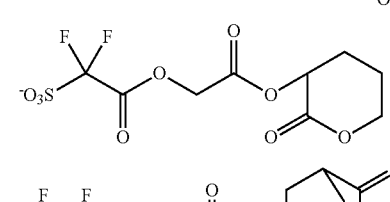
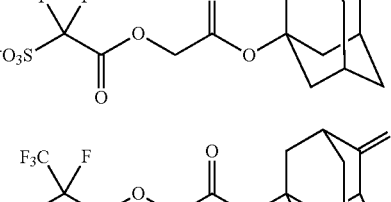
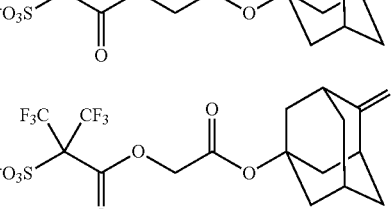
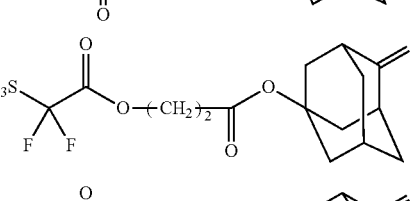
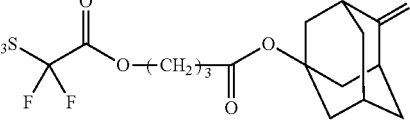

-continued
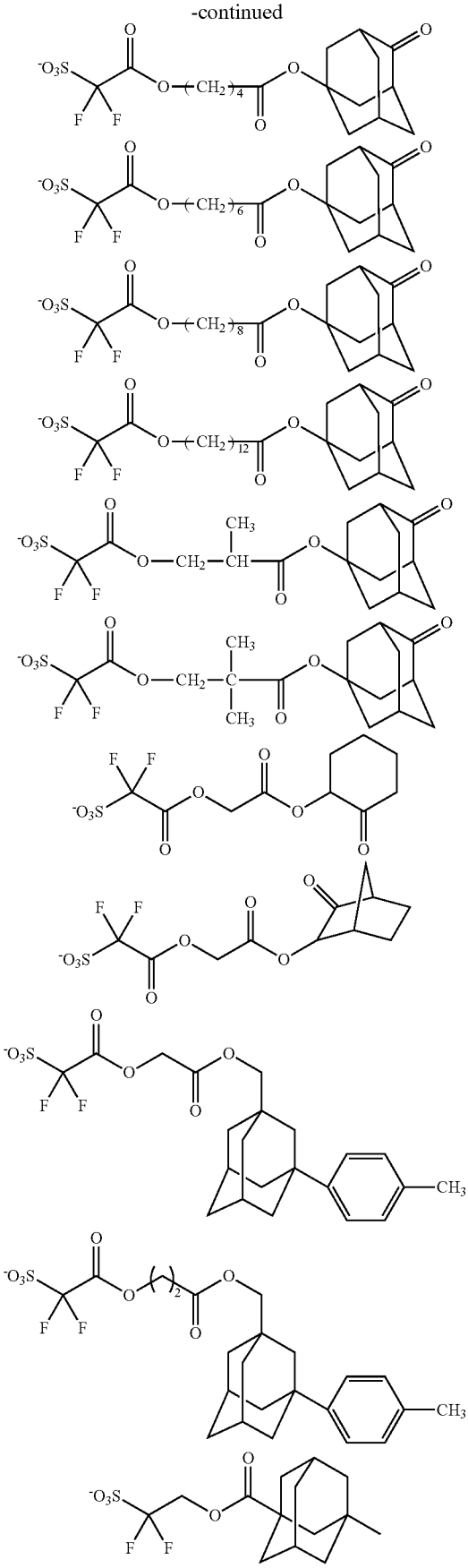
-continued
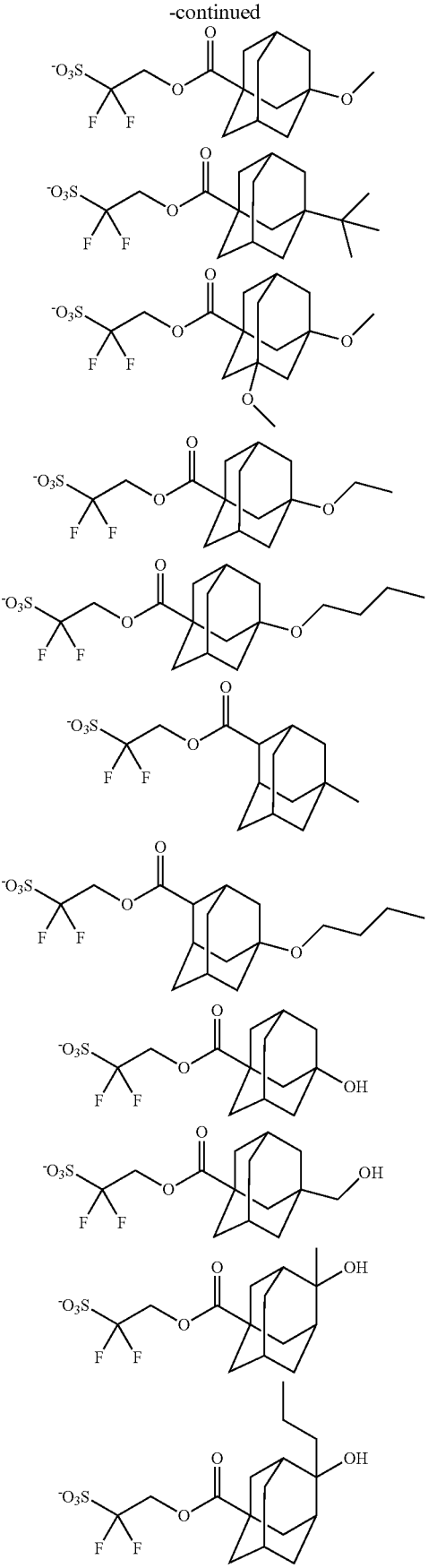

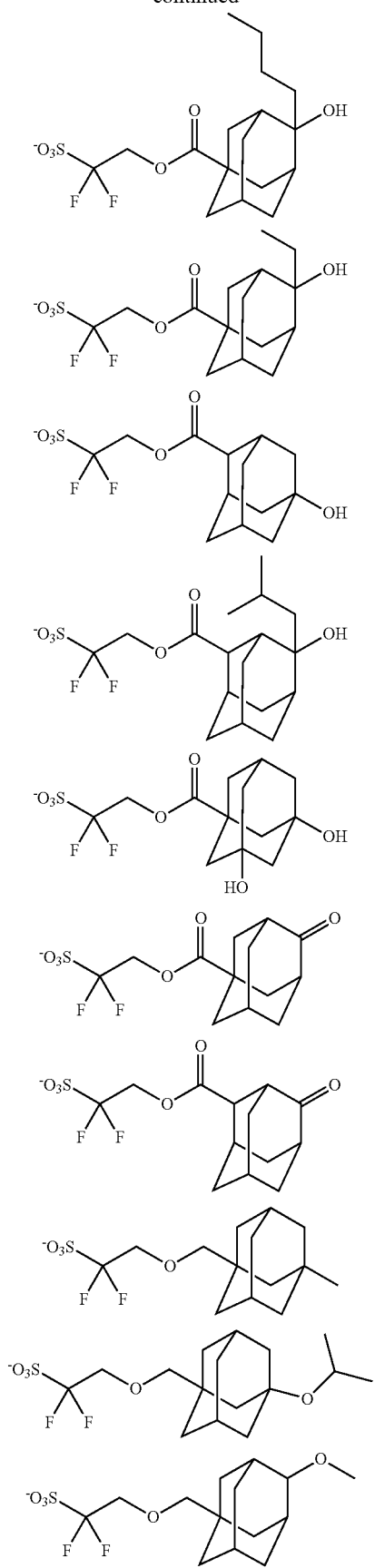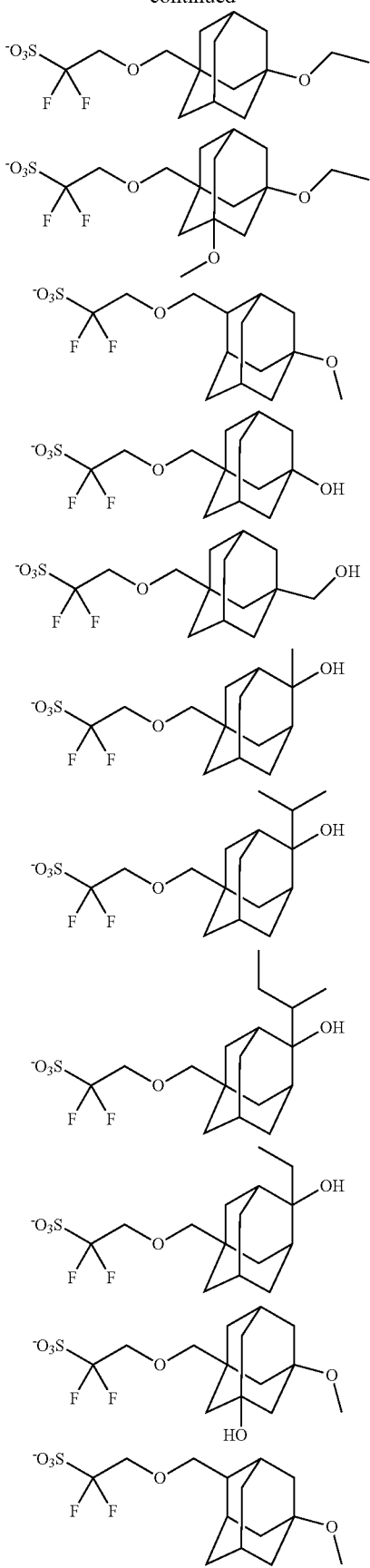

71
-continued
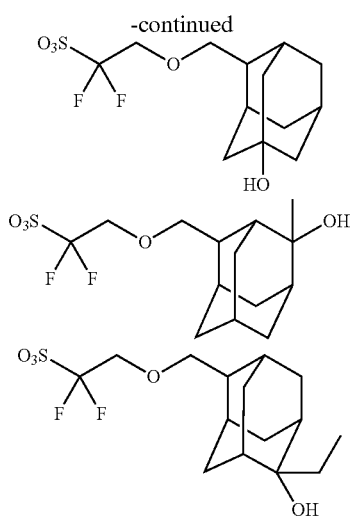
72
-continued
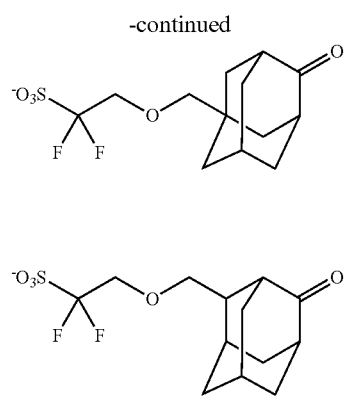
Examples of the $Z^+$ of the salt represented by the formula (I) include cations represented by the formula (IXz), the formula (IXb), the formula (IXc) and the formula (IXd).
(IXz)　　(IXb)
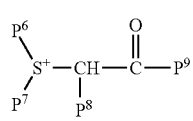
(IXc)
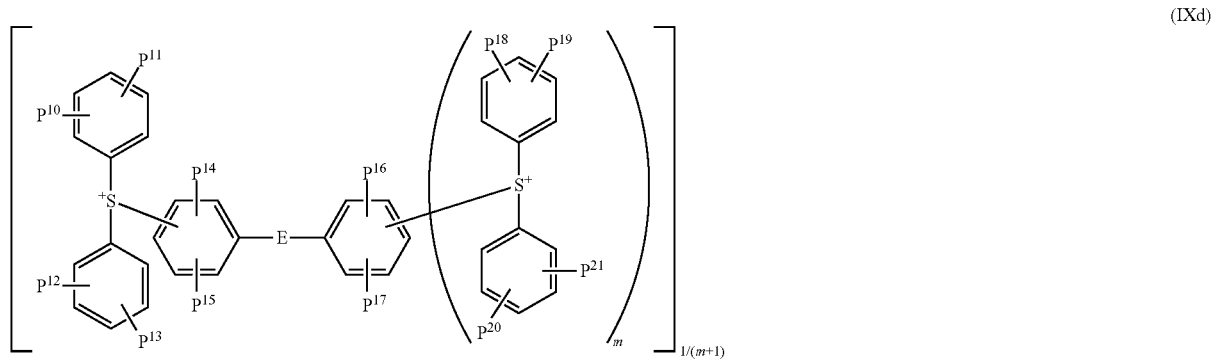
(IXd)

wherein $P^a$, $P^b$ and $P^c$ in the formula (IXz) independently represent a $C_1$ to $C_{30}$ alkyl group, a $C_3$ to $C_{30}$ alicyclic hydrocarbon group or a $C_6$ to $C_{20}$ aromatic hydrocarbon group, one or more hydrogen atoms contained in the alkyl group may be replaced by a hydroxy group, a $C_1$ to $C_{12}$ alkyl group, a $C_1$ to $C_{12}$ alkoxy group or a $C_3$ to $C_{12}$ cyclic hydrocarbon group, and one or more hydrogen atoms contained in the alicyclic hydrocarbon group or the aromatic hydrocarbon group may be replaced by a halogen atom, a hydroxy group, a $C_1$ to $C_{12}$ alkyl group, a $C_1$ to $C_{12}$ alkoxy group or a $C_4$ to $C_{36}$ alicyclic hydrocarbon group;

$P^4$ and $P^5$ independently represent a hydrogen atom, a hydroxy group, a $C_1$ to $C_{12}$ alkyl group or a $C_1$ to $C_{12}$ alkoxy group;

$P^6$ and $P^7$ independently represent a $C_1$ to $C_{12}$ alkyl group or a $C_3$ to $C_{12}$ cycloalkyl group, or $P^6$ and $P^7$ may be bonded to form a $C_3$ to $C_{12}$ ring;

$P^8$ represents a hydrogen atom;

$P^9$ represents a $C_6$ to $C_{20}$ aromatic hydrocarbon group, or $P^8$ and $P^9$ may be bonded to form a $C_3$ to $C_{12}$ ring, one or more hydrogen atoms contained in the aromatic hydrocarbon group may be replaced by a $C_1$ to $C_{12}$ alkyl group or $C_3$ to $C_{12}$ cycloalkyl group;

$P^{10}$ to $P^{21}$ independently represent a hydrogen atom, a hydroxy group, a $C_1$ to $C_{12}$ alkyl group or a $C_1$ to $C_{12}$ alkoxy group;

E represents a sulfur atom or an oxygen atom; and m represents 0 or 1.

Examples of the cyclic hydrocarbon group include any one of an alicyclic hydrocarbon group and aromatic hydrocarbon group.

Among the cations represented by the formula (IXz), a cation represented by the formula (IXa) is preferable.

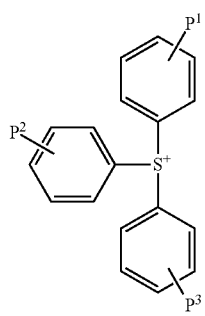

(IXa)

wherein $P^1$ to $P^3$ independently represent a hydrogen atom, a hydroxy group, a halogen atom, a $C_1$ to $C_{12}$ alkyl group, a $C_1$ to $C_{12}$ alkoxy group or a $C_4$ to $C_{36}$ alicyclic hydrocarbon group, and one or more hydrogen atoms contained in the alicyclic hydrocarbon group may be replaced by a halogen atom, a hydroxy group, a $C_1$ to $C_{12}$ alkyl group, a $C_1$ to $C_{12}$ alkoxy group, a $C_6$ to $C_{12}$ aryl group, a $C_7$ to $C_{12}$ aralkyl group, a glycidyloxy group or a $C_2$ to $C_4$ acyl group.

Particularly, the alicyclic hydrocarbon group is suitably a group containing adamantyl structure or isobornyl structure, and preferably 2-alkyl-2-adamantyl group, 1-(1-adamantyl)-1-alkyl group and isobornyl group.

Specific examples of the cation represented by the formula (IXa) include cations below.

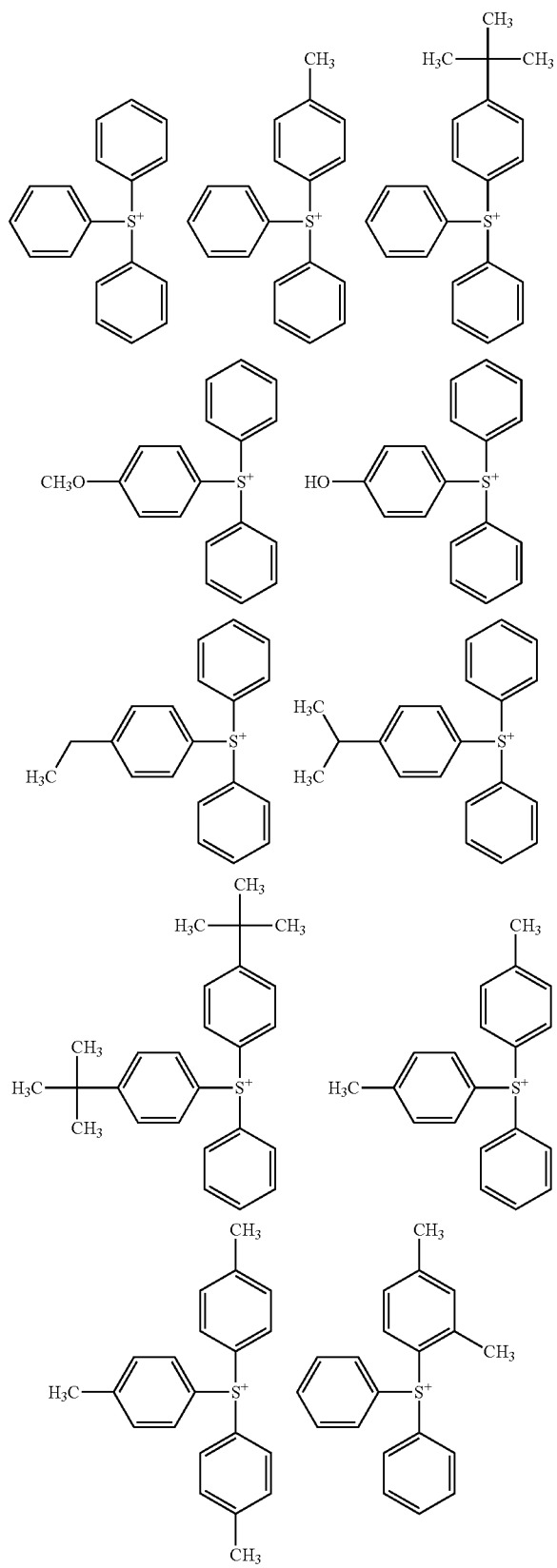

-continued

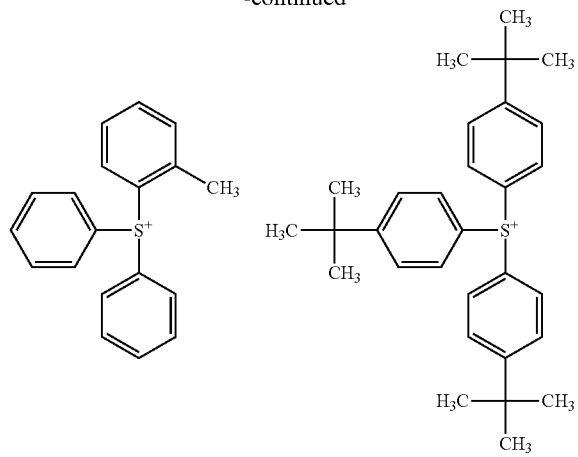

Among the cation represented by the formula (IXa), a cation represented by the formula (IXe) is preferable because of easily-manufacturing.

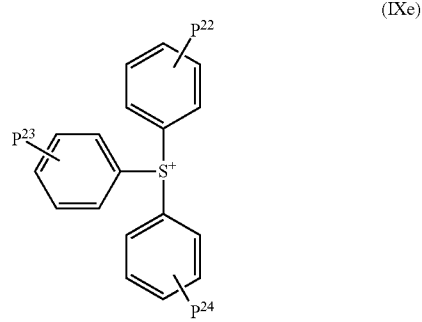

wherein $P^{22}$, $P^{23}$ and $P^{24}$ independently represent a hydrogen atom, a hydroxy group, a halogen atom, a $C_1$ to $C_{12}$ alkyl group or a $C_1$ to $C_{12}$ alkoxy group.

Specific examples of the cation represented by the formula (IXb) include cations below.

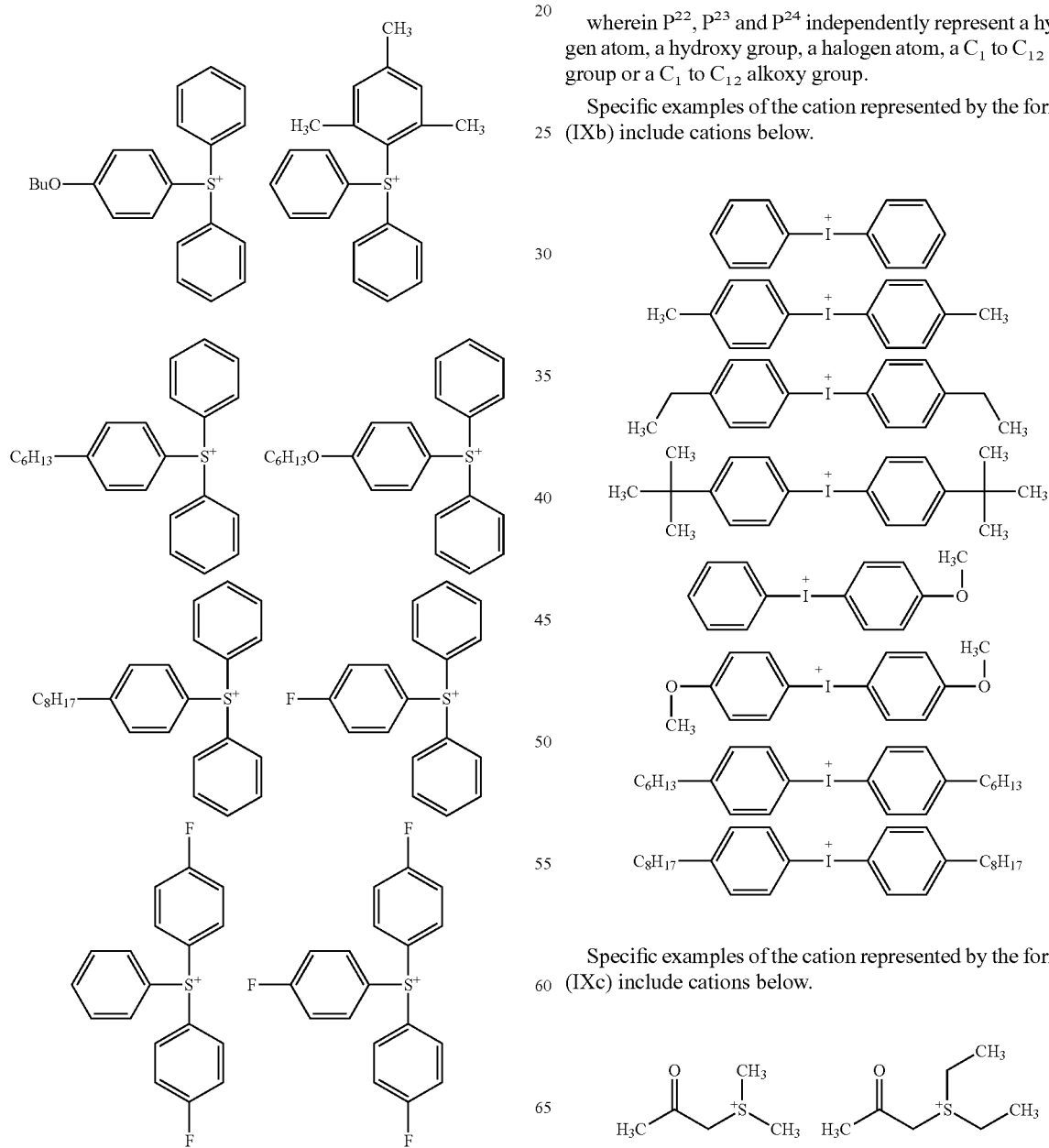

Specific examples of the cation represented by the formula (IXc) include cations below.

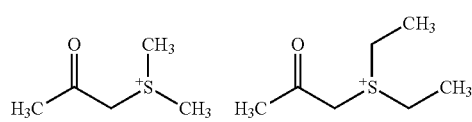

77
-continued
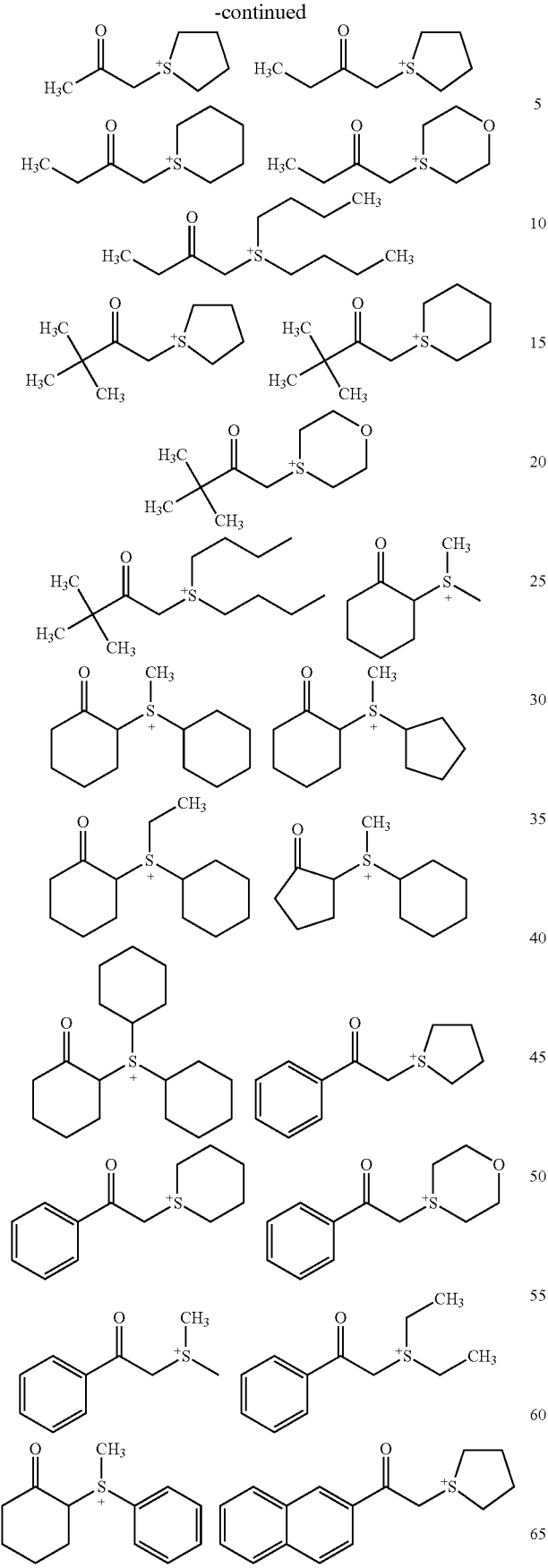
78
-continued
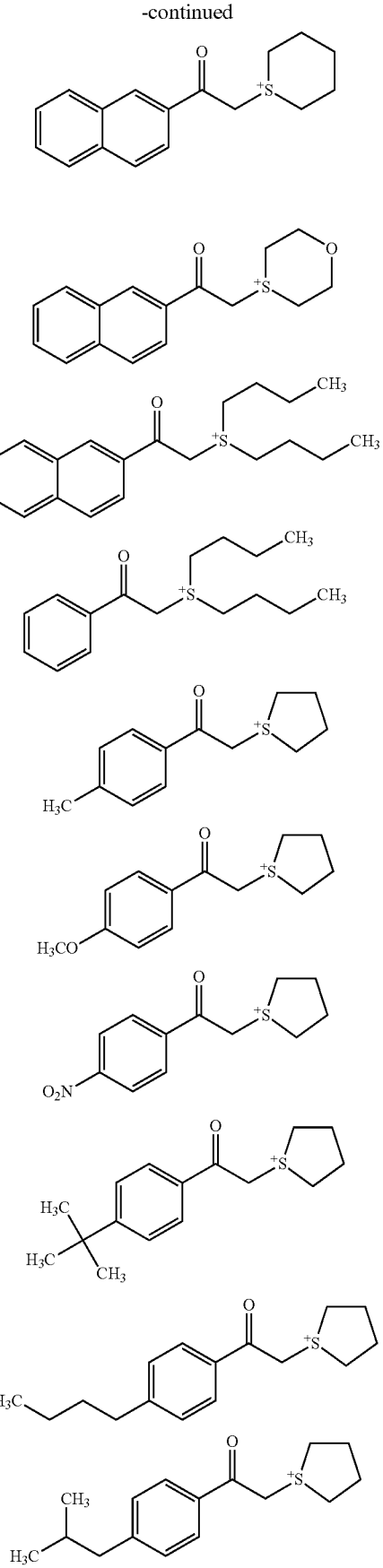

-continued
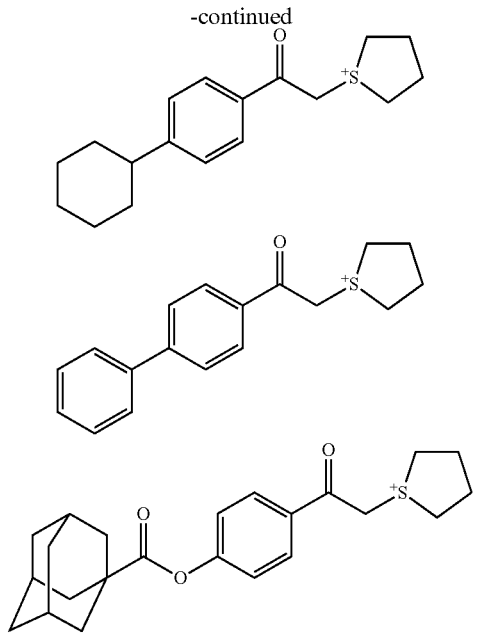
Specific examples of the cation represented by the formula (IXd) include cations below.
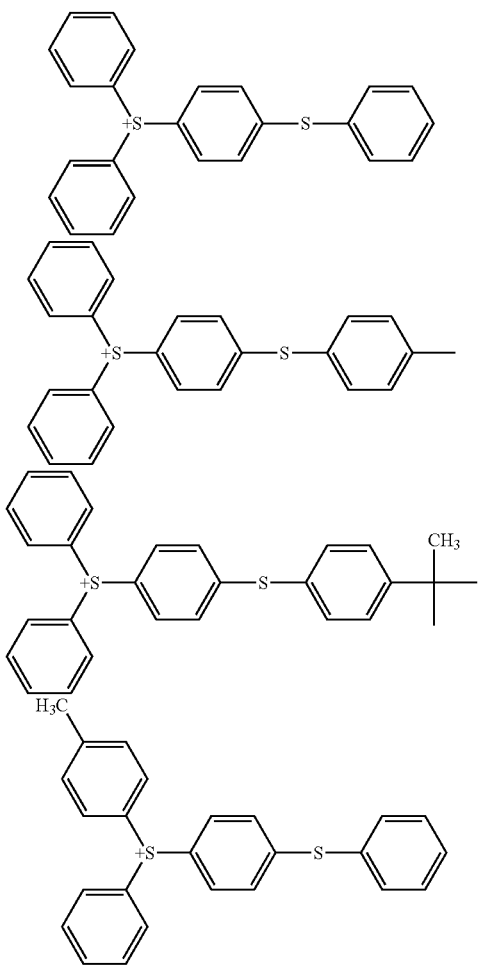
-continued
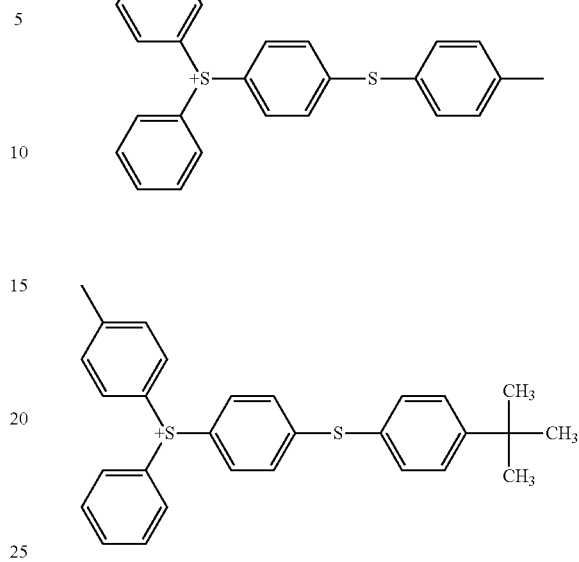
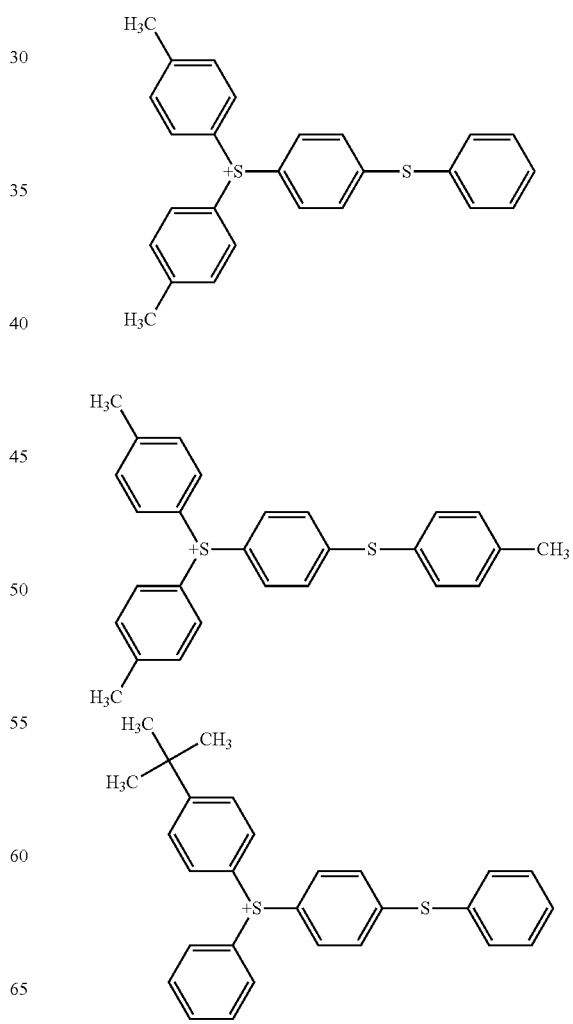

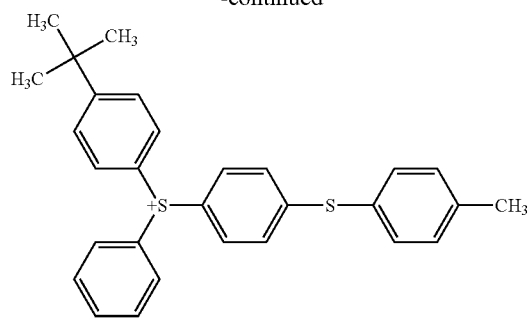
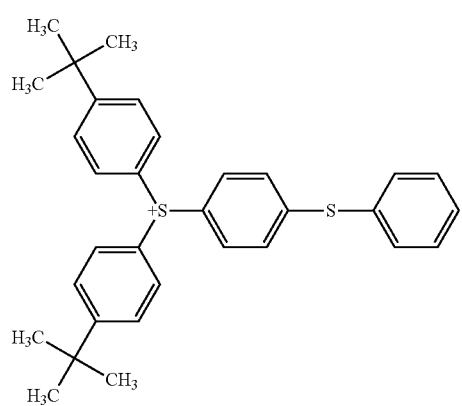
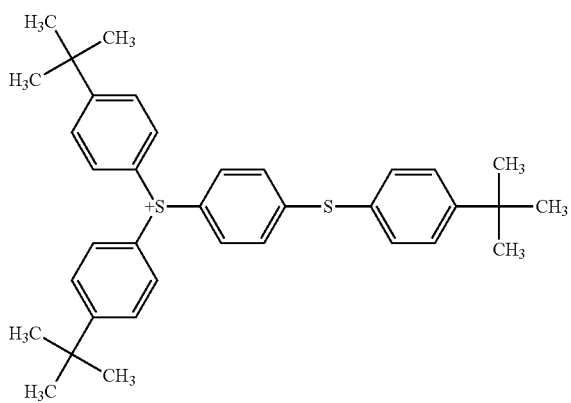
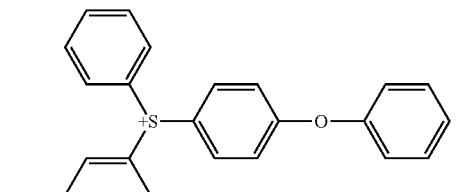
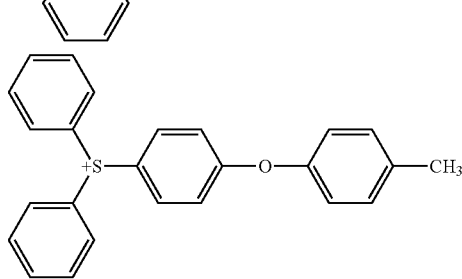
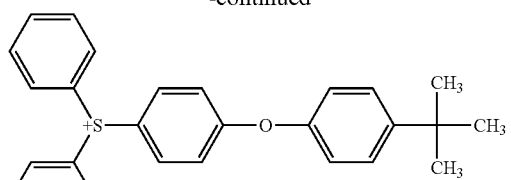
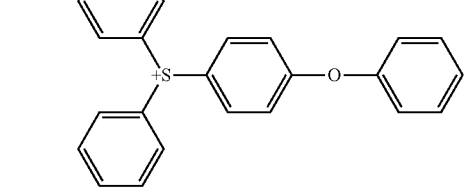
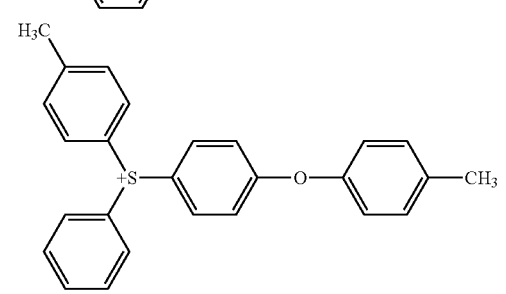
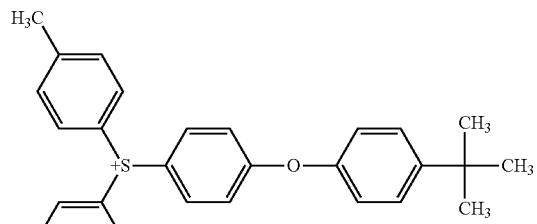
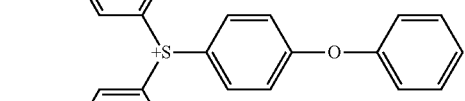
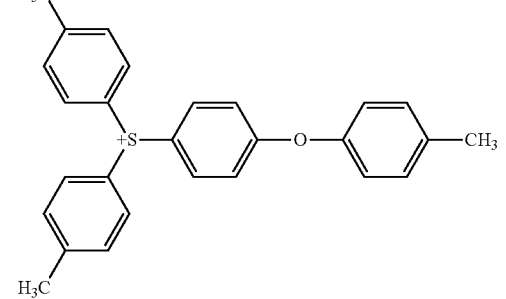

83
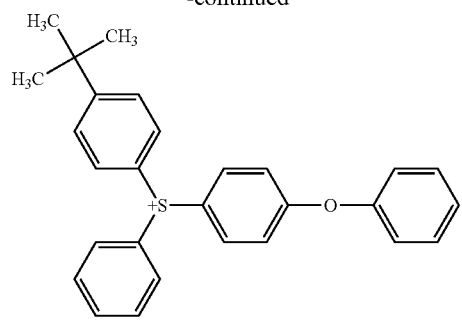
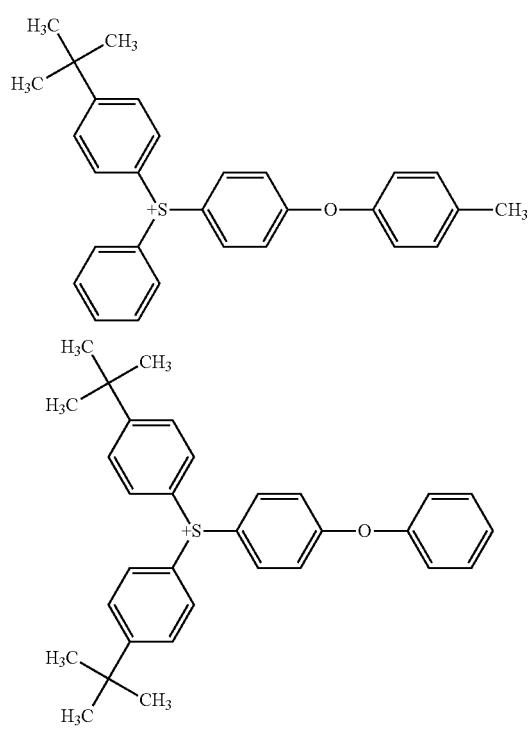
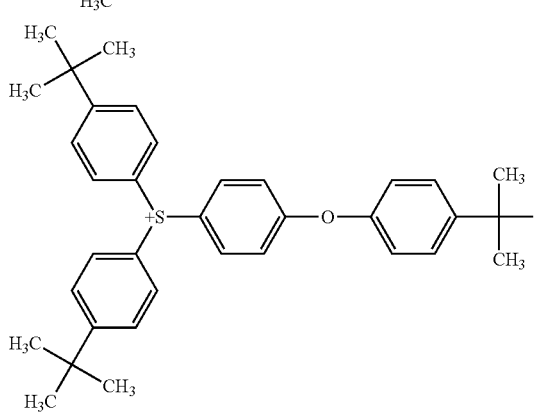
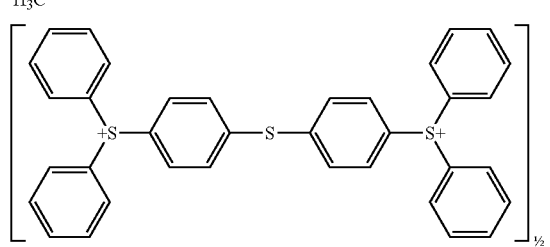
84
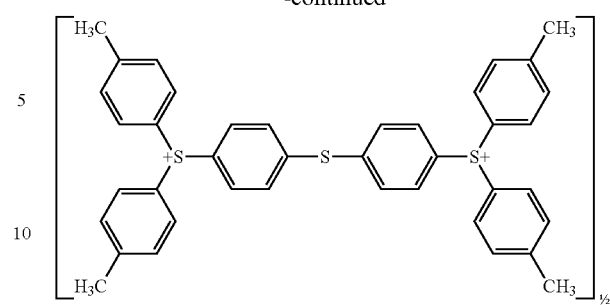
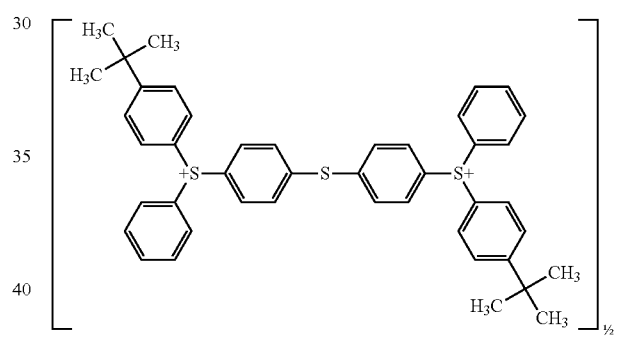
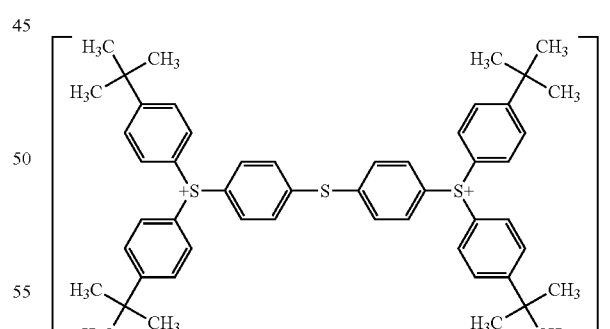
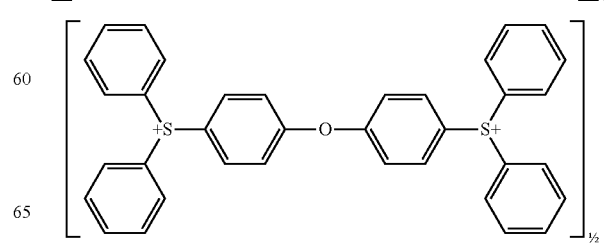

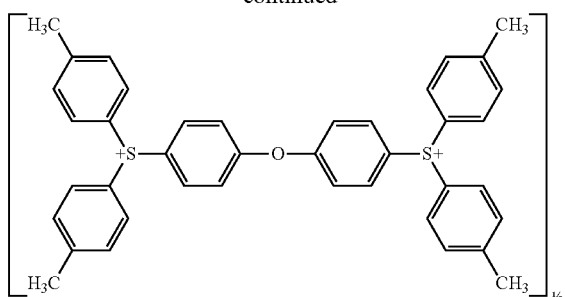
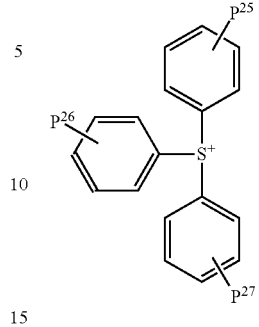
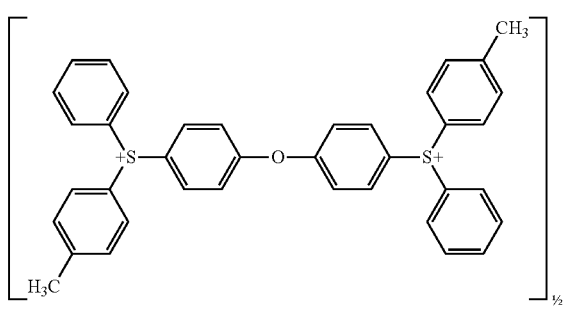
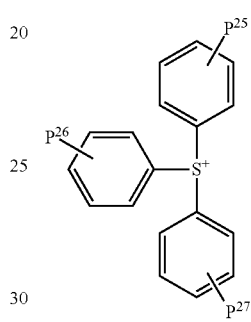
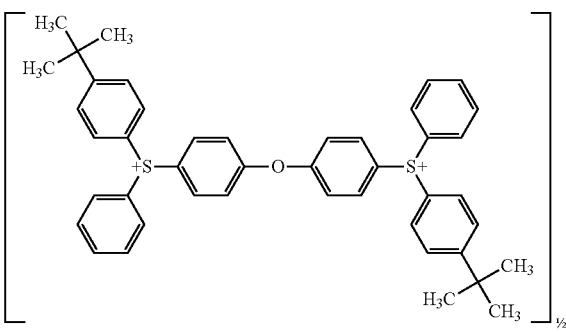
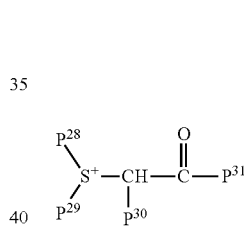
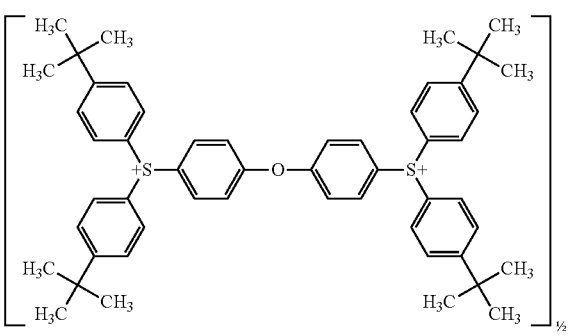
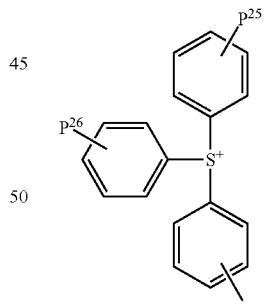
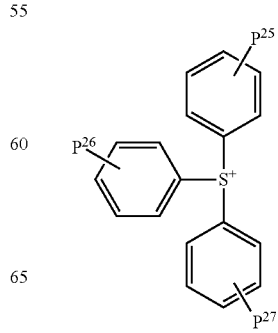
The above-mentioned anions and cations can be combined as desired.
Examples of the salt represented by the formula (I) include the compounds represented by the formula (Xa) to the formula (Xi).

-continued (Xf)

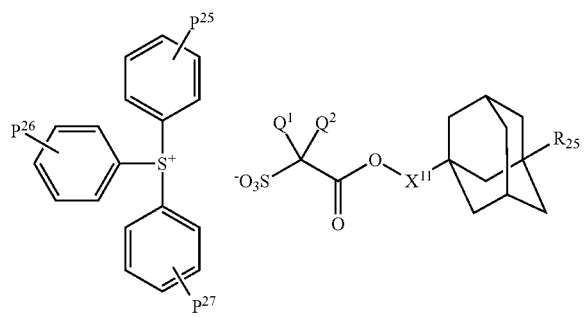

(Xg)

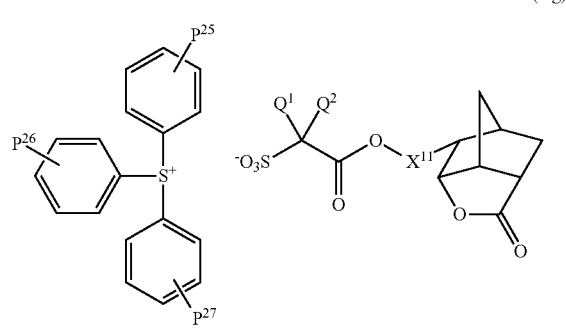

(Xh)

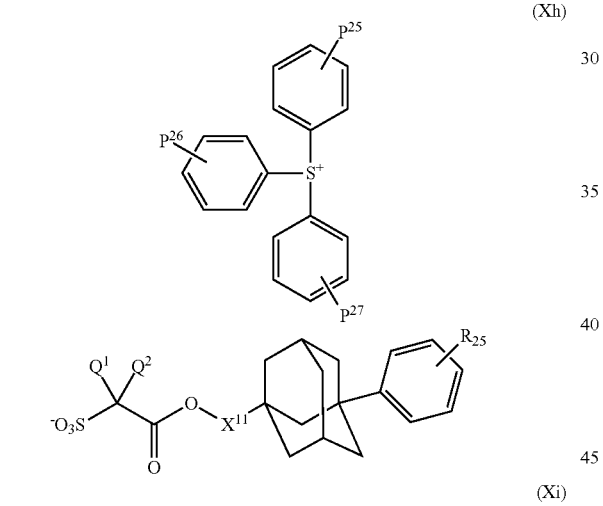

(Xi)

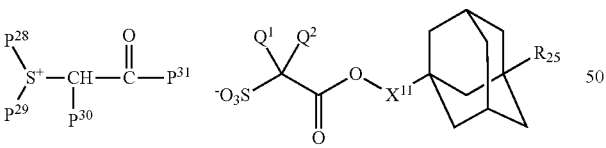

wherein $P^{25}$, $P^{26}$ and $P^{27}$ independently represent a hydrogen atom, a $C_1$ to $C_4$ alkyl group or a $C_4$ to $C_{36}$ alicyclic hydrocarbon group;

$P^{28}$ and $P^{29}$ independently represent a $C_1$ to $C_{12}$ alkyl group or a $C_4$ to $C_{36}$ alicyclic hydrocarbon group, or $P^{28}$ and $P^{29}$ can be bonded together to form a $C_2$ to $C_6$ ring that includes $S^+$;

$P^{30}$ represent a $C_1$ to $C_{12}$ alkyl group, a $C_4$ to $C_{36}$ alicyclic hydrocarbon group or an optionally substituted $C_6$ to $C_{20}$ aromatic hydrocarbon group, or $P^{30}$ and $P^{31}$ can be bonded together to form a $C_3$ to $C_{12}$ ring, and one or more —CH$_2$— contained in the ring may be replaced by —O—, —S— or —CO—;

$Q^1$ and $Q^2$ represent the same meaning as defined above and $X^{13}$ represents a single bond or a methylene group.

Examples of the ring formed by $P^{28}$ and $P^{29}$ bonded together include tetrahydrothiophenium group.

Examples of the ring formed by $P^{30}$ and $P^{31}$ bonded together include the group represented by the formula (W13) to the formula (W15) described above.

Among the abovementioned combinations, examples include the salts below.

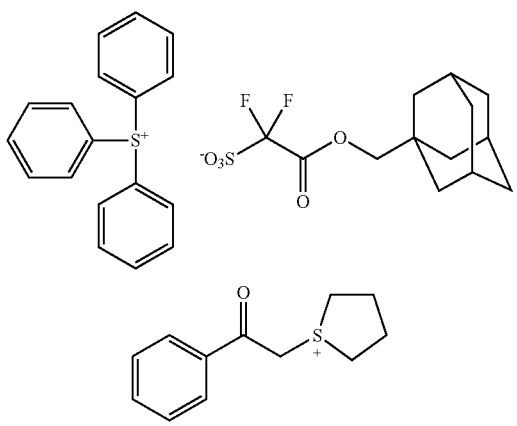

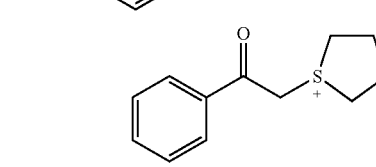

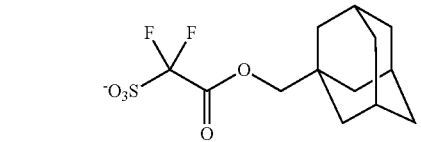

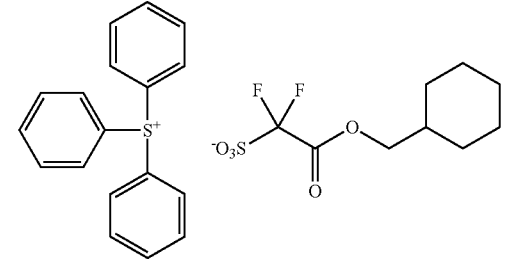

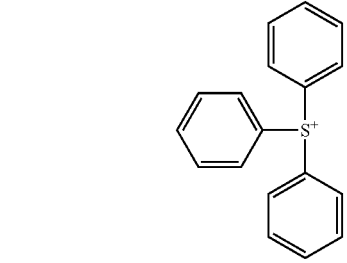

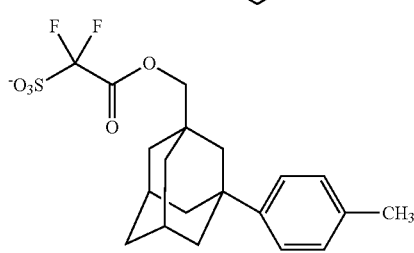

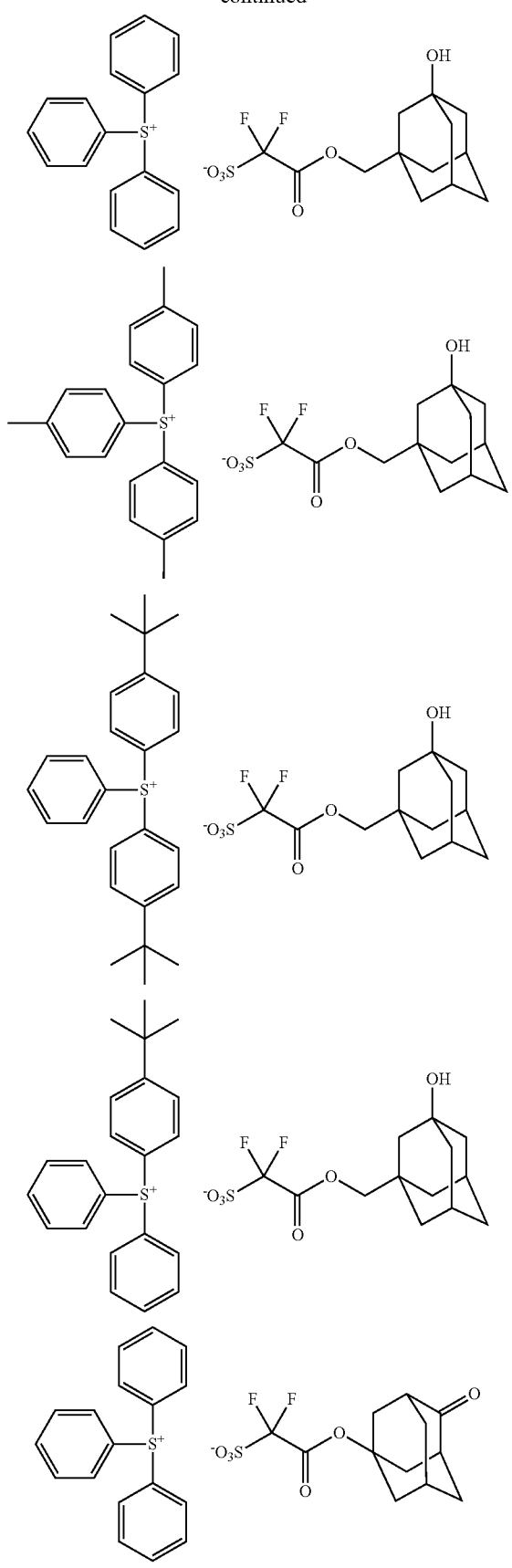
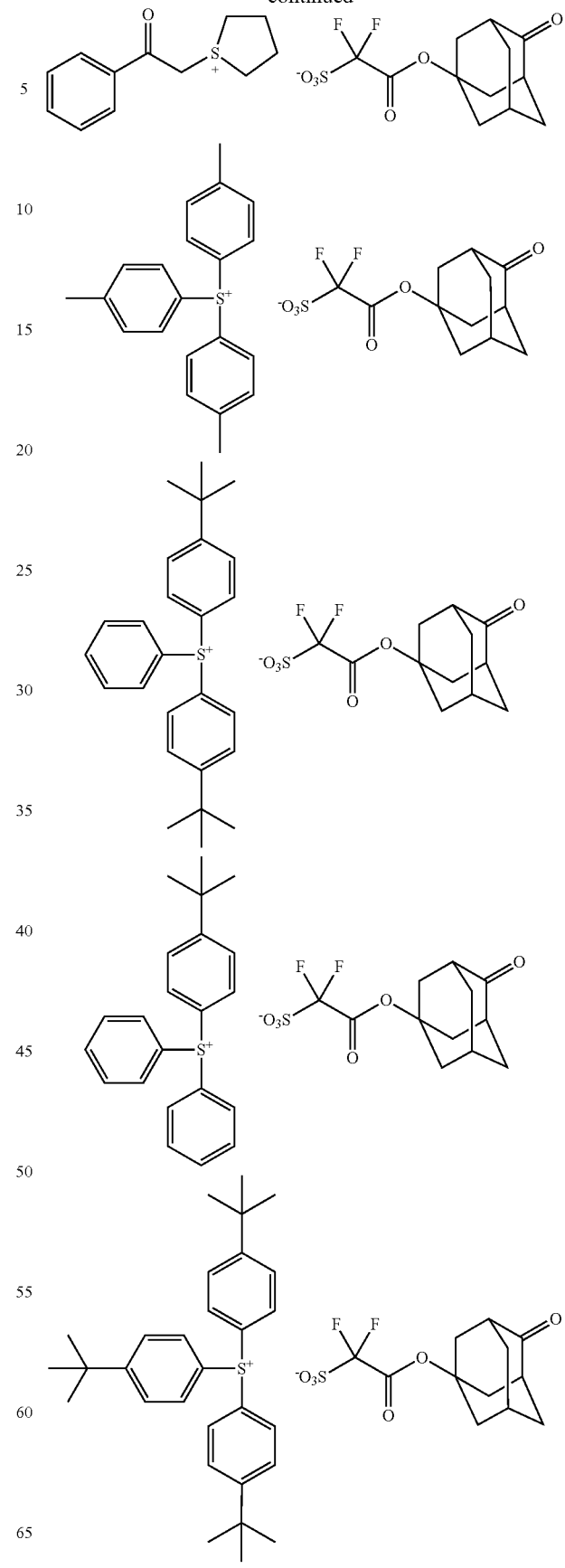

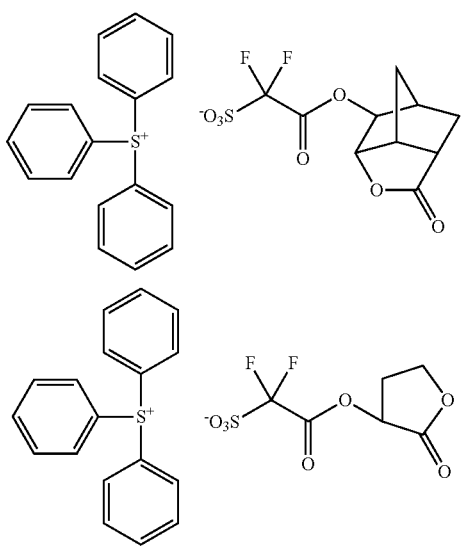

The salt represented by the formula (I) can be produced, for example, according to the manufacturing method described in JP-2008-209917-A.

In the resist composition of the present invention, the content of the acid generator is preferably in the range of 1 to 30 parts by weight, and more preferably 1 to 20 parts by weight, and still more preferably 1 to 15 parts by weight with respect to 100 parts by weight of the resin. The acid generator represented by the formula (I) may be used singly or in combination with two or more.

The resist composition containing the acid generator and resin described above may include a basic compound. Preferred examples of the basic compound include a nitrogen-containing organic compound, particularly amines and ammonium salts. The basic compound can be added as a quencher to improve performance from being compromised by the inactivation of the acid while the material is standing after exposure.

The Examples of such basic compounds used as the quencher include those represented by the following formulae.

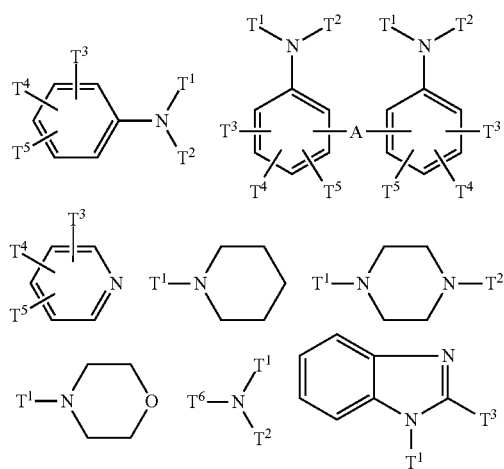

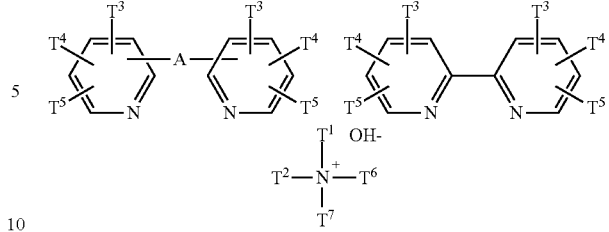

wherein $T^1$, $T^2$ and $T^7$ independently represent a hydrogen atom, a $C_1$ to $C_6$ alkyl group, a $C_5$ to $C_{10}$ alicyclic hydrocarbon group or a $C_6$ to $C_{20}$ aromatic hydrocarbon group, one or more hydrogen atoms contained in the alkyl group, alicyclic hydrocarbon group and aromatic hydrocarbon group may be replaced by a hydroxy group, an amino group or a $C_1$ to $C_6$ alkoxy group, one or more hydrogen atoms contained in the amino group may be placed by a $C_1$ to $C_4$ alkyl group;

$T^3$ to $T^5$ independently represent a hydrogen atom, a $C_1$ to $C_6$ alkyl group, a $C_1$ to $C_6$ alkoxy group, a $C_5$ to $C_{10}$ alicyclic hydrocarbon group or a $C_6$ to $C_{20}$ aromatic hydrocarbon group, one or more hydrogen atoms contained in the alkyl group, the alkoxy group, the alicyclic hydrocarbon group and aromatic hydrocarbon group may be replaced by a hydroxy group, an amino group or a $C_1$ to $C_6$ alkoxy group, one or more hydrogen atoms contained in the amino group may be replaced by a $C_1$ to $C_4$ alkyl;

$T^6$ represents a $C_1$ to $C_6$ alkyl group or a $C_5$ to $C_{10}$ alicyclic hydrocarbon group, one or more hydrogen atoms contained in the alkyl group and the alicyclic hydrocarbon group may be replaced by a hydroxy group, an amino group or a $C_1$ to $C_6$ alkoxy group, one or more hydrogen atoms contained in the amino group may be replaced by a $C_1$ to $C_4$ alkyl group;

A represents a $C_2$ to $C_6$ alkylene group, a carbonyl group, an imino group, a sulfanediyl group or a disulfanediyl group.

Specific examples of such compounds include hexylamine, heptylamine, octylamine, nonylamine, decylamine, aniline, 2-, 3- or 4-methylaniline, 4-nitroaniline, diisopropylaniline, 1- or 2-naphtylamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane, dibutylamine, dipentylamine, dihexylamine, diheptylamine, dioctylamine, dinonylamine, didecylamine, N-methylaniline, piperidine, diphenylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethydipentylamine, ethyldihexylamine, ethydiheptylamine, ethyldioctylamine, ethyldinonylamine, ethyldidecylamine, dicyclohexylmethylamine, tris[2-(2-methoxyethoxy)ethyl]amine, triisopropanolamine, N,N-dimethylaniline, 2,6-diisopropylaniline, imidazole, pyridine, 4-methylpyridine, 4-methylimidazole, bipyridine, 2,2'-dipyridylamine, di-2-pyridylketone, 1,2-di(2-pyridyl)ethane, 1,2-di(4-pyridyl)ethane, 1,3-di(4-pyridyl)propane, 1,2-bis(2-pyridyl)ethylene, 1,2-bis(4-pyridyl)ethylene, 1,2-bis(4-pyridyloxy)ethane, 4,4'-dipyridylsulfide, 4,4'-dipyridyldisulfide, 1,2-bis(4-pyridyl)ethylene, 2,2'-dipicolylamine, 3,3'-dipicolylamine, tetramethylammonium hydroxide, tetraisopropylammonium hydroxide, tetrabutylammonium hydroxide, tetra-n-hexylammonium hydroxide, tetra-n-octylammonium hydroxide, phenyltrimethylammonium hydroxide, 3-(trifluoromethyl)phenyltrimethylammonium hydroxide, and (2-hydroxyethyl)trimethylammonium hydroxide (common name: choline). Among these, diisopropylaniline is preferable.

Furthermore, hindered amine compounds with a piperidine skeleton such as those disclosed in JP-A-H11-52575 can be used as a quencher.

In the present resist composition, the content of the resin is preferably in the range of about 80 to 99.9 wt %, and the content of the acid generator is preferably in the range of about 0.1 to 20 wt %, based on the total amount of solids.

The content of the basic compound containing as a quencher in the resist composition, if used, is preferably in the range of about 0.01 to 1 wt %, based on the total amount of solids in the resist composition.

The resist composition can also include small amounts of various additives such as sensitizers, dissolution inhibitors, other resins, surfactants, stabilizers, and dyes, as needed.

The resist composition of the present invention is generally a resist solution, with the various ingredients above dissolved in a solvent, and is applied onto a substrate such as a silicon wafer by a method industrially-used such as spin coating. The solvent used here can be any solvent that is industrially used in the field and that dissolves the ingredients, dries at a suitable rate, and results in a smooth, uniform film after evaporating off.

Examples thereof include glycol ether esters such as ethylcellosolve acetate, methylcellosolve acetate and propylene glycol monomethyl ether acetate; ethers such as diethylene glycol dimethyl ether; esters such as ethyl lactate, butyl acetate, amyl acetate and ethyl pyruvate; ketones such as acetone, methyl isobutyl ketone, 2-heptanone and cyclohexanone; and cyclic esters such as γ-butyrolactone. These solvents can be used alone or in combination of two or more.

The method for producing a resist pattern of the present invention includes steps of:

(1) applying the resist composition of the present invention onto a substrate;
(2) drying the applied composition to form a composition layer;
(3) exposing to the composition layer using a exposure device;
(4) baking the exposed composition layer and,
(5) developing the baked composition layer using a developing apparatus.

The application of the resist composition onto the substrate can generally be carried out through the use of a device such as a spin coater.

The drying, for example, can either be carried out by baking the applied composition using a heating device such as a hotplate, or can be carried out using a decompression device, and a composition layer is formed. The temperature in this case is generally the range of 50 to 200° C. Moreover, the pressure is generally the range of 1 to $1.0 \times 10^5$ Pa.

The composition layer obtained is exposed to light using an exposure device or a liquid immersion exposure device. The exposure is generally carried out through a mask that corresponds to the required pattern. Various types of exposure light source can be used, such as irradiation with ultraviolet lasers such as KrF excimer laser (wavelength: 248 nm), ArF excimer laser (wavelength: 193 nm), $F_2$ laser (wavelength: 157 nm), or irradiation with far-ultraviolet wavelength-converted laser light from a solid-state laser source (YAG or semiconductor laser or the like) or vacuum ultraviolet harmonic laser light or the like.

After exposure, the composition layer is subjected to a baking treatment to promote the deprotection reaction. The baking temperature is generally in the range of 50 to 200° C., preferably in the range of 70 to 150° C.

The composition layer is developed after the heat treatment, generally by utilizing an alkaline developing solution using a developing apparatus. Here, for the alkaline developing solution, various types of aqueous alkaline solutions used in this field can be satisfactory. Examples include aqueous solutions of tetramethylammonium hydroxide and (2-hydroxyethyl)trimethylammonium hydroxide (common name: choline).

After developing, it is preferable to rinse with ultrapure water and to remove any residual water on the substrate and the pattern.

The resin and composition using same of the present invention are useful in resist compositions, and particularly in chemically amplified photoresist compositions, and can be used in the microfabrication of semiconductors and in manufacture of liquid crystals, thermal print heads for circuit boards and the like, and furthermore in other photofabrication processes, and they can be suitably used in a wide range of applications. In particular, since they exhibit a superior LER, they can be used as a suitable chemically amplified photoresist composition for excimer laser lithography such as with KrF or the like, as well as EB lithography and EUV exposure lithography. Moreover, in addition to liquid immersion exposure, they can also be used in dry exposure and the like. Furthermore, they can also be used in double imaging, and have industrial utility.

EXAMPLES

The resist composition of the present invention will be described more specifically by way of examples, which are not construed to limit the scope of the present invention.

All percentages and parts expressing the content or amounts used in the Examples and Comparative Examples are based on weight, unless otherwise specified.

The weight average molecular weight is a value determined by gel permeation chromatography (Toso Co. ltd. HLC-8120GPC type, coulum: Three of TSK gel Multipore HXL-M, solvent: tetrahydroflun) using polystyrene as the standard product.

Column: Three of TSK gel Multipore HXL-M+guardcolumn (Tosoh Co. Ltd.)

Eluant: tetrahydrofuran

Flow rate: 1.0 mL/min

Detecting device: RI detector

Column temperature: 40° C.

Injection amount: 100 μL

Standard material for calculating molecular weight: standard polyethylene (Tosoh Co. Ltd.)

The structures of the compounds were verified by NMR (Nippon electric, GX-270 type or EX-270 type) and mass analysis (LC: Agilent 1100 type, MASS: Agilent LC/MSD type or LC/MSD TOF type).

Example 1

Synthesis of Compound (a1-4)

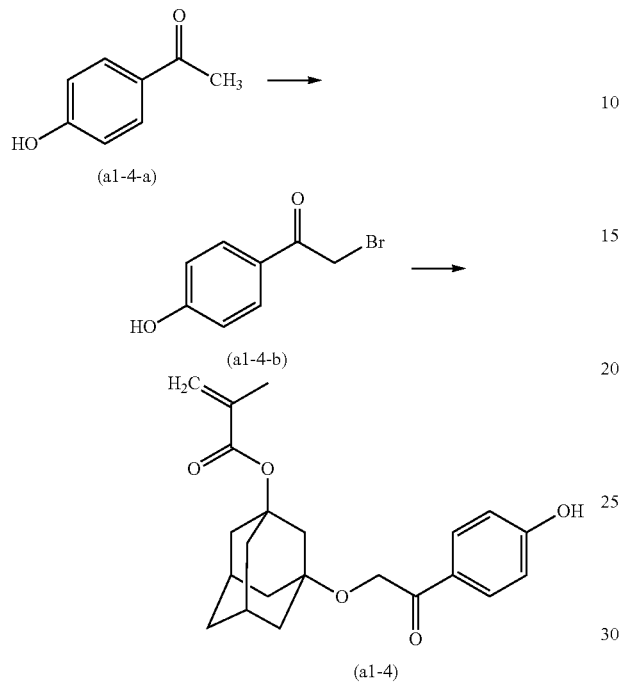

13.62 parts of a compound (a1-4-a) and 23.30 parts of 1,4-dioxane were mixed while stirring at 23° C. A mixture prepared by dissolving 25.00 parts of bromine-dioxane complex in 125 parts of 1,4-dioxane was added to the obtained mixed solution in the form of drops over 1 hour at 23° C. The obtained mixed solution was stirred for 1 hour at 23° C. To the obtained mixed solution were added 140 parts of 5% potassium carbonate aqueous solution and 115 parts of ethylacetate, and obtained solution was stirred and separated. To a recovered organic layer was added 133 parts of ion-exchanged water to separate and wash, and then an organic layer was recovered. The obtained organic layer was concentrated, thus concentrated mass was mixed with 50 parts of methanol while stirring, and the recrystallization and filteration conducted, whereby giving 17.80 parts of a compound (a1-4-b) as a white solid.

15.05 parts of compound (a1-4-b), 45.00 parts of ethylacetate and 0.0013 parts of p-toluenesulfonic acid were mixed while stirring at 23° C. To the obtained mixed solution was added 6.06 parts of ethyl vinyl ether, the mixture was stirred for 5 hours at 23° C. To the obtained mixed solution was added 33 parts of ion-exchanged water to separate and wash, and then an organic layer was recovered. The obtained organic layer was concentrated, whereby giving the compound (a1-4-b) in which hydroxy group was protected.

10.00 parts of tetrahydrofuran (THF), 1.46 parts of 4-dimethylaminopyridine and 2.36 parts of 3-hydroxy-1-adamantyl-metacrylate were mixed while stirring at 23° C. To the obtained mixed solution was added 2.87 parts of the compound (a1-4-b) in which hydroxy group is protected for 1 hour at 40° C. The obtained mixture solution was stirred for 16 hours at 40° C. To the obtained mixed solution were added 10.00 parts of ion-exchanged water and 25.00 parts of ethyl acetate to separate and wash, and then an organic layer was recovered. The obtained organic layer was mixed with 25.0 parts of 5% potassium bicarbonate aqueous solution to separate and wash, and then an organic layer was recovered. To the obtained organic layer was further added 25.00 parts of 1% hydrochloric acid, and the resultant mixture was stirred for 3 hours, and then an organic layer was separate and recovered. The obtained organic layer was concentrated, and then column-fractionated under the condition below, whereby giving 1.58 parts of the compound (a1-4).

Developing medium: silica gel 60, 200 mesh (Merck & Co., Inc.)

Developing solvent: n-heptane/ethyl acetate=10/1 (volume ratio)

MS: 370.2

$^1$H-NMR (dimethyl sulfoxide-$d_6$, internal standard material tetramethylsilane): δ(ppm) 1.47-2.20 (m, 15H), 2.31-2.40 (m, 2H), 4.67 (s, 2H), 5.49 (m, 1H), 6.01 (m, 1H), 7.78 (m, 2H), 7.85 (m, 2H), 9.59 (s, 1H)

Example 2

Synthesis of Compound (a1-5)

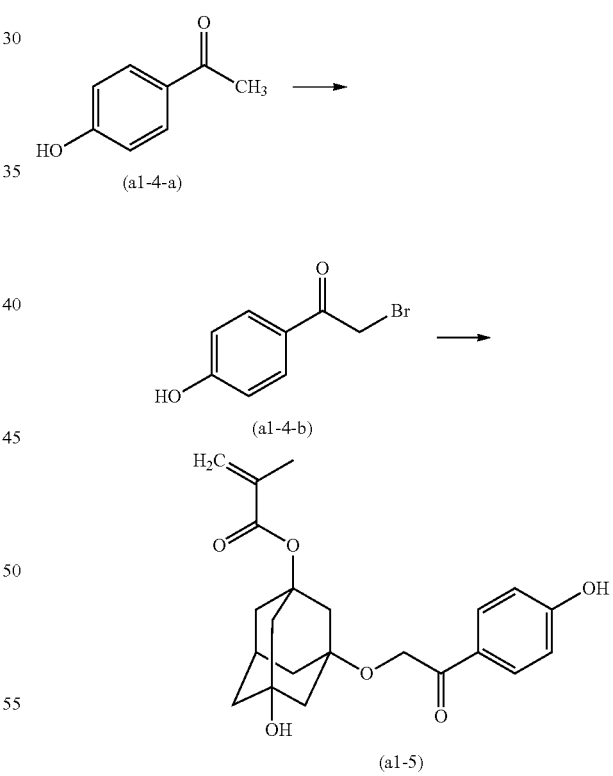

0.42 parts of a compound (a1-5) was produced in the same manner as in Example 1 except that 2.52 parts of 3,5-dihydroxy-1-adamantyl methacrylate was used instead of 2.36 parts of 3-hydroxy-1-adamantyl methacrylate.

MS: 386.2

$^1$H-NMR (dimethyl sulfoxide-$d_6$, internal standard material tetramethylsilane): δ(ppm) 1.89 (s, 3H), 1.95-2.15 (m, 6H), 2.35-2.62 (m, 7H), 4.42 (bs, 1H), 4.67 (s, 2H), 5.49 (m, 1H), 6.01 (m, 1H), 7.78 (m, 2H), 7.85 (m, 2H), 9.59 (s, 1H)

Example 3

Synthesis of Compound (a1-4')

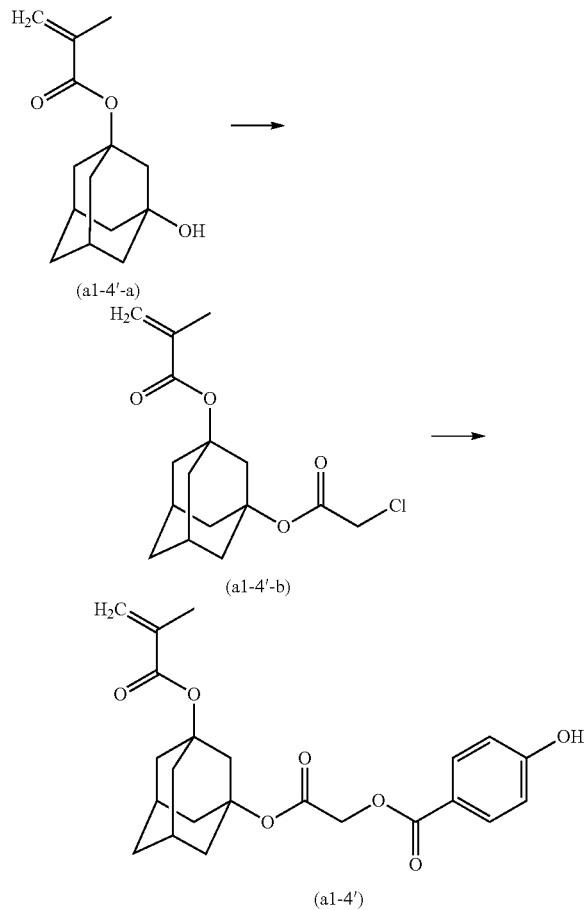

23.63 parts of 3-hydroxy-1-adamantyl methacrylate and 100 parts of THF were mixed while stirring 1 hour at 23° C. To the obtained mixed solution was added 10.49 parts of 4-dimethylaminopyridine, and the mixture was heated up to 40° C. A mixed solution containing 16.94 parts of chloroacetyl chloride and 34 parts of THF was added thereto in the form of drops over 1 hour. After that, the obtained mixture was stirred for 8 hours at 40° C., and cooled down to 5° C. 100 parts of ion-exchanged water of 5° C. was added thereto, and the obtained mixture was stirred and separated to recover a water layer. To the obtained water layer was added 300 parts of ethyl acetate, and separated to recover an organic layer. To the obtained organic layer was added 200 parts of 10% potassium carbonate aqueous solution of 5° C. to wash, and separated to recover an organic layer. Then, to the recovered organic layer was added 200 parts of ion-exchanged water to wash, and the resultant was separated to recover an organic layer. These operations were repeated 3 times, and the recovered organic layer was concentrated, whereby giving 10.69 parts of a compound (a1-4'-b).

1.38 parts of 4-hydroxy-benzoic acid and 20 parts of N,N-dimethylformamide (DMF) were mixed while stirring 1 hour at 23° C. To the obtained mixed solution were added 0.69 parts of potassium carbonate and 0.17 parts of potassium iodide, and the mixture was heated up to 50° C. The resultant mixture was stirred for 1 hour, and heated up to 100° C. To the obtained mixture was added in the form of drops a mixed solution containing 3.13 parts of the compound (a1-4'-b) and 30 parts of DMF over 1 hour, the resultant mixture was stirred 3 hours at 100° C. The obtained mixture was cooled to 23° C., and 50 parts of ion-exchanged water and 200 parts of ethyl acetate were added thereto, and the obtained mixture was stirred and separated to recover an organic layer. To the obtained organic layer was added 50 parts of 5% potassium carbonate aqueous solution of 5° C. to wash, and separated to recover an organic layer. Then, to the recovered organic layer was added 100 parts of ion-exchanged water to wash, and the resultant was separated to recover an organic layer. These operations were repeated 3 times, and the recovered organic layer was concentrated, and then column-fractionated under the condition below, whereby giving 1.26 parts of the compound (a1-4').

Developing medium: silica gel 60, 200 mesh (Merck & Co., Inc.)

Developing solvent: n-heptane/ethyl acetate=10/1 (volume ratio)

MS: 414.2

$^1$H-NMR (dimethyl sulfoxide-$d_6$, internal standard material tetramethylsilane): δ(ppm) 1.47-2.20 (m, 15H), 2.31-2.40 (m, 2H), 5.25 (s, 2H), 5.49 (m, 1H), 6.01 (m, 1H), 7.78 (m, 2H), 7.95 (m, 2H), 9.59 (s, 1H)

Example 4

Synthesis of Compound (a1-5')

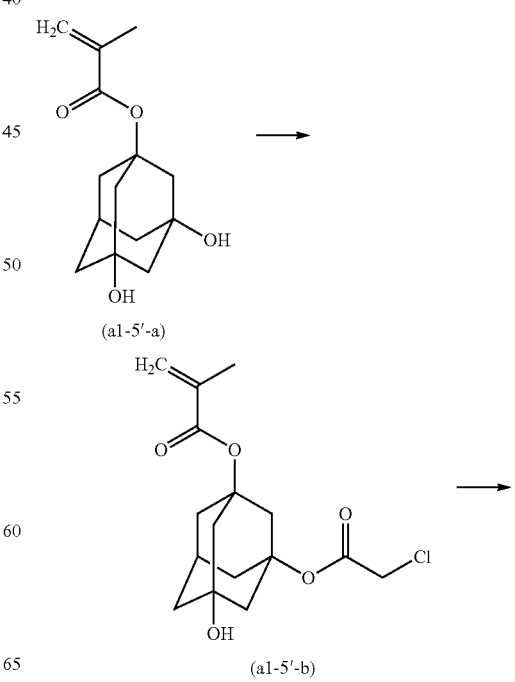

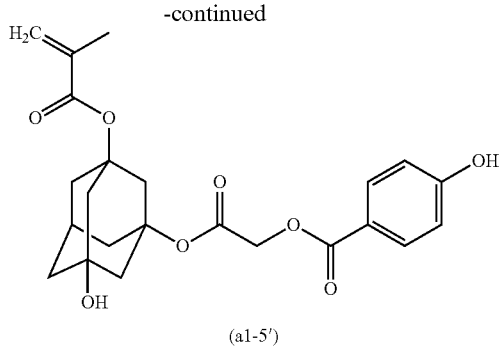

(a1-5')

0.43 parts of a compound (a1-5') was produced in the same manner as in Example 3 except that 25.23 parts of 3,5-dihydroxy-1-adamantyl methacrylate was used instead of 2.36 parts of 3-hydroxy-1-adamantyl methacrylate.

MS: 430.2

$^1$H-NMR (dimethyl sulfoxide-$d_6$, internal standard material tetramethylsilane): δ(ppm) 1.89 (s, 3H), 1.95-2.15 (m, 6H), 2.35-2.62 (m, 7H), 4.42 (bs, 1H), 5.25 (s, 2H), 5.49 (m, 1H), 6.01 (m, 1H), 7.78 (m, 2H), 7.85 (m, 2H), 9.59 (s, 1H)

Example 5

Synthesis of Compound (a1-A)

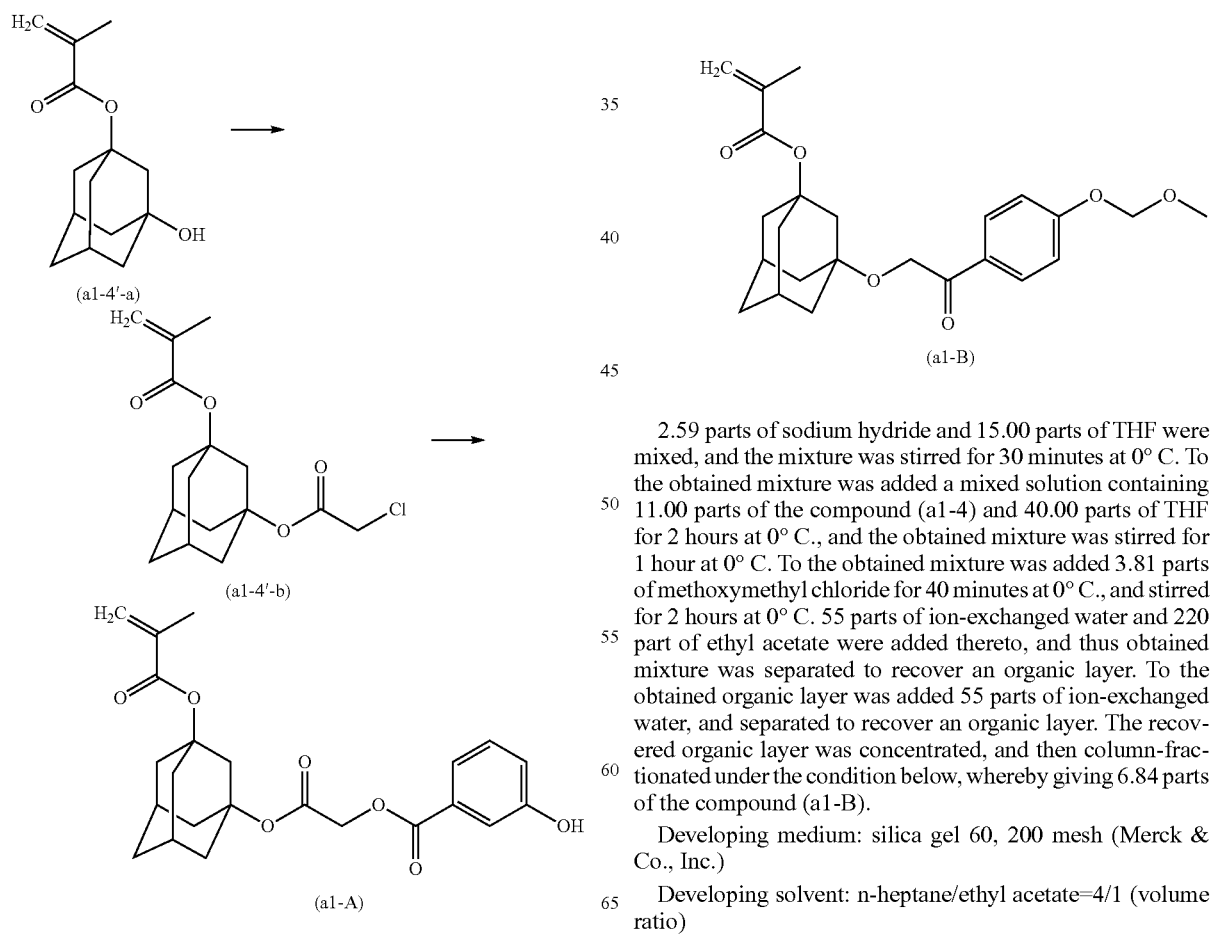

0.86 parts of a compound (a1-A) was produced in the same manner as in Example 3 except that 3-hydroxy-benzoic acid was used instead of 4-hydroxy-benzoic acid and.

MS: 414.2

Example 6

Synthesis of Compound (a1-B)

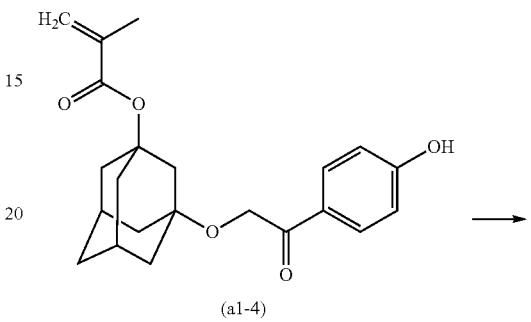

(a1-4)

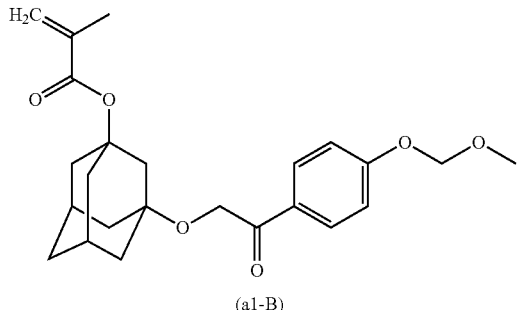

(a1-B)

2.59 parts of sodium hydride and 15.00 parts of THF were mixed, and the mixture was stirred for 30 minutes at 0° C. To the obtained mixture was added a mixed solution containing 11.00 parts of the compound (a1-4) and 40.00 parts of THF for 2 hours at 0° C., and the obtained mixture was stirred for 1 hour at 0° C. To the obtained mixture was added 3.81 parts of methoxymethyl chloride for 40 minutes at 0° C., and stirred for 2 hours at 0° C. 55 parts of ion-exchanged water and 220 part of ethyl acetate were added thereto, and thus obtained mixture was separated to recover an organic layer. To the obtained organic layer was added 55 parts of ion-exchanged water, and separated to recover an organic layer. The recovered organic layer was concentrated, and then column-fractionated under the condition below, whereby giving 6.84 parts of the compound (a1-B).

Developing medium: silica gel 60, 200 mesh (Merck & Co., Inc.)

Developing solvent: n-heptane/ethyl acetate=4/1 (volume ratio)

MS: 414.2

Example 7

Synthesis of Compound (a1-C)

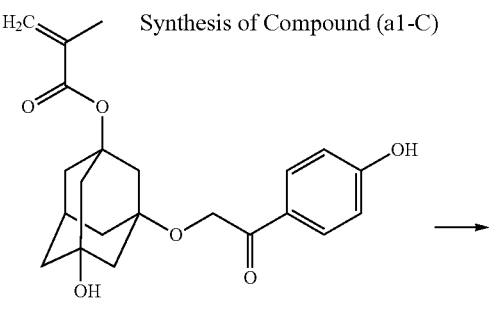

(a1-5)

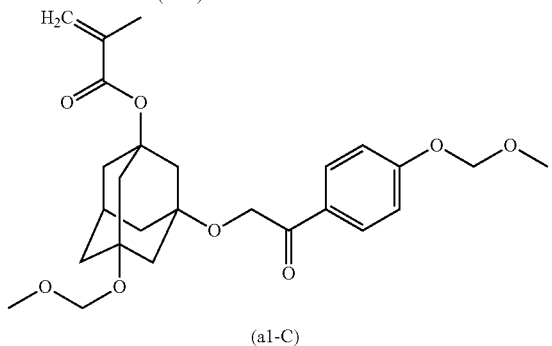

(a1-C)

4.97 parts of sodium hydride and 15.00 parts of THF were mixed and the mixture was stirred for 30 minutes at 0° C. To the obtained mixture were added a mixed solution containing 11.00 parts of the compound (a1-5) and 40.00 parts of THF for 2 hours at 0° C., and the obtained mixture was stirred for 1 hour at 0° C. To the obtained mixture was added 7.31 parts of methoxymethyl chloride for 40 minutes 0° C., and stirred for 2 hours at 0° C. 55 parts of ion-exchanged water and 220 parts of ethyl acetate were added thereto, and thus obtained mixture was separated to recover an organic layer. To the obtained organic layer was added 55 parts of ion-exchanged water, and separated to recover an organic layer. The recovered organic layer was concentrated, and then column-fractionated under the condition below, whereby giving 3.72 parts of the compound (a1-C).

Developing medium: silica gel 60, 200 mesh (Merck & Co., Inc.)

Developing solvent: n-heptane/ethylacetate=1/1 (volume ratio)

MS: 474.2

Example 8

Synthesis of Compound (a1-D)

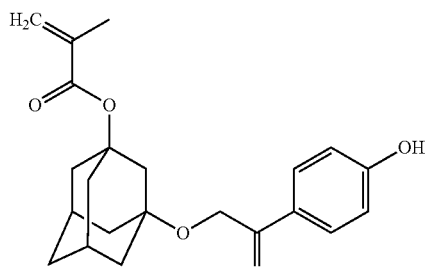

(a1-4)

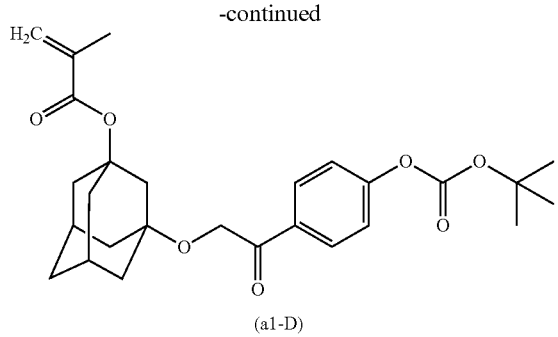

(a1-D)

4.41 parts of the compound (a1-4), 30.83 parts of THF and 2.18 parts of 4-dimethylaminopyridine were mixed and the mixture was stirred for 30 minutes at 23° C. To the obtained mixture was added 3.37 parts of di-tert-butyldicarbonate in the form of drops, and the obtained mixture was stirred for 5 hour at 40° C. To the obtained mixture was added 1.81 parts of conc. hydrochloric acid, and the resultant mixture was stirred for 30 minutes. Then, 40 parts of ethyl acetate was added thereto, and the mixture was stirred and thus obtained mixture was separated to recover an organic layer. To the obtained organic layer was added 10 parts of ion-exchanged water to wash, and separated to recover an organic layer. The recovered organic layer was concentrated, and then column-fractionated under the condition below, whereby giving 1.46 parts of the compound (a1-D).

Developing medium: silica gel 60, 200 mesh (Merck & Co., Inc.)

Developing solvent: n-heptane/ethyl acetate=1/1 (volume ratio)

MS: 470.2

Example 9

Synthesis of Compound (a1-E)

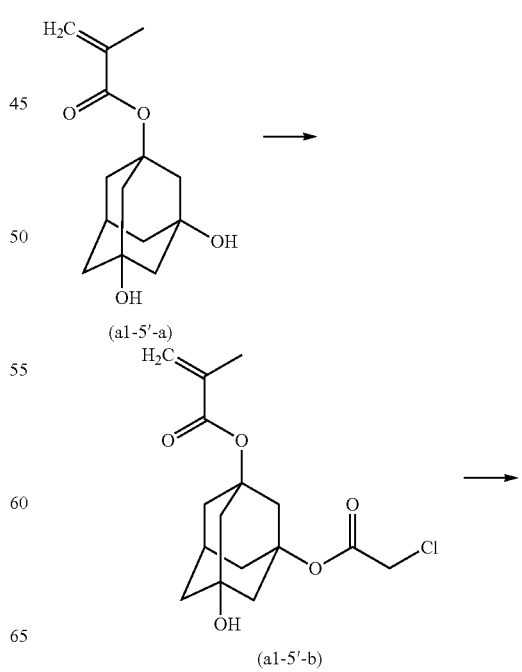

-continued

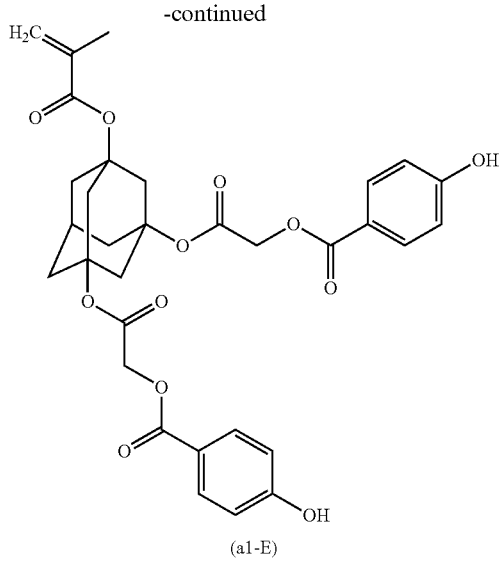
(a1-E)

0.28 parts of a compound (a1-E) was produced in the same manner as in Example 3 except that 3.45 parts of 4-hydroxybenzoic acid, 1.73 parts of potassium carbonate and 0.42 parts of potassium iodide were used instead of 1.38 parts of 4-hydroxy-benzoic acid, 0.69 parts of potassium carbonate and 0.17 parts of potassium iodide.

Example 10

Synthesis of Resin (B1)

2-ethyl-2-adamantyl methacrylate and the compound (a1-4) were mixed with molar ratio 25:75, and dioxane was added thereto in an amount equal to 1.5 weight times of the total amount of monomers to obtain a solution. Azobisisobutyronitrile and azobis(2,4-dimethylvaleronitrile) were added as initiators thereto in an amount of 1 mol % and 3 mol % respectively with respect to the entire amount of monomers, and the resultant mixture was heated for about 5 hours at 75° C. After that, the reaction solution was poured into a mixture methanol and ion-exchanged water in large amounts to precipitate. These operations were repeated 3 times for purification, whereby giving 65% yield of copolymer having a weight average molecular weight of about 7900. This copolymer was designated Resin B1.

Example 11

Synthesis of Resin (B2)

2-ethyl-2-adamantyl methacrylate and the compound (a1-5) were mixed with molar ratio 25:75, and dioxane was added thereto in an amount equal to 1.5 weight times of the total amount of monomers to obtain a solution. Azobisisobutyronitrile and azobis(2,4-dimethylvaleronitrile) were added as initiators thereto in an amount of 1 mol % and 3 mol % respectively with respect to the entire amount of monomers, and the resultant mixture was heated for about 5 hours at 75° C. After that, the reaction solution was poured into a mixture methanol and ion-exchanged water in large amounts to precipitate. These operations were repeated 3 times for purification, whereby giving 64% yield of copolymer having a weight average molecular weight of about 7800. This copolymer was designated Resin B2.

Example 12

Synthesis of Resin (B3)

2-ethyl-2-adamantyl methacrylate and the compound (a1-4') were mixed with molar ratio 25:75, and dioxane was added thereto in an amount equal to 1.5 weight times of the total amount of monomers to obtain a solution. Azobisisobutyronitrile and azobis(2,4-dimethylvaleronitrile) were added as initiators thereto in an amount of 1 mol % and 3 mol % respectively with respect to the entire amount of monomers, and the resultant mixture was heated for about 5 hours at 75° C. After that, the reaction solution was poured into a mixture methanol and ion-exchanged water in large amounts to precipitate. These operations were repeated 3 times for purification, whereby giving 60% yield of copolymer having a weight average molecular weight of about 7600. This copolymer was designated Resin B3.

Example 13

Synthesis of Resin (B4)

2-ethyl-2-adamantyl methacrylate and the compound (a1-5') were mixed with molar ratio 25:75, and dioxane was added thereto in an amount equal to 1.5 weight times of the total amount of monomers to obtain a solution. Azobisisobutyronitrile and azobis(2,4-dimethylvaleronitrile) were added as initiators thereto in an amount of 1 mol % and 3 mol % respectively with respect to the entire amount of monomers, and the resultant mixture was heated for about 5 hours at 75° C. After that, the reaction solution was poured into a mixture methanol and ion-exchanged water in large amounts to precipitate. These operations were repeated 3 times for purification, whereby giving 59% yield of copolymer having a weight average molecular weight of about 7300. This copolymer was designated Resin B4.

Example 14

Synthesis of Resin (B5)

2-ethyl-2-adamantyl methacrylate and the compound (a1-A) were mixed with molar ratio 25:75, and dioxane was added thereto in an amount equal to 1.5 weight times of the total amount of monomers to obtain a solution. Azobisisobutyronitrile and azobis(2,4-dimethylvaleronitrile) were added as initiators thereto in an amount of 1 mol % and 3 mol % respectively with respect to the entire amount of monomers, and the resultant mixture was heated for about 5 hours at 75° C. After that, the reaction solution was poured into a mixture methanol and ion-exchanged water in large amounts to precipitate. These operations were repeated 3 times for purification, whereby giving 52% yield of copolymer having a weight average molecular weight of about 7000. This copolymer was designated Resin B5.

Example 15

Synthesis of Resin (B6)

2-ethyl-2-adamantyl methacrylate and the compound (a1-B) were mixed with molar ratio 25:75, and dioxane was added thereto in an amount equal to 1.5 weight times of the total amount of monomers to obtain a solution. Azobisisobutyronitrile and azobis(2,4-dimethylvaleronitrile) were added as initiators thereto in an amount of 1.2 mol % and 3.6 mol % respectively with respect to the entire amount of monomers, and the resultant mixture was heated for about 5 hours at 75° C. After that, the reaction solution was poured into a mixture methanol and ion-exchanged water in large amounts to precipitate. These operations were repeated 3 times for purification, whereby giving 55% yield of copolymer having a weight average molecular weight of about 5900. This copolymer was designated Resin B6.

Example 16

Synthesis of Resin (B7)

2-ethyl-2-adamantyl methacrylate and the compound (a1-C) were mixed with molar ratio 25:75, and dioxane was added thereto in an amount equal to 1.5 weight times of the total amount of monomers to obtain a solution. Azobisisobutyronitrile and azobis(2,4-dimethylvaleronitrile) were added as initiators thereto in an amount of 1.5 mol % and 4.5 mol % respectively with respect to the entire amount of monomers, and the resultant mixture was heated for about 5 hours at 75° C. After that, the reaction solution was poured into a mixture methanol and ion-exchanged water in large amounts to precipitate. These operations were repeated 3 times for purification, whereby giving 48% yield of copolymer having a weight average molecular weight of about 4800. This copolymer was designated Resin B7.

Example 17

Synthesis of Resin (B8)

2-ethyl-2-adamantyl methacrylate and the compound (a1-D) were mixed with molar ratio 25:75, and dioxane was added thereto in an amount equal to 1.5 weight times of the total amount of monomers to obtain a solution. Azobisisobutyronitrile and azobis(2,4-dimethylvaleronitrile) were added as initiators thereto in an amount of 1.2 mol % and 3.6 mol % respectively with respect to the entire amount of monomers, and the resultant mixture was heated for about 5 hours at 75° C. After that, the reaction solution was poured into a mixture methanol and ion-exchanged water in large amounts to precipitate. These operations were repeated 3 times for purification, whereby giving 48% yield of copolymer having a weight average molecular weight of about 5600. This copolymer was designated Resin B8.

Example 18

Synthesis of Resin (B9)

2-ethyl-2-adamantyl methacrylate and the compound (a1-E) were mixed with molar ratio 25:75, and dioxane was added thereto in an amount equal to 1.5 weight times of the total amount of monomers to obtain a solution. Azobisisobutyronitrile and azobis(2,4-dimethylvaleronitrile) were added as initiators thereto in an amount of 1.2 mol % and 3.6 mol % respectively with respect to the entire amount of monomers, and the resultant mixture was heated for about 5 hours at 75° C. After that, the reaction solution was poured into a mixture methanol and ion-exchanged water in large amounts to precipitate. These operations were repeated 3 times for purification, whereby giving 44% yield of copolymer having a weight average molecular weight of about 5500. This copolymer was designated Resin B9.

Synthesis of Resin (Z1)

39.7 g (0.16 mole) of 2-ethyl-2-adamantyl methacrylate and 103.8 g (0.64 mole) of p-acetoxystyrene were dissolved in 265 g isopropanol, and the obtained solution was elevated the temperature to 75° C. under an atmosphere of nitrogen. A solution in which 11.05 g (0.048 mole) of dimethyl 2,2-azobis (2-methylpropionate) as a radical initiator was dissolved in 22.11 g of isopropanol was added in the form of drops thereto. The reacted solution was heated to reflux for 12 hours, cooled and pored into methanol in the large amounts to precipitate a polymer. The precipitate was filtrated, whereby giving 250 g of a copolymer of 2-ethyl-2-adamantyl methacrylate and p-acetoxystyrene (containing methanol).

250 g of thus obtained copolymer and 10.3 g (0.084 mole) of 4-dimethylaminopyridine were added to 202 g of methanol, and the mixture was heated to reflux for 20 hours, cooled, neutralized with 7.6 g (0.126 mole) of glacial acetic acid, and pored into a water in the large amounts to precipitate. The precipitate was filtrated, and dissolved into acetone. The obtained solution was pored into a water in the large amounts, these operations were repeated 3 times for purification, whereby giving 95.9 g of a copolymer of 2-ethyl-2-adamantyl methacrylate and p-hydroxystyrene, having a weight average molecular weight of about 8600 (GPC polystyrene conversion) and a copolymer ratio of about 20:80 This copolymer was designated Resin Z1.

Synthesis of Resin (Z2)

102.8 g of a copolymer of 2-ethyl-2-adamantyl methacrylate and p-hydroxystyrene, having a weight average molecular weight of about 8200 (GPC polystyrene conversion) and a copolymer ratio of about 30:70 ($C^{13}$ NMR measurement) was produced in the same manner as in Synthesis of Resin (Z1) except that 59.6 g (0.24 mole) of 2-ethyl-2-adamantyl methacrylate and 90.8 g (0.56 mole) of p-acetoxystyrene was used. This copolymer was designated Resin Z2.

Examples and Comparative Examples

The resist compositions were prepared by mixing and dissolving each of the components shown in Table 1, and then filtering through a fluororesin filter having 0.2 μm pore diameter.

TABLE 1

|  | Resin (parts) | Acid generator (parts) | Quencher (parts) | PB/PEB (° C.) |
|---|---|---|---|---|
| Ex. 19 | B1 = 10 | A1 = 1.50 | Q1/Q2 = 0.03/0.03 | 110/110 |
| Ex. 20 | B2 = 10 | A1 = 1.50 | Q1/Q2 = 0.03/0.03 | 110/110 |
| Ex. 21 | B3 = 10 | A1 = 1.50 | Q1/Q2 = 0.03/0.03 | 110/110 |
| Ex. 22 | B4 = 10 | A1 = 1.50 | Q1/Q2 = 0.03/0.03 | 110/110 |
| Ex. 23 | B5 = 10 | A1 = 1.50 | Q1/Q2 = 0.03/0.03 | 110/110 |
| Ex. 24 | B6 = 10 | A1 = 1.50 | Q1/Q2 = 0.03/0.03 | 110/110 |
| Ex. 25 | B7 = 10 | A1 = 1.50 | Q1/Q2 = 0.03/0.03 | 110/110 |
| Ex. 26 | B8 = 10 | A1 = 1.50 | Q1/Q2 = 0.03/0.03 | 110/110 |
| Ex. 27 | B9 = 10 | A1 = 1.50 | Q1/Q2 = 0.03/0.03 | 110/110 |

TABLE 1-continued

|  | Resin (parts) | Acid generator (parts) | Quencher (parts) | PB/PEB (° C.) |
|---|---|---|---|---|
| Ex. 28 | B2 = 13.5 | A2/A3 = 0.45/0.6 | Q1 = 0.049 | 110/110 |
| Comp. Ex. 1 | Z1/Z2 = 6.75/6.75 | A2/A3 = 0.45/0.6 | Q1 = 0.049 | 110/110 |

<Acid Generator>
Acid Generator A1:

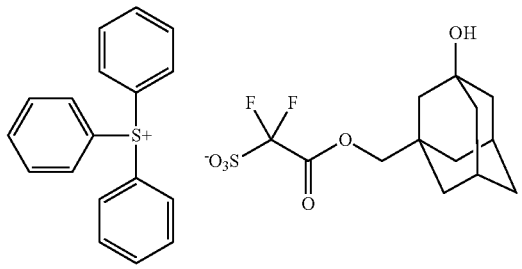

Acid Generator A2:
triphenylsulfonium 2,4,6-triisopropylbenzenesulfonate
Acid Generator A3:
bis(cyclohexylsulfonium)diazomethane
<Basic compound: Qencher>
Q1: 2,6-diisopropylaniline,
Q2: tetrabutylammonium hydroxide
<Solvent of Resist Composition>

| Propylene glycol monomethyl ether acetate | 400 parts |
|---|---|
| Propylene glycol monomethyl ether | 100 parts |
| γ-butyrolactone | 5 parts |

[Evaluation of Resist Composition for Electron-Beam Lithography]

Silicon wafers were treated using hexamethyldisilazane for 60 sec on a direct hot plate at 90° C.

The above resist liquids were then applied thereon by spin coating so that the thickness of the resulting film became 0.06 μm after drying.

The obtained wafers were then pre-baked for 60 sec on a direct hot plate at the temperatures given in the "PB" column in Table 1.

Line and space patterns were then exposed through stepwise changes in exposure quantity using an electron beam lithography system ("HL-800D 50 keV" by Hitachi), on the wafers on which the resist film had thus been formed.

The exposure was followed by 60 seconds of post-exposure baking at the temperatures given in the "PEB" column in Table 1.

This was followed by 60 sec of puddle development with 2.38 wt % tetramethylammonium hydroxide aqueous solution.

Table 2 gives the results of scanning electron microscopy of the developed pattern on the silicon substrate.

Line edge roughness (LER) evaluation: when the wall surface of the resist pattern following the lithography process in which the exposure amount was set so as to resolved a 100 nm line and space pattern to 1:1, was observed using a scanning electron microscope, a OO was given if the difference between the highest part and the lowest part on the resist pattern side wall (i.e., difference in height of the asperity on the side wall of the resist pattern) was ≦7 nm, a O was given if the difference on the resist pattern side wall was >7 nm and ≦8 nm, and it received an X if these are >8 nm. In the Table 2, numerical values represents measurement results (unit: nm).

TABLE 2

|  | LER |
|---|---|
| Ex. 19 | oo (6.8) |
| Ex. 20 | oo (6.4) |
| Ex. 21 | oo (6.7) |
| Ex. 22 | oo (6.4) |
| Ex. 23 | o (7.3) |
| Ex. 24 | o (7.0) |
| Ex. 25 | o (7.2) |
| Ex. 26 | o (7.8) |
| Ex. 27 | oo (7.0) |
| Ex. 28 | o (8.0) |
| Comp. Ex. 1 | x (8.5) |

[Evaluation of Resist Composition for EUV Lithography]

Silicon wafers were treated using hexamethyldisilazane for 60 sec on a direct hot plate at 90° C.

The above resist liquids were then applied thereon by spin coating so that the thickness of the resulting film became 50 nm after drying.

The obtained wafers were then pre-baked for 60 sec on a direct hot plate at the temperatures given in the "PB" column in Table 1

Line and space patterns were then exposed through stepwise changes in exposure quantity using an EUV stepper on the wafers on which the resist film had thus been formed.

The exposure was followed by 60 seconds of post-exposure baking at the temperatures given in the "PEB" column in Table 1

This was followed by 60 sec of puddle development with 2.38 wt % tetramethylammonium hydroxide aqueous solution.

Table 3 gives the results of scanning electron microscopy of the developed pattern on the silicon substrate.

Line edge roughness (LER) evaluation: when the wall surface of the resist pattern following the lithography process in which the exposure amount was set so as to resolved a 50 nm line and space pattern to 1:1 was observed using a scanning electron microscope, a OO was given if the difference between the highest part and the lowest part on the resist pattern side wall was ≦5 nm, a O was given if the difference on the resist pattern side wall was >5 nm and ≦7 nm, and it received an X if these are >7 nm. In the Table 3, numerical values represents measurement results (unit: nm).

Table 3 gives the there results.

TABLE 3

|  | LER |
|---|---|
| Ex. 19 | o (5.4) |
| Ex. 20 | oo (4.9) |

TABLE 3-continued

| | LER |
|---|---|
| Ex. 21 | ○ (5.4) |
| Ex. 22 | ○○ (4.8) |
| Comp. Ex. 1 | × (7.2) |

According to the compound and the resist composition containing a resin which has a structural unit derived from the compound of the present invention, it is possible to achieve satisfactory pattern line edge roughness in the pattern formed.

This application claims priority to Japanese Patent Application No. JP 2009-202725. The entire disclosure of Japanese Patent Application No. JP 2009-202725 is hereby incorporated herein by reference.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents. Thus, the scope of the invention is not limited to the disclosed embodiments.

What is claimed is:

1. A compound represented by the formula (A);

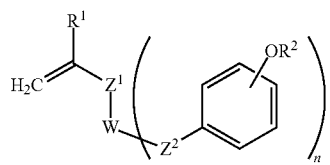

(A)

wherein $R^1$ represents a hydrogen atom or a $C_1$ to $C_6$ alkyl group;

$Z^1$ represents —CO—O—* or —CO—O—$(CH_2)_k$—CO—O—*;

$Z^2$ represents a single bond, *—O—CO—, *—CO—O—, *—O—$(CH_2)_k$—CO—, *—CO—$(CH_2)_k$—O—, *—O—$(CH_2)_k$—CO—O—, *—O—CO—$(CH_2)_k$—O— or *—O—CO—$(CH_2)_k$—O—CO—;

k represents an integer of 1 to 6;

* represents a binding position to W;

W represents a $C_4$ to $C_{36}$ (n+1) valent alicyclic hydrocarbon group, one or more hydrogen atoms contained in the alicyclic hydrocarbon group may be replaced by a halogen atom, a $C_1$ to $C_{12}$ alkyl group, a $C_1$ to $C_{12}$ alkoxy group, a $C_2$ to $C_4$ acyl group or —$OR^{10}$;

$R^{10}$ represents a hydrogen atom or a group represented by the formula ($R^2$-2);

$R^2$ represents a hydrogen atom, a group represented by the formula ($R^2$-1) or a group represented by the formula ($R^2$-2);

n represents an integer of 1 to 3;

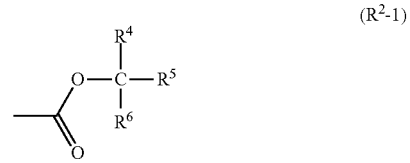

(R²-1)

wherein $R^4$, $R^5$ and $R^6$ independently represent a $C_1$ to $C_{12}$ hydrocarbon group;

(R²-2)

wherein $R^7$ and $R^8$ independently represent a hydrogen atom or a $C_1$ to $C_{12}$ hydrocarbon group;

$R^9$ represents a $C_1$ to $C_{14}$ hydrocarbon group.

2. The compound according to claim 1, wherein the compound represented by the formula (A) is a compound represented by the formula (A1);

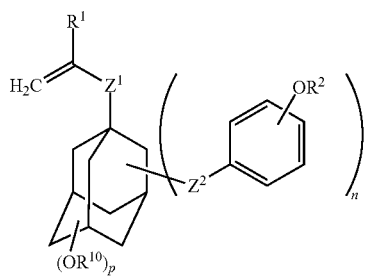

(A1)

wherein $R^1$, $R^2$, $R^{10}$, $Z^1$, $Z^2$ and n represent the same meaning as defined in claim 1, p represents an integer of 0 to 3, provided that n+p is an integer of 1 to 3.

3. The compound according to claim 1, wherein the $Z^1$ is —CO—O—*.

4. The compound according to claim 1, wherein the $Z^2$ is *—O—$(CH_2)_k$—CO or *—O—CO—$(CH_2)_k$—O—CO—, wherein k represents the same meaning as defined in claim 1.

5. The compound according to claim 1, wherein the n represents 1.

6. A resin comprising a structural unit derived from the compound of the claim 1.

7. The resin according to claim 6, which further comprising an acid-labile group, and being insoluble or poorly soluble in aqueous alkali solution but becoming soluble in aqueous alkali solution by the action of acid.

8. A resist composition comprising a resin according to claim 6, and an acid generator.

9. The resist composition according to claim 8, which further comprises a basic compound.

10. A method for producing a resist pattern comprising steps of;

(1) applying the resist composition according to claim 8 or 9 onto a substrate;

(2) drying the applied composition to form an composition layer;
(3) exposing the composition layer using an exposure device;
(4) baking the exposed composition layer and,
(5) developing the baked composition layer using a developing apparatus,
wherein in step (3), the composition layer is exposed to light and in step (5), the composition is developed utilizing an alkaline developing solution.

* * * * *